US012637441B2

(12) United States Patent
Lu et al.

(10) Patent No.: US 12,637,441 B2
(45) Date of Patent: May 26, 2026

(54) PRODRUGS OF THE TYROSINE KINASE INHIBITOR FOR TREATING CANCER

(71) Applicant: RISEN (SUZHOU) PHARMA TECH CO., LTD., Suzhou (CN)

(72) Inventors: Jiasheng Lu, Shanghai (CN); Jiamin Gu, Suzhou (CN); Gang Chen, Suzhou (CN); Qiguo Zhang, Suzhou (CN); Chengyong Sun, Suzhou (CN); Xianqi Kong, Dollard-des-Ormeaux (CA)

(73) Assignee: RISEN (SUZHOU) PHARMA TECH CO., LTD., Suzhou (CN)

( * ) Notice: Subject to any disclaimer, the term of this patent is extended or adjusted under 35 U.S.C. 154(b) by 28 days.

(21) Appl. No.: 17/005,852

(22) Filed: Aug. 28, 2020

(65) Prior Publication Data

US 2021/0078970 A1 Mar. 18, 2021

Related U.S. Application Data

(60) Provisional application No. 62/994,364, filed on Mar. 25, 2020.

(30) Foreign Application Priority Data

Aug. 30, 2019 (CN) ........................ 201910817505.X
Aug. 30, 2019 (CN) ........................ 201910818675.X
Aug. 30, 2019 (CN) ........................ 201910818779.0

(51) Int. Cl.

| | |
|---|---|
| ***C07D 401/06*** | (2006.01) |
| ***A61K 9/00*** | (2006.01) |
| ***A61P 35/00*** | (2006.01) |
| ***C07D 231/56*** | (2006.01) |
| ***C07D 405/14*** | (2006.01) |
| ***C07F 9/06*** | (2006.01) |

(52) U.S. Cl.

CPC .......... *C07D 401/06* (2013.01); *A61K 9/0053* (2013.01); *A61P 35/00* (2018.01); *C07D 231/56* (2013.01); *C07D 405/14* (2013.01); *C07F 9/06* (2013.01)

(58) Field of Classification Search

None

See application file for complete search history.

(56) References Cited

FOREIGN PATENT DOCUMENTS

| | | | | |
|---|---|---|---|---|
| CN | 106317017 A | | 1/2017 | |
| CN | 106336297 A | | 1/2017 | |
| CN | 106478596 A | * | 3/2017 | ........... C07D 401/06 |
| CN | 112442009 A | | 3/2021 | |
| CN | 112442010 A | | 3/2021 | |
| CN | 112442011 A | | 3/2021 | |
| EP | 19181804.6 | | 6/2019 | |
| EP | 20150240.8 | | 1/2020 | |
| WO | 200102369 A2 | | 1/2001 | |
| WO | WO 2015/038649 A1 | * | 3/2015 | ............. A61K 31/52 |
| WO | 2019196945 A1 | | 10/2019 | |
| WO | WO 2020/254612 A1 | * | 12/2020 | ............. A61K 47/69 |
| WO | WO 2020/254613 A1 | * | 12/2020 | ............. A61K 47/69 |

OTHER PUBLICATIONS

Chekal et al., Development of an Efficient Pd-Catalyzed Coupling Process for Axitinib, Organic Process Research & Development, 2014, 18(1), 266-274.

International Search Report and Written Opinion issued in co-pending International application No. PCT/CA2020/051177 on Nov. 16, 2020.

Supplementary European Search Report issued in corresponding European patent application No. 20857153.9 on Jul. 25, 2023.

* cited by examiner

*Primary Examiner* — Brian J Davis

(74) *Attorney, Agent, or Firm* — BCF LLP

(57) ABSTRACT

There are provided compounds of Formula I, and pharmaceutically acceptable salts and esters thereof, and pharmaceutical compositions thereof, useful for inhibition or modulation of the activity of tyrosine kinases and treatment of disease states or conditions mediated by tyrosine kinases, including cancers.

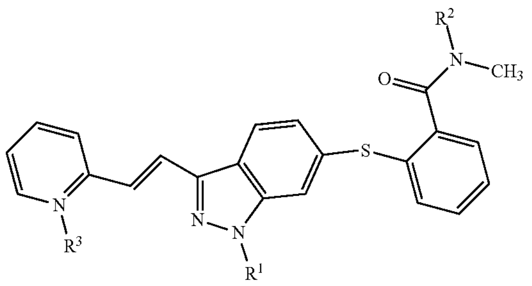

20 Claims, 2 Drawing Sheets

*, p<0.05; **, p<0.01.

PRODRUGS OF THE TYROSINE KINASE INHIBITOR FOR TREATING CANCER

CROSS-REFERENCE TO RELATED APPLICATIONS

This application claims the benefit of priority to Chinese application no. 201910818779.0 filed Aug. 30, 2019; Chinese application no. 201910817505.X filed Aug. 30, 2019; Chinese application no. 201910818675.X filed Aug. 30, 2019; and U.S. application No. 62/994,364 filed Mar. 25, 2020; the entire contents of each of which are hereby incorporated by reference.

FIELD

The present disclosure relates to prodrugs of N-methyl-2-((3-((1E)-2-(2-pyridinyl)ethenyl)-1H-indazol-6-yl)thio) benzamide and compositions thereof that are tyrosine kinase inhibitors (TKIs), and uses thereof to treat disease states or conditions mediated by tyrosine kinases, such as cancers.

BACKGROUND

Axitinib (chemical name: N-methyl-2-((3-((1E)-2-(2-pyridinyl)ethenyl)-1H-indazol-6-yl)thio)benzamide; trade name: Inlyta®) is a small molecule tyrosine kinase inhibitor (TKI) used for treating cancer (see, for example, International PCT Application Publication no. WO2001002369; the compound's structure is shown below). Axitinib has been shown to significantly inhibit growth of breast cancer in animal xenograft models (Wilmes, L. J. et al., Magn. Reson. Imaging, 2007, 25(3):319-327). The drug has shown partial responses in clinical trials for renal cell carcinoma (RCC) (Rini, B. et al., J. of Clin. Oncol. 2005, ASCO Annual Meeting Proceedings, 23 (16S): 4509), and for several other tumor types (Rugo, H. S. et al., J. Clin. Oncol., 2005, 23:5474-5483). Axitinib was approved for treatment of RCC by the U.S. Food and Drug Administration after showing a modest increase in progression-free survival.

The structure of axitinib is shown here:

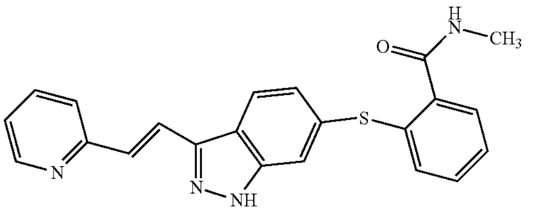 [SMILES: CNC(=O)c1ccccc1Sc1ccc2c(/C=C/c3ccccn3)n[nH]c2c1]

Axitinib is used as a targeted anti-cancer therapy since it targets and binds to the vascular endothelial growth factor receptors (VEGFR) on the inside of cancer cells. VEGFR is found on the surface of many normal and cancerous cells. By binding to these receptors, axitinib blocks an important pathway that promotes angiogenesis (the formation of new blood vessels by tumors) (Escudier, B. and Gore, M., "Axitinib for the Management of Metastatic Renal Cell Carcinoma", Drugs in R&D, 2011, 11(2):113-126).

Further, data from a multi-center phase II study in patients with advanced differentiated (papillary, follicular, or Hurthle) thyroid cancer supports the use of axitinib in the management of $I^{131}$-refractory disease or in patients who could not receive $I^{131}$ (Cohen, Ezra E. W. et al., J. Clin. Oncol., 2008, 26(29):4708-4713). Another multi-center phase II study in advanced thyroid cancer also supports the use of axitinib in the management of $I^{131}$-refractory disease (Locati, L. D. et al., Cancer, 2014, 120(17):2694-2703). Therefore, axitinib is also used off-label for the treatment of thyroid cancer (differentiated, advanced).

One problematic aspect of using axitinib in the treatment of cancer is its side effects. Many different adverse effects have been reported, including diarrhea, hypertension, fatigue, decreased appetite, nausea, dysphonia, hand-foot syndrome, weight decrease, vomiting, asthenia, and constipation, with the most common side effects occurring in more than 20% of patients (FDA Prescribing Information, Jan. 30, 2012).

As seen with other orally administered drugs, including other tyrosine kinase inhibitors, Axitinib's pharmacokinetics (PK) were variable in healthy volunteers as well as in cancer patients (Garrett, M. et al., *Br. J. Clin. Pharmacol.*, 2013, 77(3): 480-492). Notably, a large variability in axitinib PK was evident from the estimated residual standard deviation of 50.9% for oral administration and 34.2% for intravenous administration of axitinib, which could not be reduced by introduction of inter-occasion variability in the model.

The exact causes for this variability in axitinib PK are yet to be elucidated. Axitinib is known to be heavily metabolized (Smith, B. J. et al., *Drug Metab. Dispos.*, 2014, 42:918-931; and Zientek, M. A, et al., *Drug Meta. Dispos.*, 2016, 44(1):102-114). Among the three major metabolites, one is a product of glucuronidation at the nitrogen atom of the central pyrazole ring (M7), and the other two are metabolic products initiated from a mono-oxygenation step. Because axitinib is primarily metabolized by CYP3A4/5, it has been speculated that one major source of variability may be differences in CYP3A4/5 expression and/or activity in the liver and intestine (a 10- to 40-fold variability in expression of CYP3A4/5 has been reported in healthy subjects). Since axitinib is a low extraction drug, the metabolic clearance of axitinib may be particularly sensitive to variable levels of hepatic and intestinal metabolizing enzymes. Another possible explanation is variability in plasma binding of axitinib between subjects. With regard to high residual (intra-subject) variability, it is plausible that differences in dissolution and subsequent gastrointestinal absorption of axitinib may be a contributing factor. Since axitinib solubility is pH-dependent, with solubility declining with increasing pH, changes in pH values in stomach and duodenum may lead to variable dissolution of axitinib.

Since not only the toxicity but also the clinical benefit of axitinib may be affected by its plasma exposure, it is critical to identify clinical factors that contribute to the variability in axitinib PK. In order to reduce toxicity and to maintain stable therapeutic benefit, it is desirable to eliminate or reduce the PK variability of axitinib.

A prodrug is a medication or compound that, after administration, is metabolized (i.e., converted within the body) into a pharmacologically active drug (see for example, Rautio, J. et al., "The expanding role of prodrugs in contemporary drug design and development", *Nat. Rev. Drug Discov.*, 2018, 17, 559-587; and Miles H., et al., Pharmacology: Principles and Practice. Academic Press, Jun. 19, 2009, pp. 216-217). Inactive prodrugs are pharmacologically inactive medications that are metabolized into an active form within the body. Thus, instead of administering a drug directly, a corresponding prodrug may be used to improve how a medicine is absorbed, distributed, metabolized, and/or excreted (ADME) (for example, see Malhotra, B., et al., "The design and development of fesoterodine as a prodrug of 5-hydroxymethyl tolterodine (5-HMT), the active metabolite of tolterodine", *Curr. Med. Chem.*, 2009, 16 (33): 4481-9; and Stella, V. J., et al, "Prodrugs. Do they have advantages in clinical practice?", Drugs, 1985, 29 (5): 455-73). A prodrug may be used to improve how selectively a drug interacts with cells or processes that are not its intended target. This can reduce adverse or unintended effects of a drug, which is especially important for treatments like chemotherapy that often have severe unintended and undesirable side effects. For example, tenofovir alafenamide (TAF), a novel prodrug of tenofovir, was developed to deliver enhanced antiviral potency and reduced systemic toxicity (Byrne, R., et al., *Therap. Adv. Gastroenterol.*, 2018, 11:1-12).

SUMMARY

It is an object of the present invention to ameliorate at least some of the deficiencies present in the prior art. Embodiments of the present technology have been developed based at least in part on the inventors' appreciation that there is a need for modifying or improving the pharmacokinetic profile of N-methyl-2-((3-((1E)-2-(2-pyridinyl)ethenyl)-1H-indazol-6-yl)thio)benzamide for its therapeutic applications through developing a prodrug of this particular compound. These and other needs can be satisfied by the disclosure herein of axitinib derivatives and/or prodrugs, pharmaceutical compositions and uses thereof to inhibit or modulate the activity of tyrosine kinase and to treat disease states or conditions mediated by tyrosine kinases, such as cancers.

Without wishing to be limited by theory, it is believed that a proper prodrug strategy with axitinib would be able to modulate the pharmacokinetic profile of the drug, through changing the course and/or rate of metabolic pathways of the drug. As one example, protection of the ring nitrogen atoms in axitinib may modify the electron density of the system and thus modulate the rate of oxidation and subsequently modulate the metabolism of the compound. When such a protection is introduced to the pyrazole nitrogen, it may avoid, at least to a certain extent, glucuronidation at this nitrogen.

In a first aspect, there are provided compounds of Formula I, or pharmaceutically acceptable salts, esters, solvates, or polymorphs thereof:

(I)

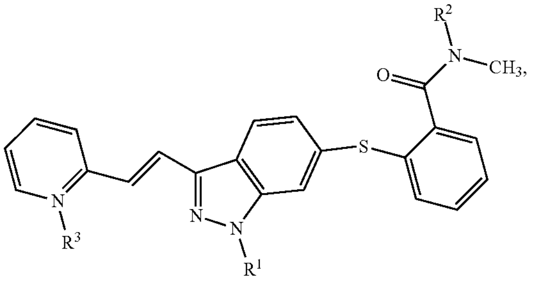

where $R^1$ and $R^2$ are independently a hydrogen (H) or a protecting group (P); $R^3$, which may be present or absent, is a protecting group, and when $R^3$ is present, the nitrogen atom is positively charged and a counterion is also present; provided that the compound of Formula I is not axitinib. In embodiments where both $R^1$ and $R^2$ are a protecting group (P), the protecting groups may be the same or different.

In some embodiments, compounds provided herein are prodrugs of axitinib, i.e., are metabolized or converted in a subject to axitinib.

In one embodiment, a compound of Formula I is a compound of Formula II, or a pharmaceutically acceptable salt, ester, solvate, or polymorph thereof:

(II)

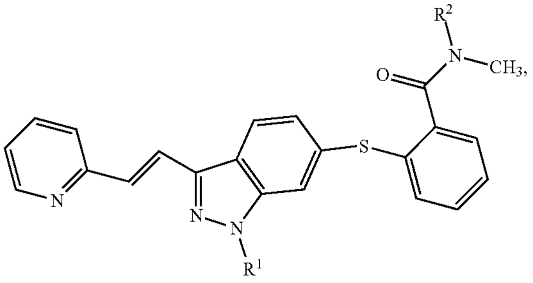

where $R^1$ and $R^2$ are independently a hydrogen (H) or a protecting group (P), and when both $R^1$ and $R^2$ are a protecting group, the protecting groups may be the same or different.

In another embodiment, a compound of Formula I is a compound of Formula III, or a pharmaceutically acceptable salt, ester, solvate, or polymorph thereof:

(III)

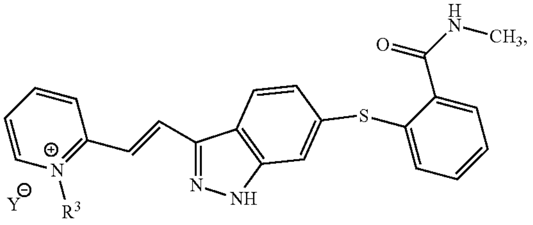

where $R^3$ is a protecting group (P), and is a counterion.

In one embodiment, a protecting group is selected from acyl group, alkylcarbonyl group, arylcarbonyl group, alkylthiocarbonyl group, arylthiocarbonyl group, alkylcarbamoyl group, arylcarbamoyl group, substituted or unsubstituted acetyl, substituted or unsubstituted aminoalkanoyl, substituted or unsubstituted α-aminoalkanoyl, acyl group derived from a natural or an unnatural amino acid with or without substitution, acyl group of a peptide residue, phosphonyl, phosphinyl, aminophophinyl, alkylaminophophinyl, sulfonyl, cycloalkane-carbonyl, heterocycloalkane-carbonyl, alkoxycarbonyl, aryloxycarbonyl, heteroalkoxycarbonyl, heteroaryloxycarbonyl, and O-substituted hydroxymethyl group with or without substituents.

In another embodiment, a protecting group is selected from $R^4W(R^5R^6C)_m$—, where: m is an integer selected from 0 to 6; W is oxygen (—O—), sulfur (—S—), nitrogen (—NH—), or absent; $R^5$ and $R^6$ are independently a hydrogen or a lower alkyl group; and $R^4$ is

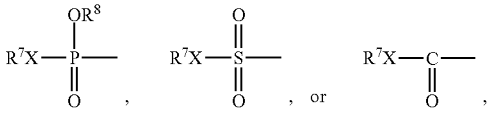

where X is oxygen (—O—), sulfur (—S—), nitrogen (—NH—), or a methylene (—$CH_2$—) group, $R^7$ and $R^8$ are independently a hydrogen, a substituted or unsubstituted alkyl or cycloalkyl, an aryl or heteroaryl group without or with substitution, a PEG moiety (such as $R^{10}$—$(OCH_2CH_2)_n$—, where n=1 to 10 and $R^{10}$ is a hydrogen or a lower alkyl), an ester-forming group such as a lower alkyl or an aryl group; or a salt-forming moiety when X is oxygen or sulfur, such as a sodium, a potassium, a tetraethylammonium, or a tetrabutylammonium; or, the combination of $R^7$ and X is an alky or aryl group with or without further substitution; provided that the compound of Formula I, II, or III is not axitinib.

In some embodiments, a counterion is selected from, but not limited to, halide ion ($F^-$, $Cl^-$, $Br^-$, and $I^-$), sulfate ion, methanesulfonate ion, toluenesulfonate ion, oxalate ion, and other pharmaceutically accepted anionic moiety.

In some embodiments, the compound of Formula I is a compound shown in Table 1, or a pharmaceutically-acceptable salt, ester, chelator, hydrate, solvate, stereoisomer, or polymorphic form thereof.

TABLE 1

| Examples of axitinib derivative compounds. | |
|---|---|
| 1 | 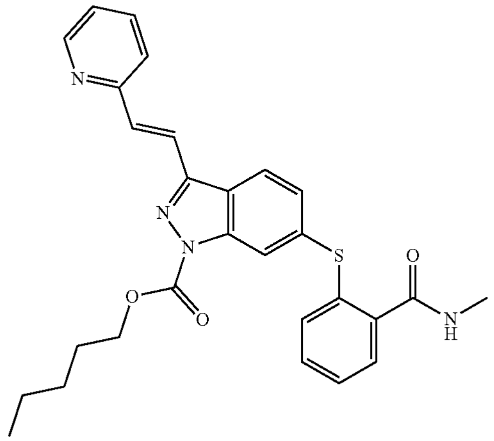 [SMILES: CCCCCOC(=O)n1nc(/C=C/c2ccccn2)c2ccc(Sc3ccccc3C(=O)NC)cc21] |
| 2 | 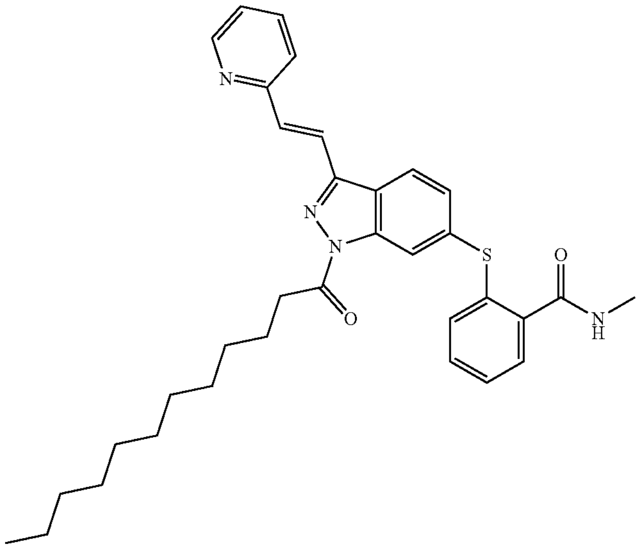 [SMILES: CCCCCCCCCCCC(=O)n1nc(/C=C/c2ccccn2)c2ccc(Sc3ccccc3C(=O)NC)cc21] |

TABLE 1-continued
| Examples of axitinib derivative compounds. | |
|---|---|
| 3 | 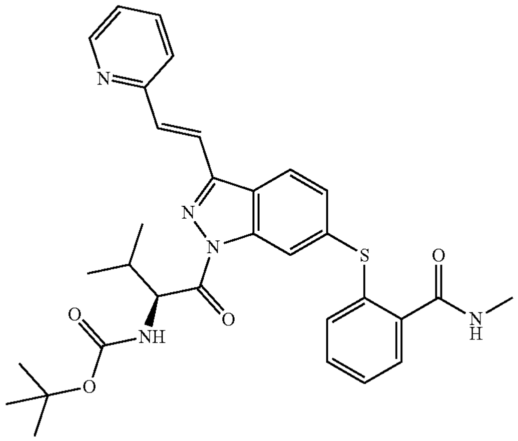 [SMILES: CNC(=O)c1ccccc1Sc1ccc2c(/C=C/c3ccccn3)nn(C(=O)[C@@H](NC(=O)OC(C)(C)C)C(C)C)c2c1] |
| 4 | 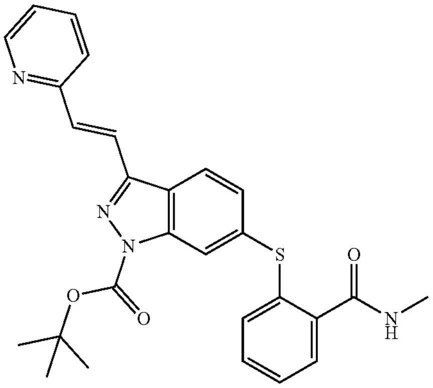 [SMILES: CNC(=O)c1ccccc1Sc1ccc2c(/C=C/c3ccccn3)nn(C(=O)OC(C)(C)C)c2c1] |
| 5 | 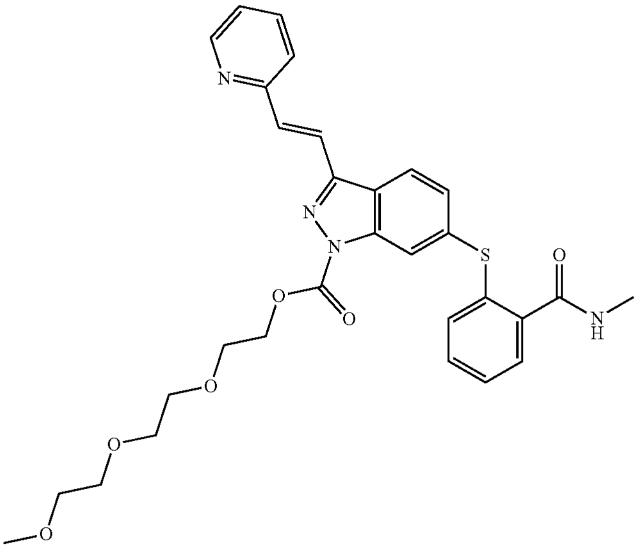 |

TABLE 1-continued
| Examples of axitinib derivative compounds. | |
|---|---|
| 6 | 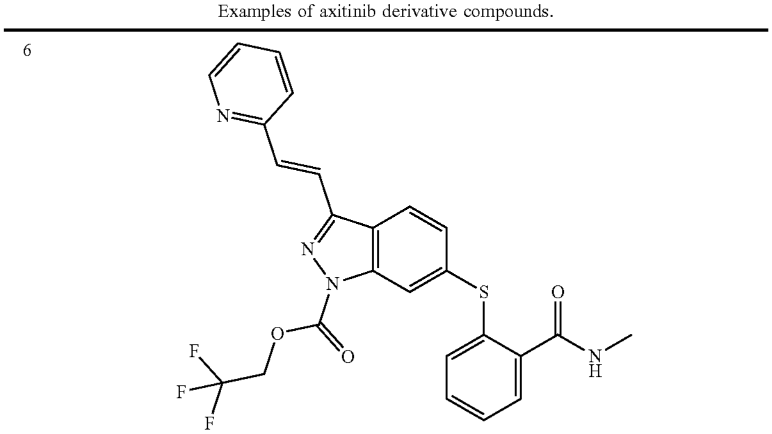 |
| 7 | 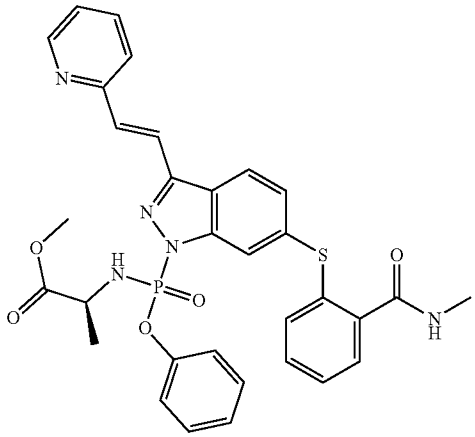 [SMILES: CNC(=O)c1ccccc1Sc1ccc2c(/C=C/c3ccccn3)nn(P(=O)(N[C@@H](C)C(=O)OC)Oc3ccccc3)c2c1] |
| 8 | 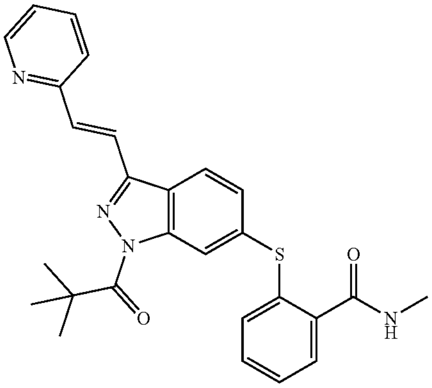 [SMILES: CNC(=O)c1ccccc1Sc1ccc2c(/C=C/c3ccccn3)nn(C(=O)C(C)(C)C)c2c1] |
| 9 | 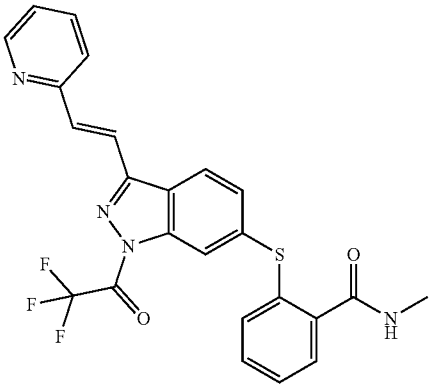 [SMILES: CNC(=O)c1ccccc1Sc1ccc2c(/C=C/c3ccccn3)nn(C(=O)C(F)(F)F)c2c1] |

TABLE 1-continued
| Examples of axitinib derivative compounds. |
| --- |
10
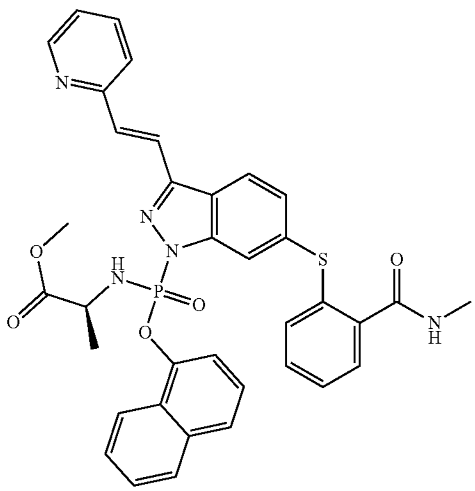 [SMILES: CNC(=O)c1ccccc1Sc1ccc2c(/C=C/c3ccccn3)nn(P(=O)(N[C@@H](C)C(=O)OC)Oc3cccc4ccccc34)c2c1]
11
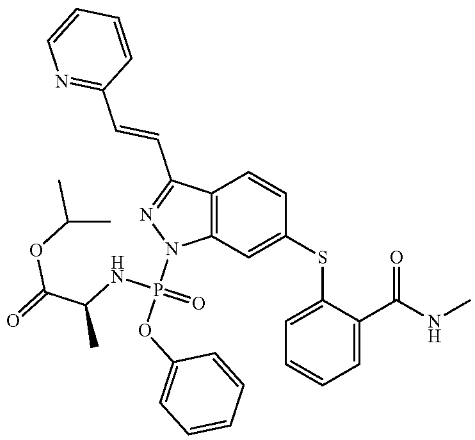 [SMILES: CNC(=O)c1ccccc1Sc1ccc2c(/C=C/c3ccccn3)nn(P(=O)(N[C@@H](C)C(=O)OC(C)C)Oc3ccccc3)c2c1]
12
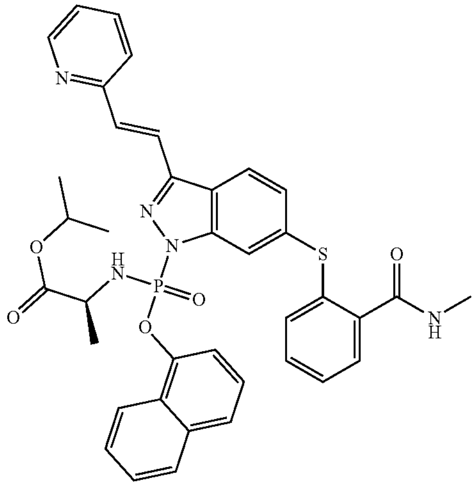 [SMILES: CNC(=O)c1ccccc1Sc1ccc2c(/C=C/c3ccccn3)nn(P(=O)(N[C@@H](C)C(=O)OC(C)C)Oc3cccc4ccccc34)c2c1]

TABLE 1-continued
| Examples of axitinib derivative compounds. | |
|---|---|
| 13 | 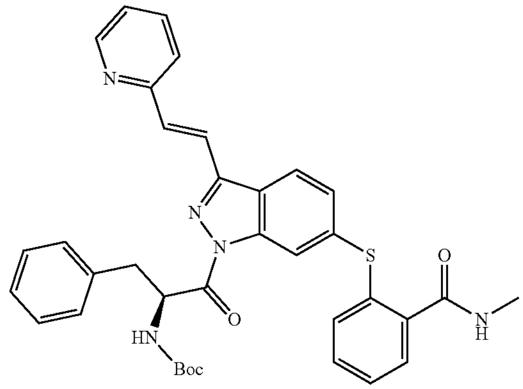 [SMILES: CNC(=O)c1ccccc1Sc1ccc2c(/C=C/c3ccccn3)nn(C(=O)[C@H](Cc3ccccc3)NC(=O)OC(C)(C)C)c2c1] |
| 14 | 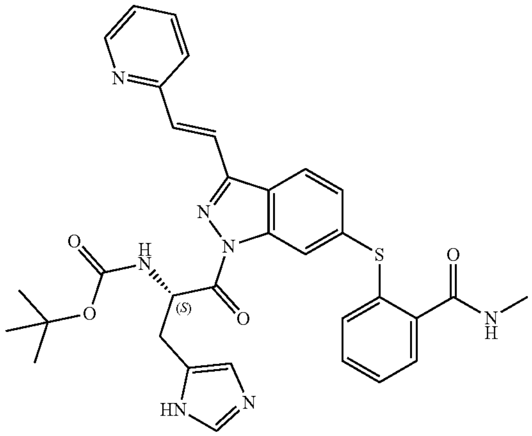 |
| 15 | 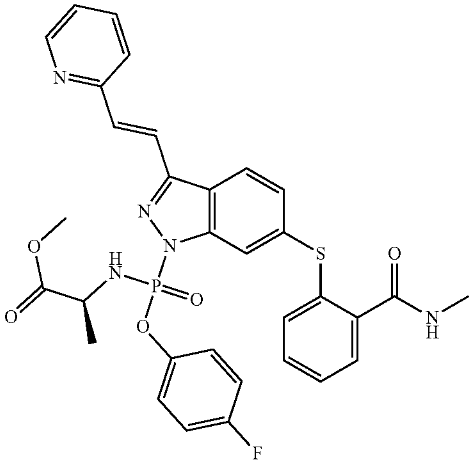 [SMILES: CNC(=O)c1ccccc1Sc1ccc2c(/C=C/c3ccccn3)nn(P(=O)(N[C@@H](C)C(=O)OC)Oc3ccc(F)cc3)c2c1] |

TABLE 1-continued
| Examples of axitinib derivative compounds. | |
|---|---|
| 16 | 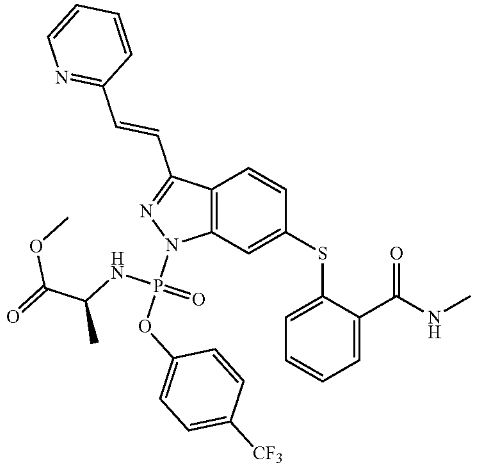 [SMILES: CNC(=O)c1ccccc1Sc1ccc2c(/C=C/c3ccccn3)nn(P(=O)(N[C@@H](C)C(=O)OC)Oc3ccc(C(F)(F)F)cc3)c2c1] |
| 17 | 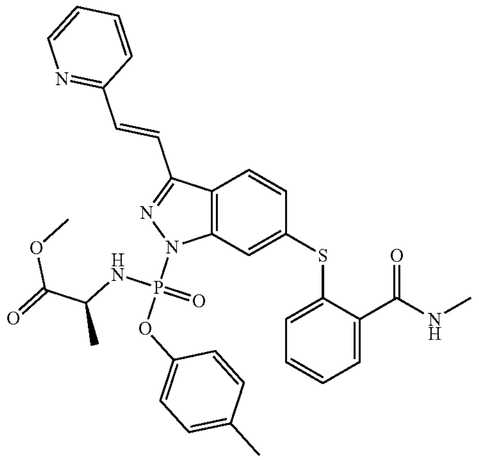 [SMILES: CNC(=O)c1ccccc1Sc1ccc2c(/C=C/c3ccccn3)nn(P(=O)(N[C@@H](C)C(=O)OC)Oc3ccc(C)cc3)c2c1] |
| 18 | 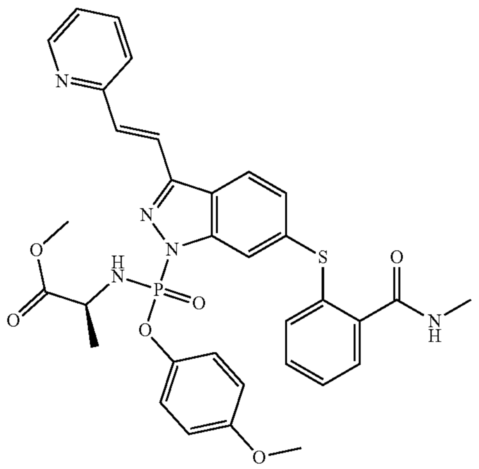 [SMILES: CNC(=O)c1ccccc1Sc1ccc2c(/C=C/c3ccccn3)nn(P(=O)(N[C@@H](C)C(=O)OC)Oc3ccc(OC)cc3)c2c1] |

TABLE 1-continued
| Examples of axitinib derivative compounds. | |
|---|---|
| 19 | 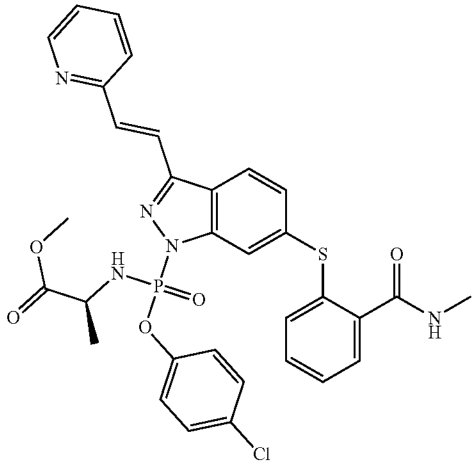 [SMILES: CNC(=O)c1ccccc1Sc1ccc2c(/C=C/c3ccccn3)nn(P(=O)(N[C@@H](C)C(=O)OC)Oc3ccc(Cl)cc3)c2c1] |
| 20 | 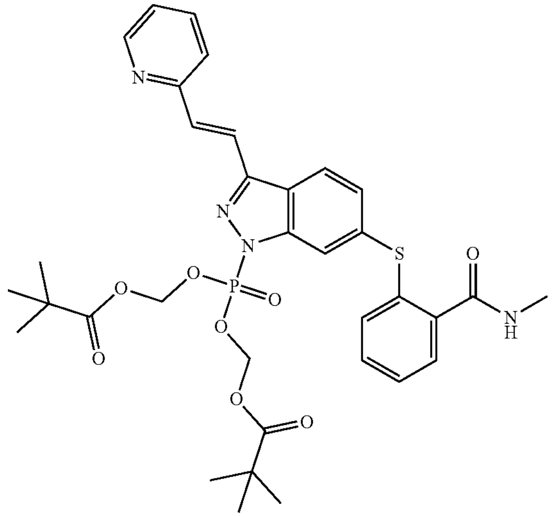 [SMILES: CNC(=O)c1ccccc1Sc1ccc2c(/C=C/c3ccccn3)nn(P(=O)(OCOC(=O)C(C)(C)C)OCOC(=O)C(C)(C)C)c2c1] |
| 21 | 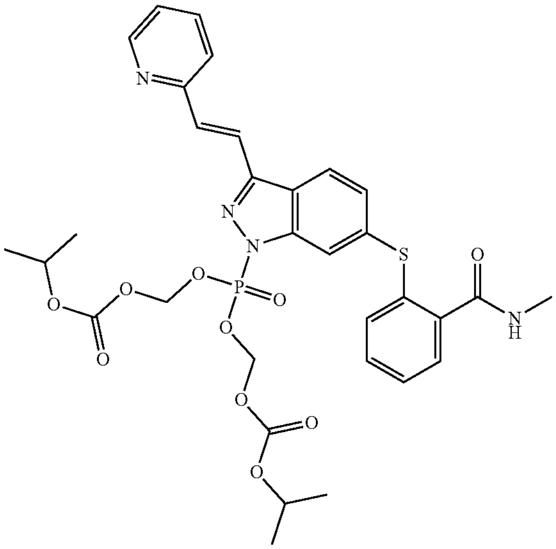 [SMILES: CNC(=O)c1ccccc1Sc1ccc2c(/C=C/c3ccccn3)nn(P(=O)(OCOC(=O)OC(C)C)OCOC(=O)OC(C)C)c2c1] |

TABLE 1-continued
| Examples of axitinib derivative compounds. |
| --- |
22
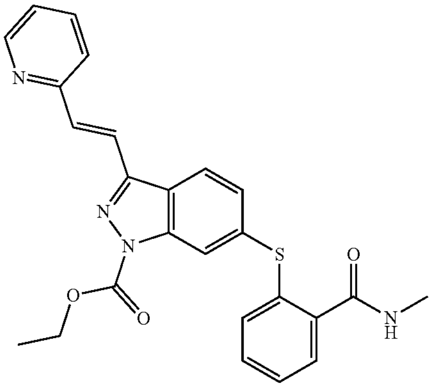 [SMILES: CCOC(=O)n1nc(/C=C/c2ccccn2)c2ccc(Sc3ccccc3C(=O)NC)cc21]
23
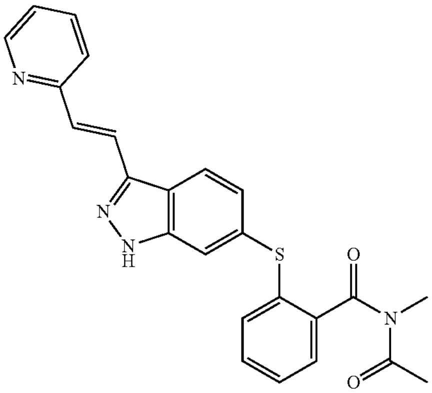 [SMILES: CC(=O)N(C)C(=O)c1ccccc1Sc1ccc2c(/C=C/c3ccccn3)n[nH]c2c1]
24
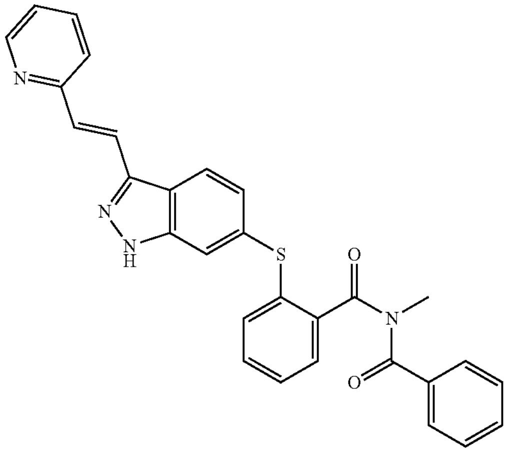 [SMILES: CN(C(=O)c1ccccc1)C(=O)c1ccccc1Sc1ccc2c(/C=C/c3ccccn3)n[nH]c2c1]

TABLE 1-continued
| Examples of axitinib derivative compounds. |
| --- |
25
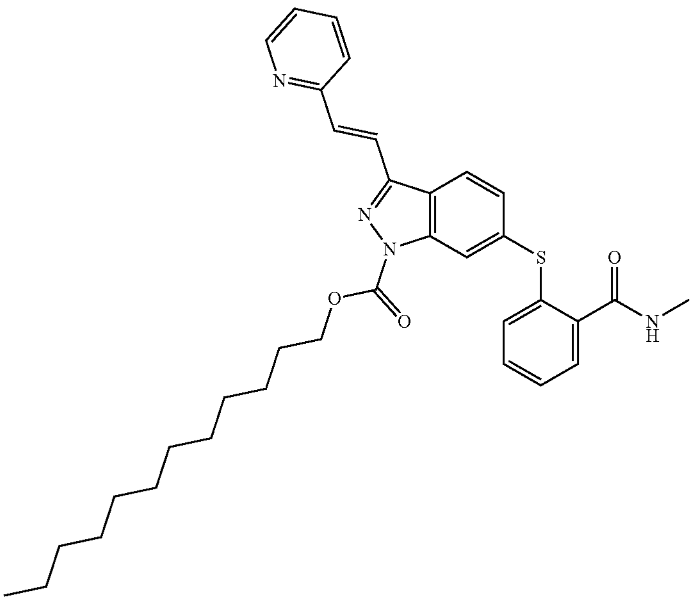 [SMILES: CCCCCCCCCCCCOC(=O)n1nc(/C=C/c2ccccn2)c2ccc(Sc3ccccc3C(=O)NC)cc21]
26
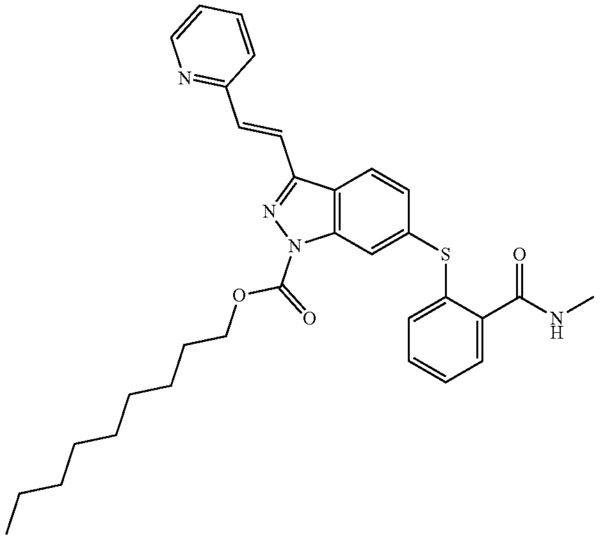 [SMILES: CCCCCCCCCOC(=O)n1nc(/C=C/c2ccccn2)c2ccc(Sc3ccccc3C(=O)NC)cc21]
27
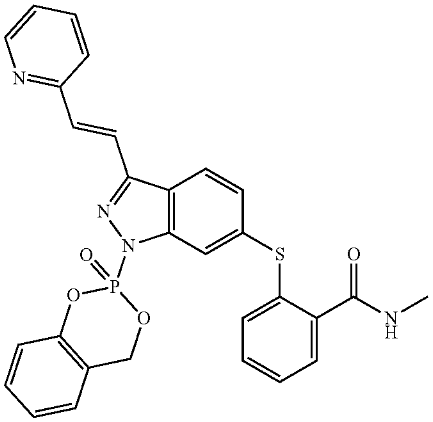 [SMILES: CNC(=O)c1ccccc1Sc1ccc2c(/C=C/c3ccccn3)nn(P3(=O)OCc4ccccc4O3)c2c1]

TABLE 1-continued
| Examples of axitinib derivative compounds. | |
|---|---|
| 28 | 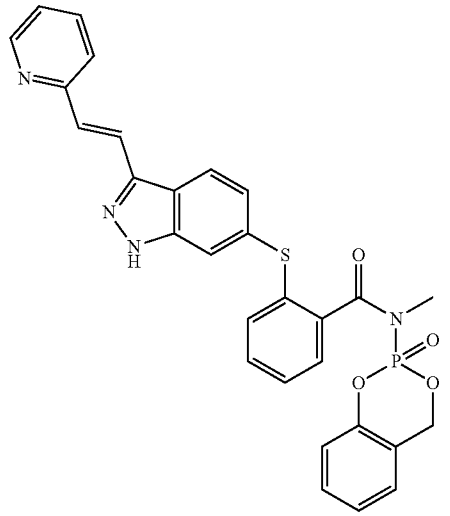 [SMILES: CN(C(=O)c1ccccc1Sc1ccc2c(/C=C/c3ccccn3)n[nH]c2c1)P1(=O)OCc2ccccc2O1] |
| 29 | 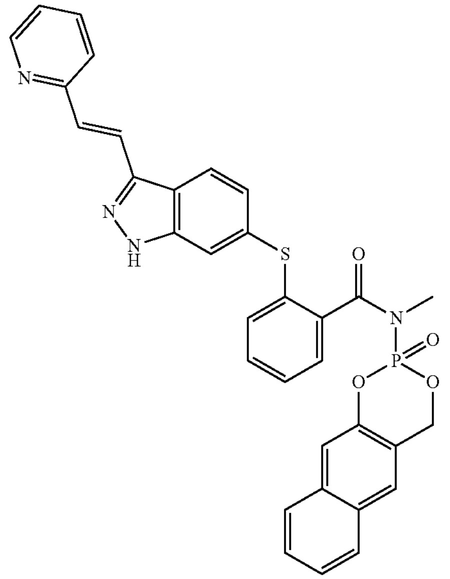 [SMILES: CN(C(=O)c1ccccc1Sc1ccc2c(/C=C/c3ccccn3)n[nH]c2c1)P1(=O)OCc2cc3ccccc3cc2O1] |
| 30 | 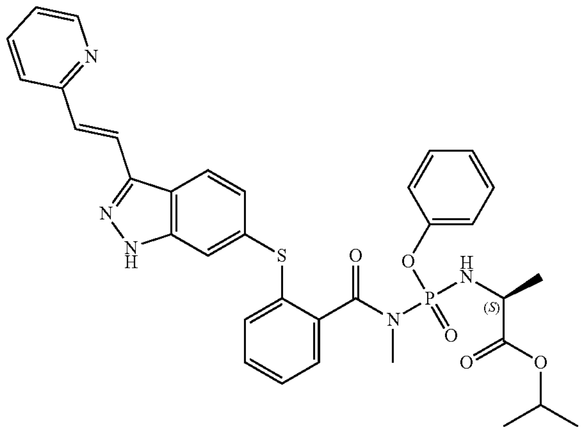 |

TABLE 1-continued
| Examples of axitinib derivative compounds. | |
|---|---|
| 31 | 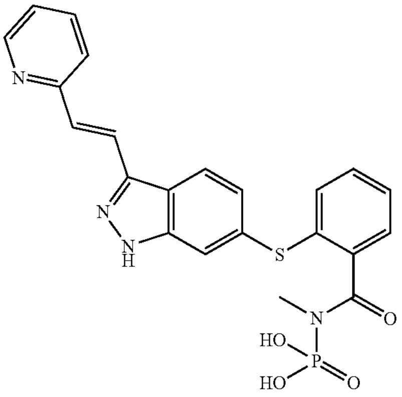 [SMILES: CN(C(=O)c1ccccc1Sc1ccc2c(/C=C/c3ccccn3)n[nH]c2c1)P(=O)(O)O] |
| 32 | 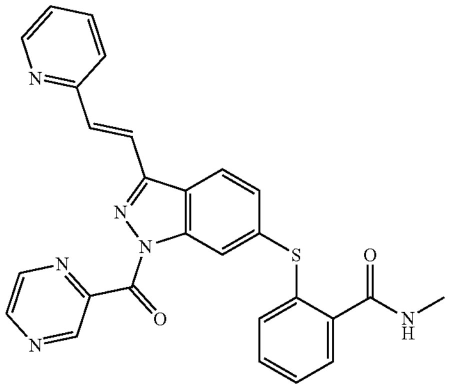 [SMILES: CNC(=O)c1ccccc1Sc1ccc2c(/C=C/c3ccccn3)nn(C(=O)c3cnccn3)c2c1] |
| 33 | 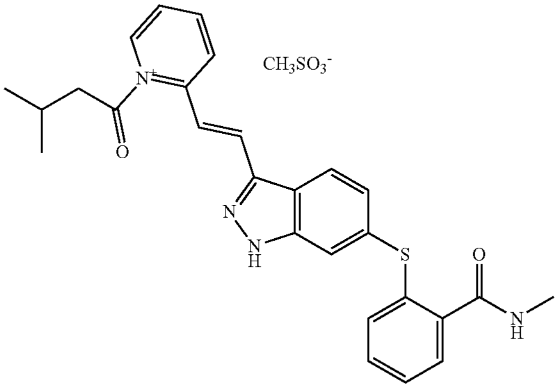 |

TABLE 1-continued
| Examples of axitinib derivative compounds. |
| --- |
34
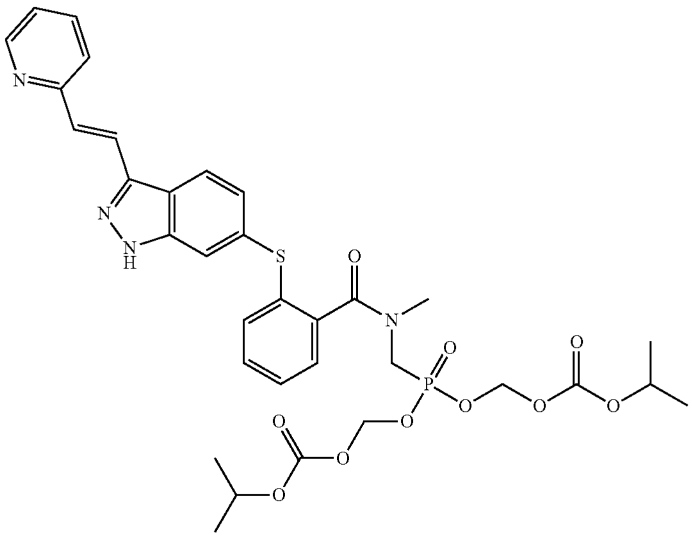 [SMILES: CC(C)OC(=O)OCOP(=O)(CN(C)C(=O)c1ccccc1Sc1ccc2c(/C=C/c3ccccn3)n[nH]c2c1)OCOC(=O)OC(C)C]
35
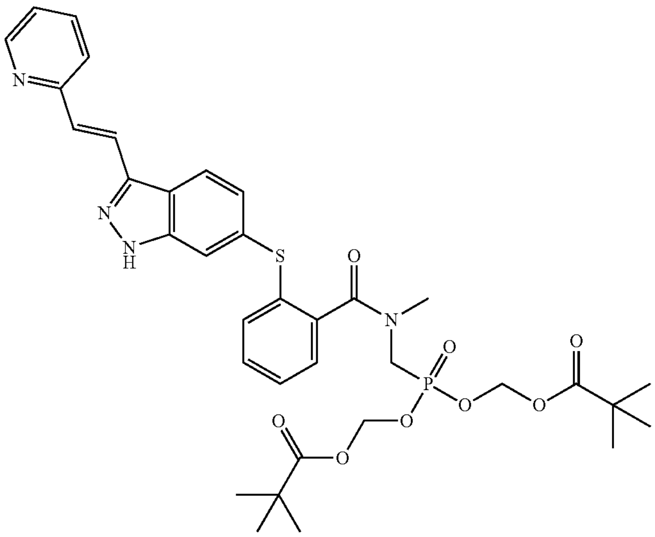 [SMILES: CN(CP(=O)(OCOC(=O)C(C)(C)C)OCOC(=O)C(C)(C)C)C(=O)c1ccccc1Sc1ccc2c(/C=C/c3ccccn3)n[nH]c2c1]

TABLE 1-continued
| Examples of axitinib derivative compounds. | |
|---|---|
| 36 | 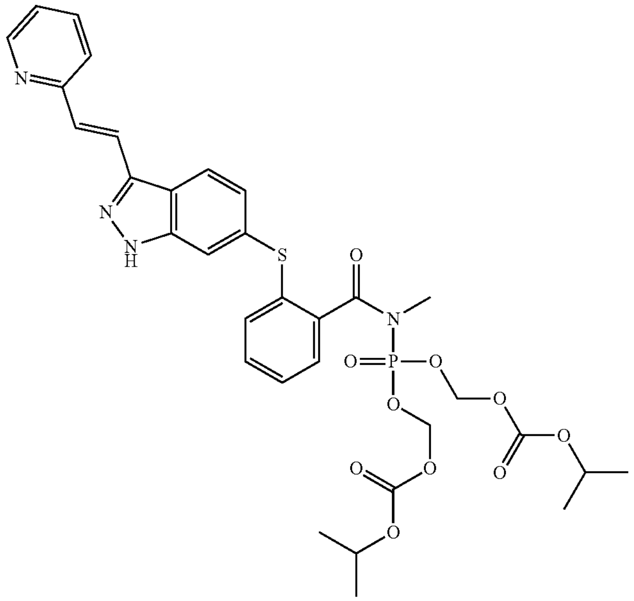 [SMILES: CC(C)OC(=O)OCOP(=O)(OCOC(=O)OC(C)C)N(C)C(=O)c1ccccc1Sc1ccc2c(/C=C/c3ccccn3)n[nH]c2c1] |
| 37 | 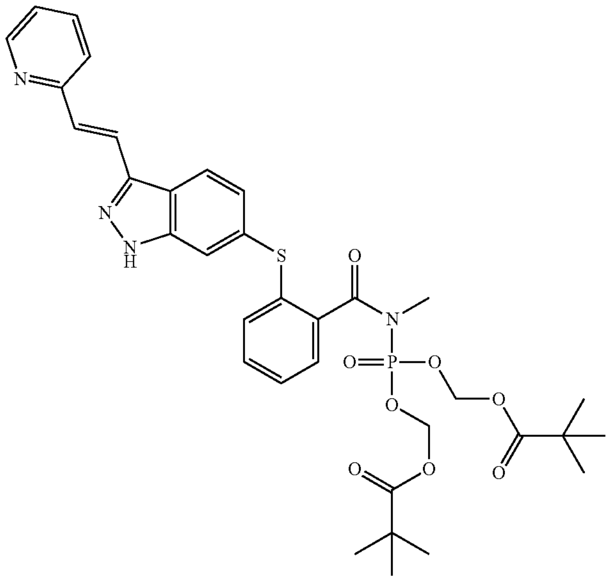 [SMILES: CN(C(=O)c1ccccc1Sc1ccc2c(/C=C/c3ccccn3)n[nH]c2c1)P(=O)(OCOC(=O)C(C)(C)C)OCOC(=O)C(C)(C)C] |

TABLE 1-continued
| Examples of axitinib derivative compounds. |
| --- |
38
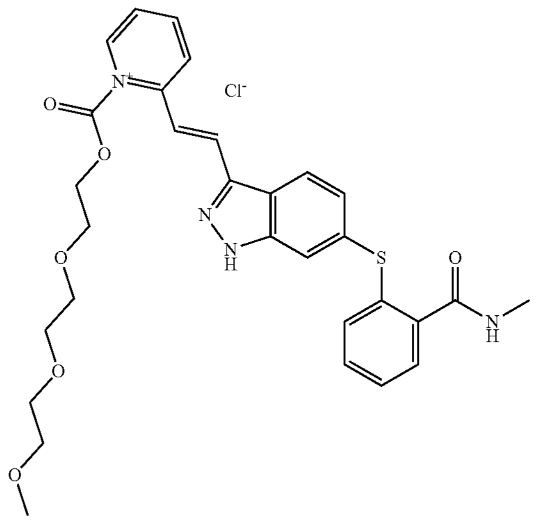 [SMILES: CNC(=O)c1ccccc1Sc1ccc2c(/C=C/c3cccc[n+]3C(=O)OCCOCCOCCOC)n[nH]c2c1 ; [Cl-]]
39
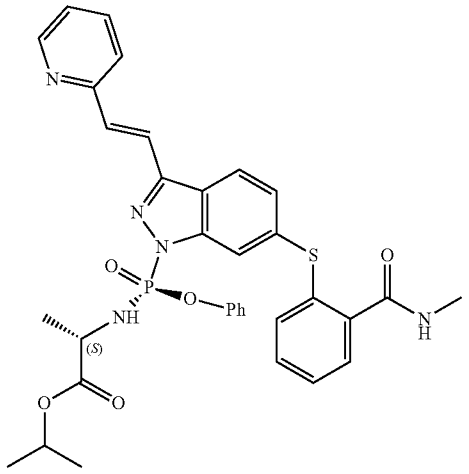
40
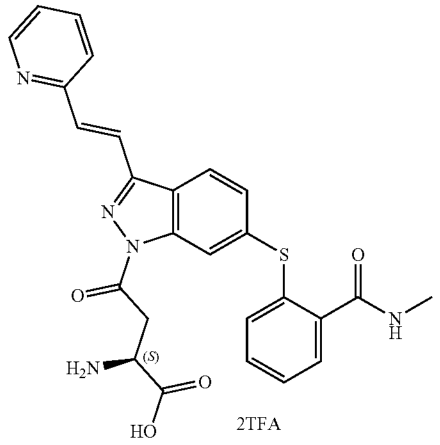

TABLE 1-continued
| Examples of axitinib derivative compounds. |
|---|
| 41 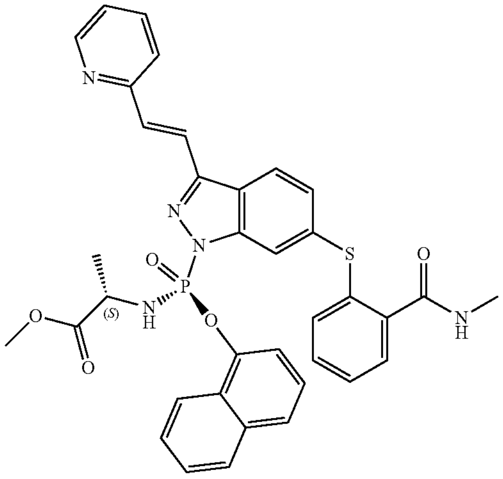 |
| 42 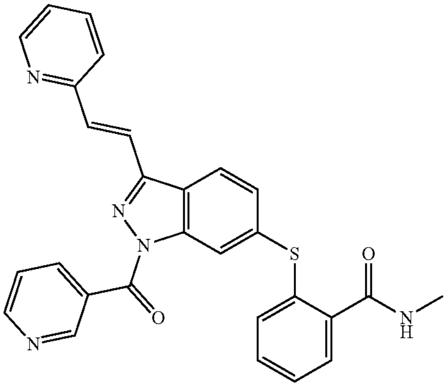 [SMILES: CNC(=O)c1ccccc1Sc1ccc2c(/C=C/c3ccccn3)nn(C(=O)c3cccnc3)c2c1] |
| 43 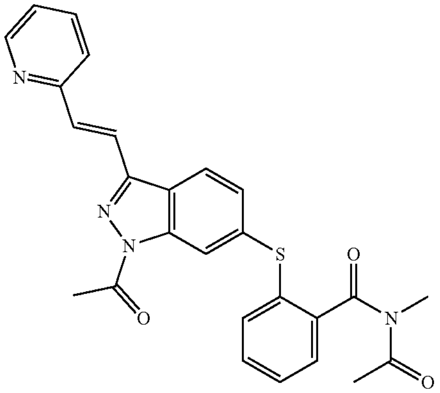 [SMILES: CC(=O)N(C)C(=O)c1ccccc1Sc1ccc2c(/C=C/c3ccccn3)nn(C(C)=O)c2c1] |

TABLE 1-continued
| Examples of axitinib derivative compounds. |
| --- |
| 44 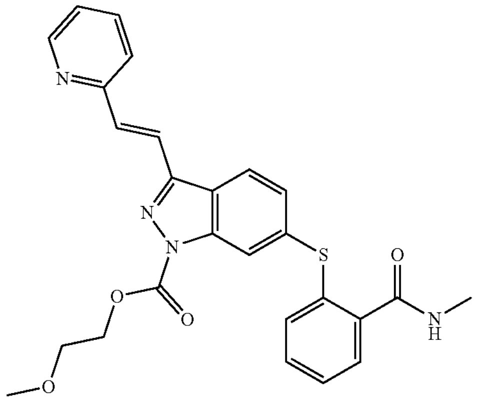 |
| 45 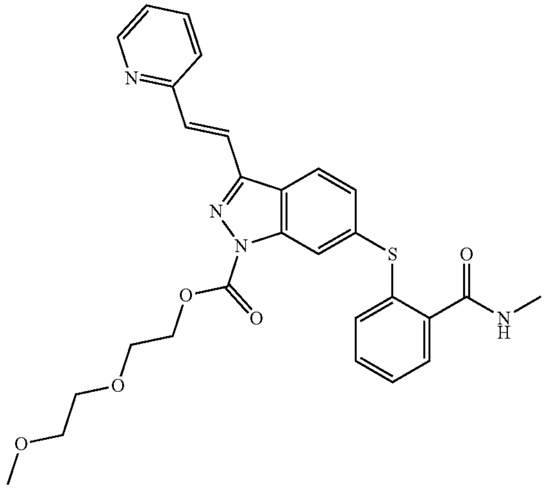 |
| 46 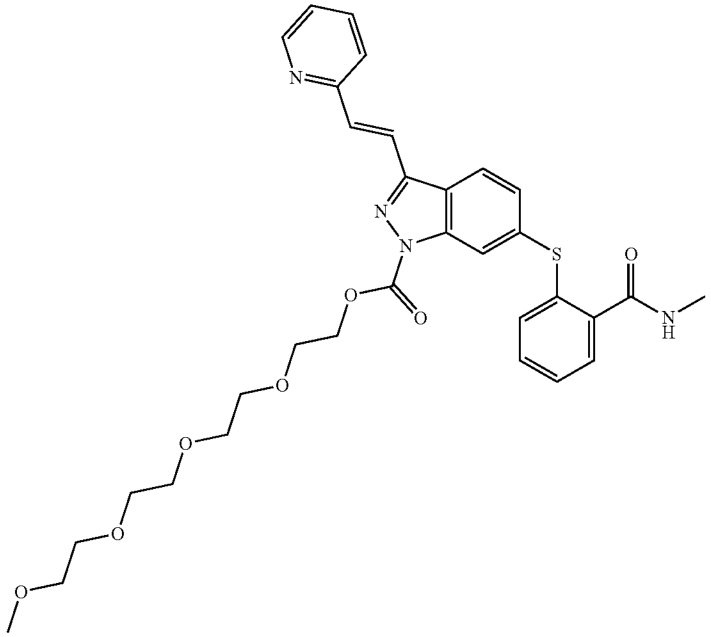 |

TABLE 1-continued
| Examples of axitinib derivative compounds. |
| --- |
47
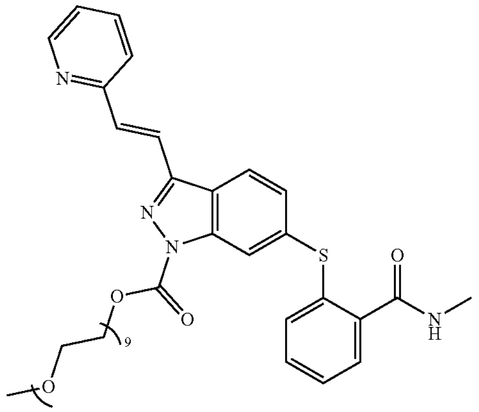
48
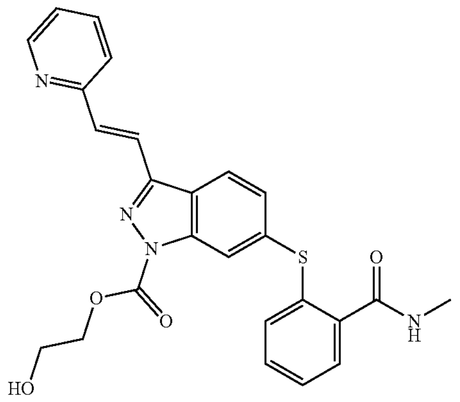 [SMILES: CNC(=O)c1ccccc1Sc1ccc2c(/C=C/c3ccccn3)nn(C(=O)OCCO)c2c1]
49
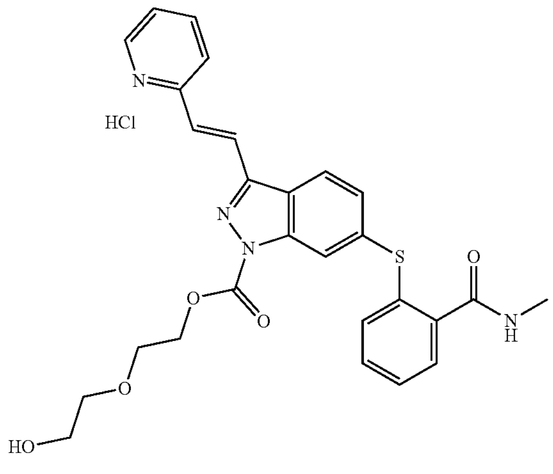 [SMILES: CNC(=O)c1ccccc1Sc1ccc2c(/C=C/c3ccccn3)nn(C(=O)OCCOCCO)c2c1 ; Cl]

TABLE 1-continued
| Examples of axitinib derivative compounds. | |
|---|---|
| 50 | 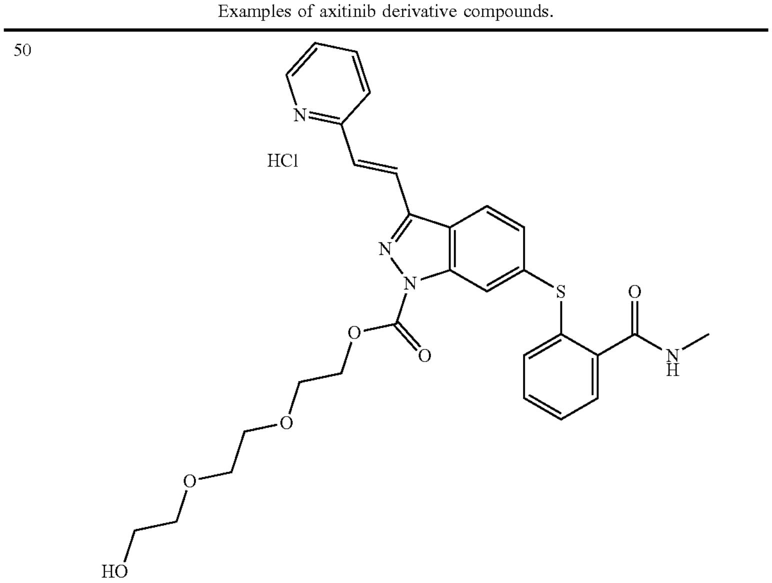 |
| 51 | 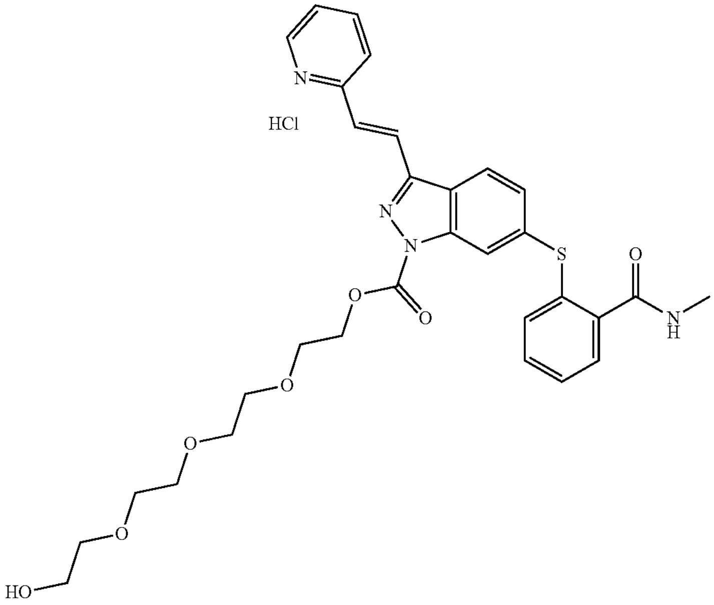 [SMILES: CNC(=O)c1ccccc1Sc1ccc2c(/C=C/c3ccccn3)nn(C(=O)OCCOCCOCCOCCO)c2c1 ; Cl] |
| 52 | 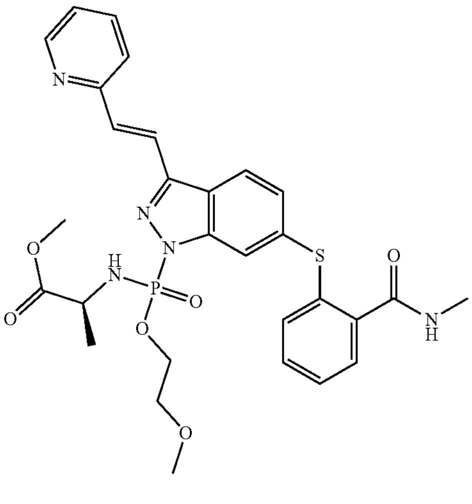 [SMILES: CNC(=O)c1ccccc1Sc1ccc2c(/C=C/c3ccccn3)nn(P(=O)(N[C@@H](C)C(=O)OC)OCCOC)c2c1] |

TABLE 1-continued
| Examples of axitinib derivative compounds. |
| --- |
53
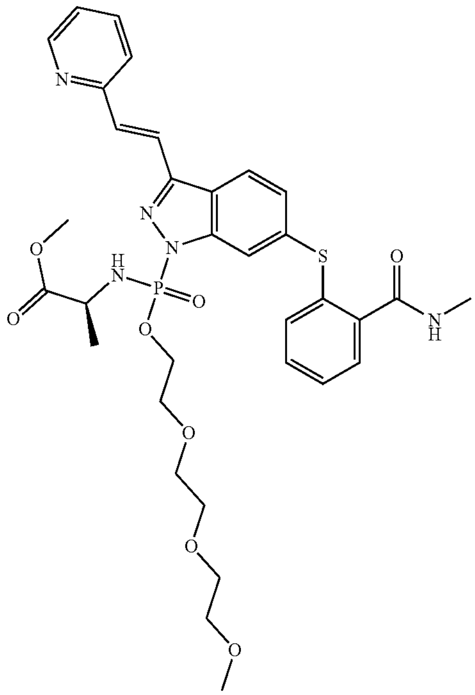 [SMILES: CNC(=O)c1ccccc1Sc1ccc2c(/C=C/c3ccccn3)nn(P(=O)(N[C@@H](C)C(=O)OC)OCCOCCOCCOC)c2c1]
54
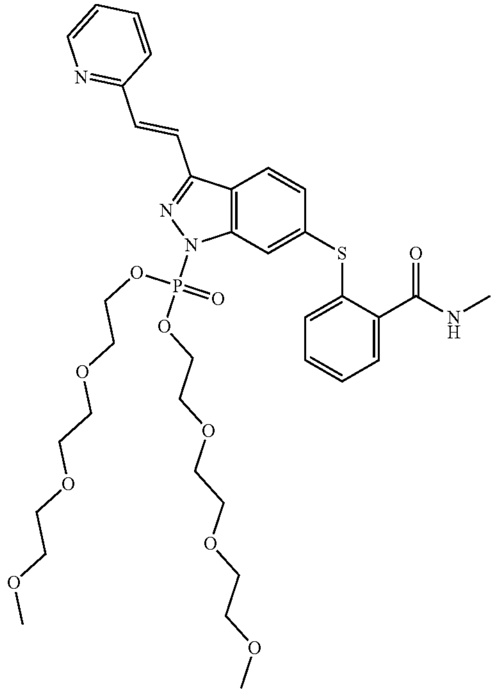 [SMILES: CNC(=O)c1ccccc1Sc1ccc2c(/C=C/c3ccccn3)nn(P(=O)(OCCOCCOCCOC)OCCOCCOCCOC)c2c1]

TABLE 1-continued
| Examples of axitinib derivative compounds. |
| --- |
| 55 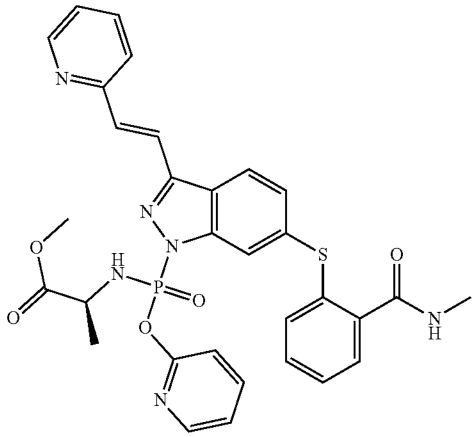 [SMILES: CNC(=O)c1ccccc1Sc1ccc2c(/C=C/c3ccccn3)nn(P(=O)(N[C@@H](C)C(=O)OC)Oc3ccccn3)c2c1] |
| 56 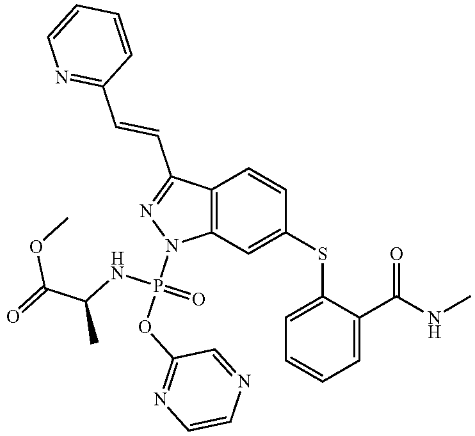 [SMILES: CNC(=O)c1ccccc1Sc1ccc2c(/C=C/c3ccccn3)nn(P(=O)(N[C@@H](C)C(=O)OC)Oc3cnccn3)c2c1] |
| 57 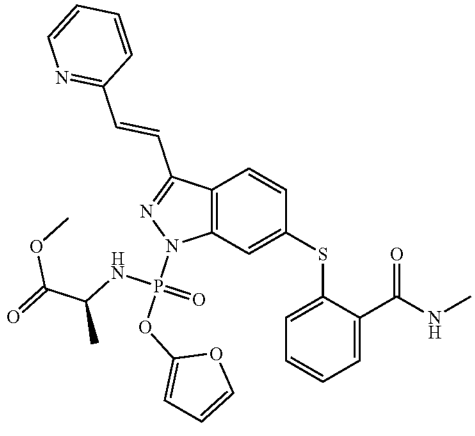 [SMILES: CNC(=O)c1ccccc1Sc1ccc2c(/C=C/c3ccccn3)nn(P(=O)(N[C@@H](C)C(=O)OC)Oc3ccco3)c2c1] |

TABLE 1-continued
| Examples of axitinib derivative compounds. | |
|---|---|
| 58 | 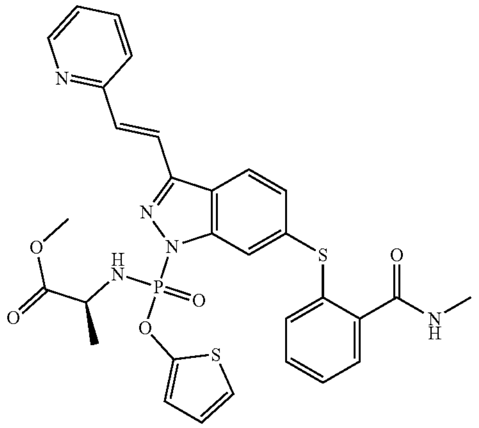 [SMILES: CNC(=O)c1ccccc1Sc1ccc2c(/C=C/c3ccccn3)nn(P(=O)(N[C@@H](C)C(=O)OC)Oc3cccs3)c2c1] |
| 59 | 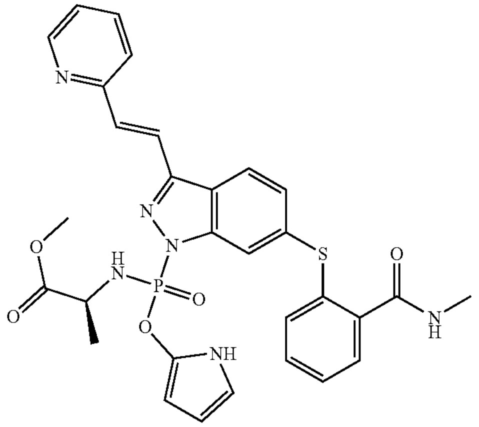 [SMILES: CNC(=O)c1ccccc1Sc1ccc2c(/C=C/c3ccccn3)nn(P(=O)(N[C@@H](C)C(=O)OC)Oc3ccc[nH]3)c2c1] |
| 60 | 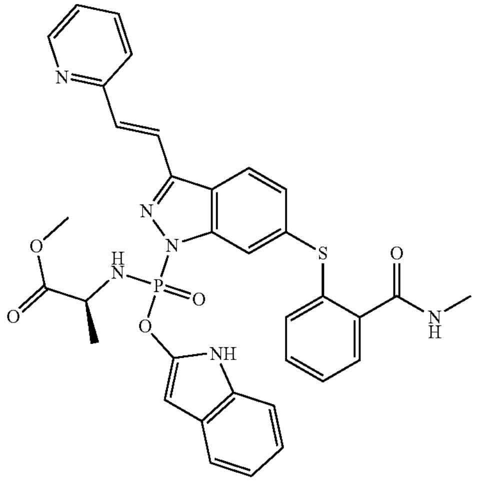 [SMILES: CNC(=O)c1ccccc1Sc1ccc2c(/C=C/c3ccccn3)nn(P(=O)(N[C@@H](C)C(=O)OC)Oc3cc4ccccc4[nH]3)c2c1] |

TABLE 1-continued
| Examples of axitinib derivative compounds. | |
|---|---|
| 61 | 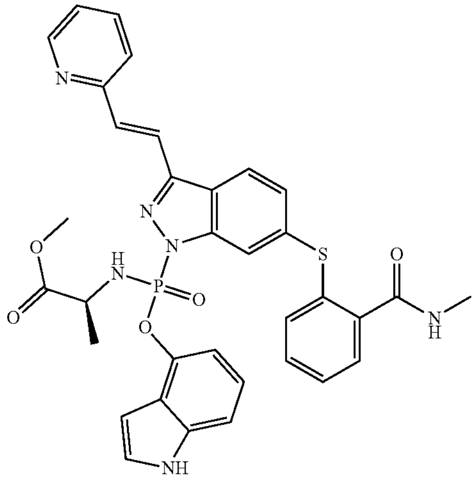 [SMILES: CNC(=O)c1ccccc1Sc1ccc2c(/C=C/c3ccccn3)nn(P(=O)(N[C@@H](C)C(=O)OC)Oc3cccc4[nH]ccc34)c2c1] |
| 62 | 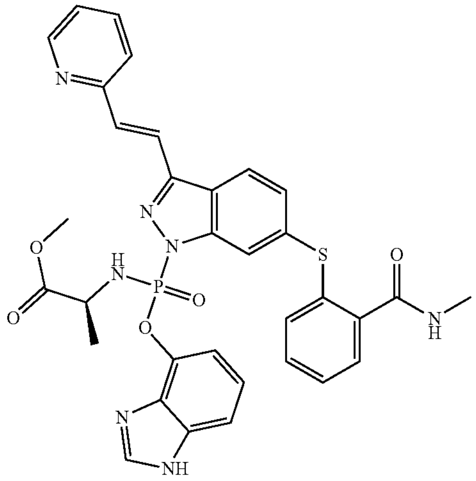 [SMILES: CNC(=O)c1ccccc1Sc1ccc2c(/C=C/c3ccccn3)nn(P(=O)(N[C@@H](C)C(=O)OC)Oc3cccc4[nH]cnc34)c2c1] |
| 63 | 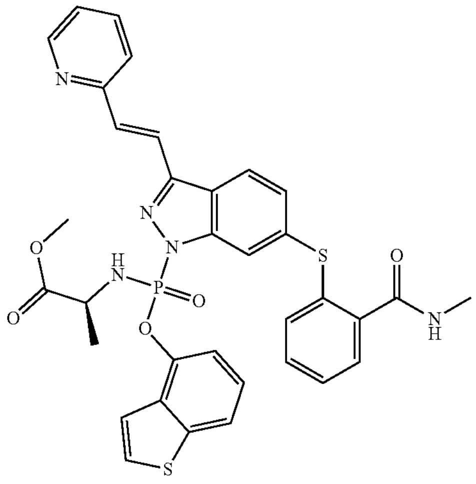 [SMILES: CNC(=O)c1ccccc1Sc1ccc2c(/C=C/c3ccccn3)nn(P(=O)(N[C@@H](C)C(=O)OC)Oc3cccc4sccc34)c2c1] |

TABLE 1-continued
| Examples of axitinib derivative compounds. |
| --- |
64
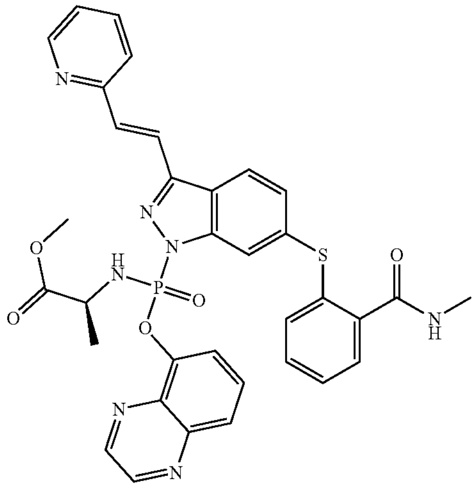 [SMILES: CNC(=O)c1ccccc1Sc1ccc2c(/C=C/c3ccccn3)nn(P(=O)(N[C@@H](C)C(=O)OC)Oc3cccc4nccnc34)c2c1]
65
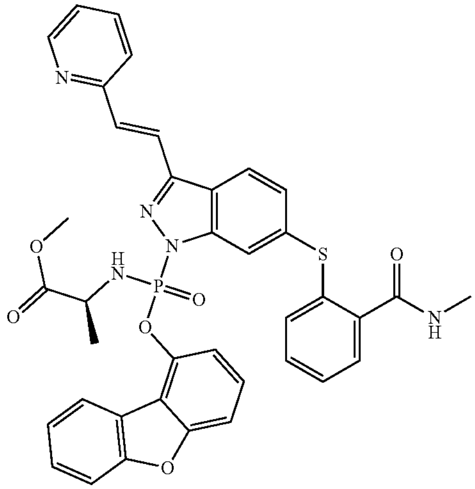 [SMILES: CNC(=O)c1ccccc1Sc1ccc2c(/C=C/c3ccccn3)nn(P(=O)(N[C@@H](C)C(=O)OC)Oc3cccc4oc5ccccc5c34)c2c1]
66
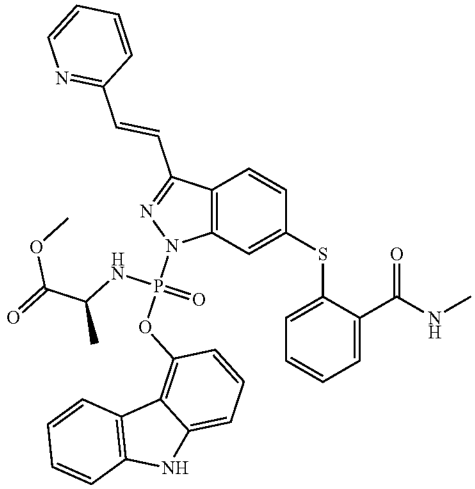 [SMILES: CNC(=O)c1ccccc1Sc1ccc2c(/C=C/c3ccccn3)nn(P(=O)(N[C@@H](C)C(=O)OC)Oc3cccc4[nH]c5ccccc5c34)c2c1]

TABLE 1-continued
| Examples of axitinib derivative compounds. |
|---|
| 67 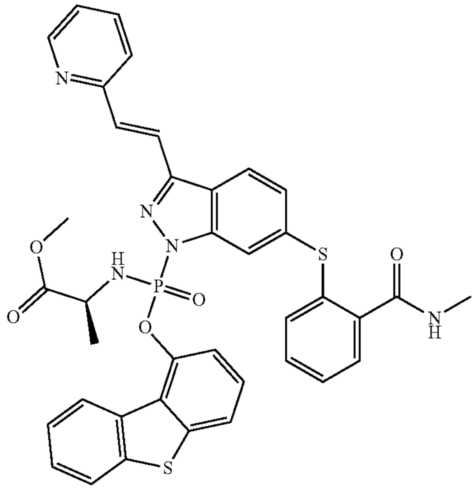 [SMILES: CNC(=O)c1ccccc1Sc1ccc2c(/C=C/c3ccccn3)nn(P(=O)(N[C@@H](C)C(=O)OC)Oc3cccc4sc5ccccc5c34)c2c1] |
| 68 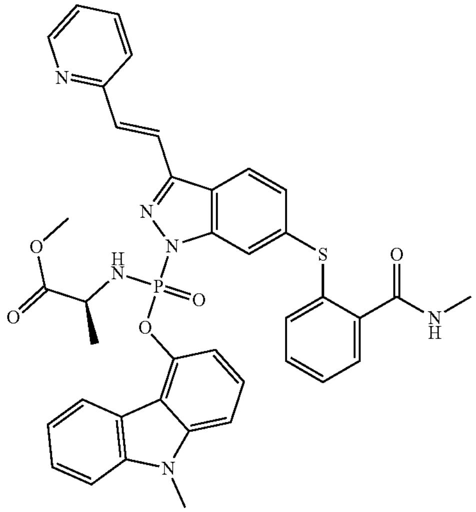 [SMILES: CNC(=O)c1ccccc1Sc1ccc2c(/C=C/c3ccccn3)nn(P(=O)(N[C@@H](C)C(=O)OC)Oc3cccc4c3c3ccccc3n4C)c2c1] |
| 69 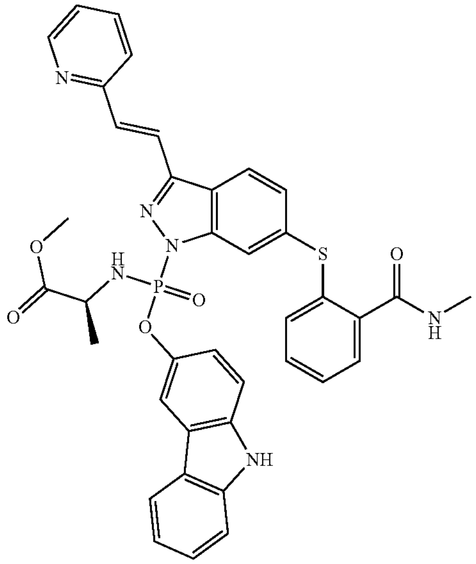 [SMILES: CNC(=O)c1ccccc1Sc1ccc2c(/C=C/c3ccccn3)nn(P(=O)(N[C@@H](C)C(=O)OC)Oc3ccc4[nH]c5ccccc5c4c3)c2c1] |

TABLE 1-continued
| Examples of axitinib derivative compounds. |
| --- |
70
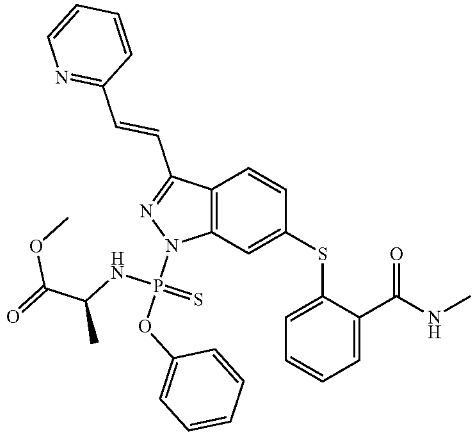
71
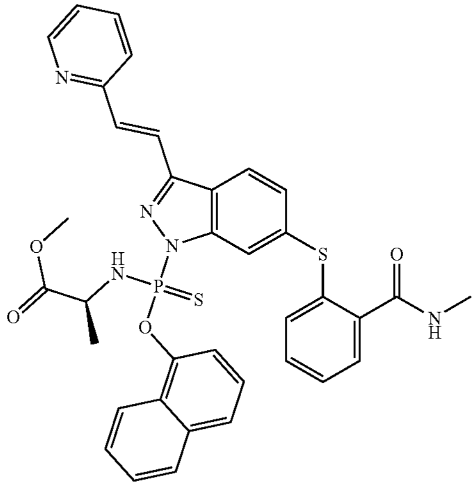 [SMILES: CNC(=O)c1ccccc1Sc1ccc2c(/C=C/c3ccccn3)nn(P(=S)(N[C@@H](C)C(=O)OC)Oc3cccc4ccccc34)c2c1]
72
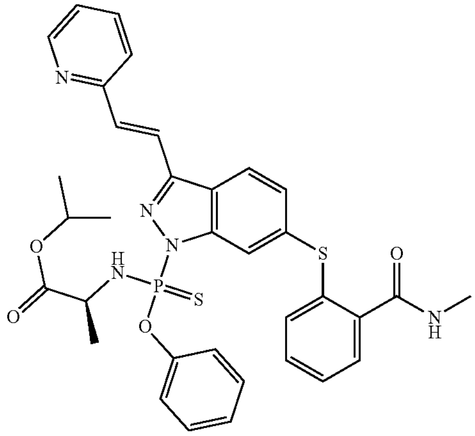 [SMILES: CNC(=O)c1ccccc1Sc1ccc2c(/C=C/c3ccccn3)nn(P(=S)(N[C@@H](C)C(=O)OC(C)C)Oc3ccccc3)c2c1]

TABLE 1-continued
| Examples of axitinib derivative compounds. | |
|---|---|
| 73 | 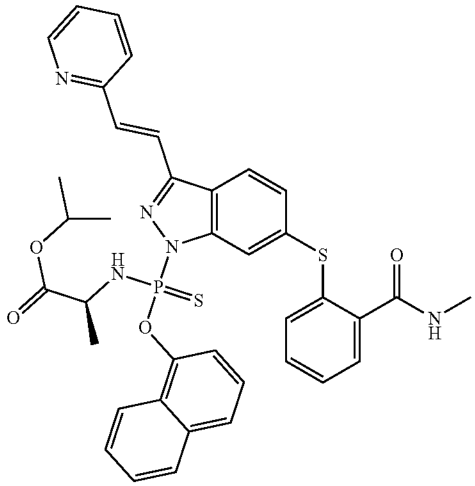 [SMILES: CNC(=O)c1ccccc1Sc1ccc2c(/C=C/c3ccccn3)nn(P(=S)(N[C@@H](C)C(=O)OC(C)C)Oc3cccc4ccccc34)c2c1] |
| 74 | 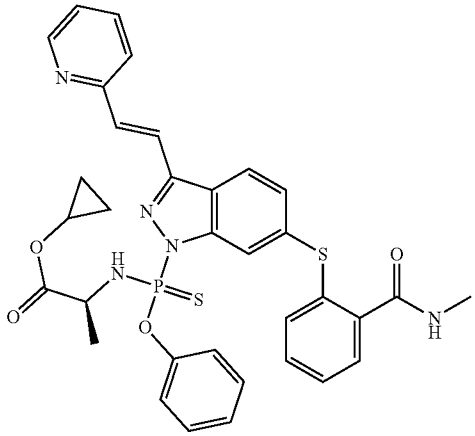 |
| 75 | 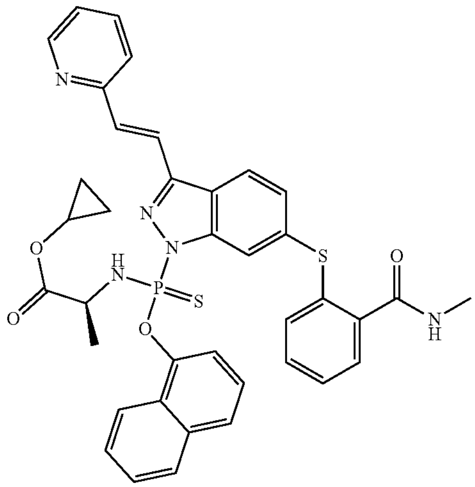 [SMILES: CNC(=O)c1ccccc1Sc1ccc2c(/C=C/c3ccccn3)nn(P(=S)(N[C@@H](C)C(=O)OC3CC3)Oc3cccc4ccccc34)c2c1] |

TABLE 1-continued
| Examples of axitinib derivative compounds. |
| --- |
| 76 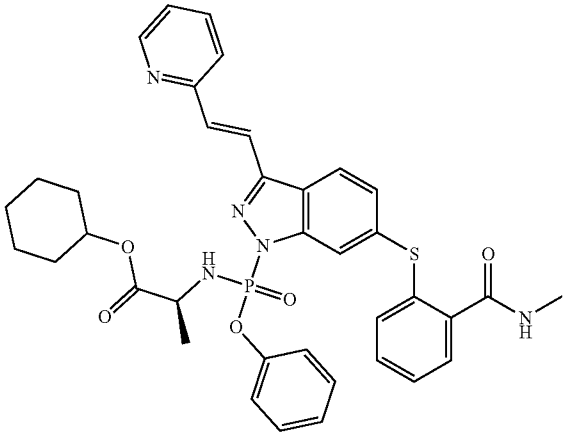 [SMILES: CNC(=O)c1ccccc1Sc1ccc2c(/C=C/c3ccccn3)nn(P(=O)(N[C@@H](C)C(=O)OC3CCCCC3)Oc3ccccc3)c2c1] |
| 77 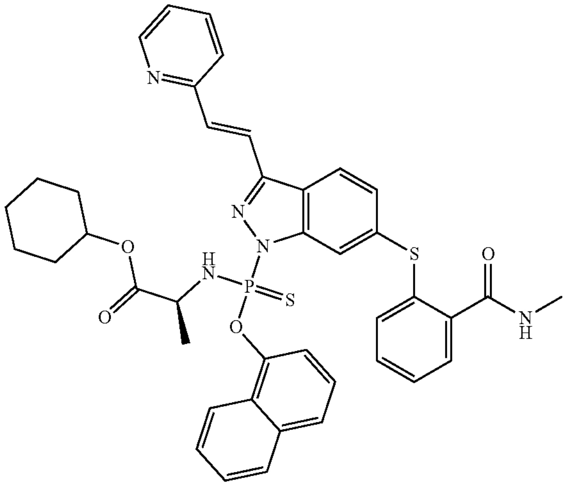 [SMILES: CNC(=O)c1ccccc1Sc1ccc2c(/C=C/c3ccccn3)nn(P(=S)(N[C@@H](C)C(=O)OC3CCCCC3)Oc3cccc4ccccc34)c2c1] |
| 78 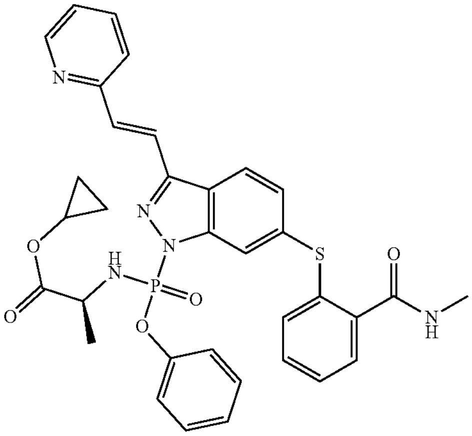 [SMILES: CNC(=O)c1ccccc1Sc1ccc2c(/C=C/c3ccccn3)nn(P(=O)(N[C@@H](C)C(=O)OC3CC3)Oc3ccccc3)c2c1] |

TABLE 1-continued
| Examples of axitinib derivative compounds. |
| --- |
79
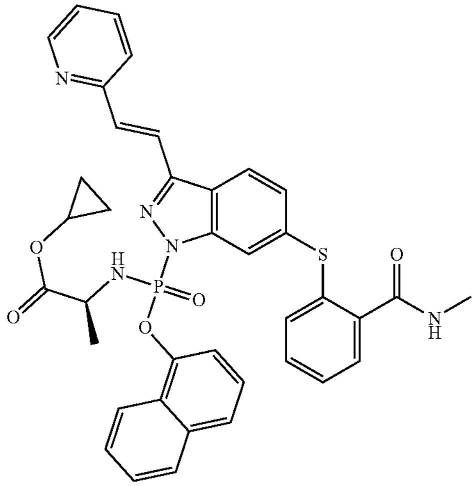 [SMILES: CNC(=O)c1ccccc1Sc1ccc2c(/C=C/c3ccccn3)nn(P(=O)(N[C@@H](C)C(=O)OC3CC3)Oc3cccc4ccccc34)c2c1]
80
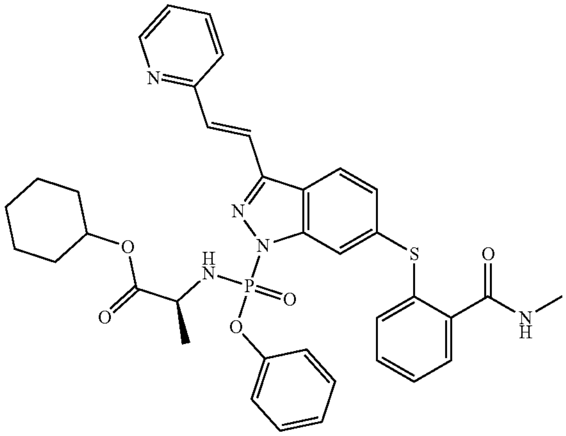 [SMILES: CNC(=O)c1ccccc1Sc1ccc2c(/C=C/c3ccccn3)nn(P(=O)(N[C@@H](C)C(=O)OC3CCCCC3)Oc3ccccc3)c2c1]
81
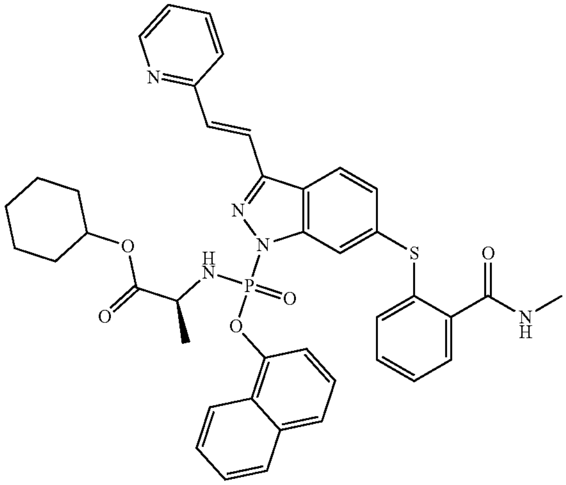

TABLE 1-continued
| Examples of axitinib derivative compounds. | |
|---|---|
| 82 | 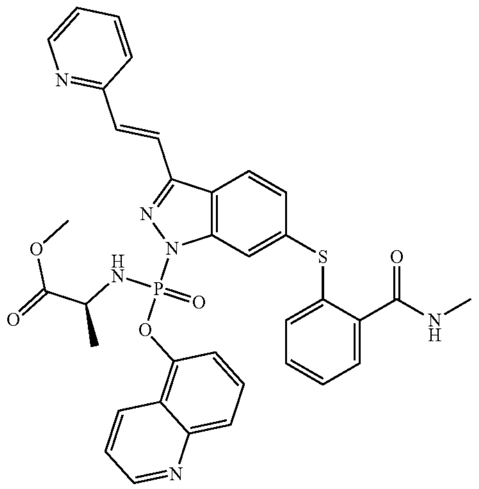 [SMILES: CNC(=O)c1ccccc1Sc1ccc2c(/C=C/c3ccccn3)nn(P(=O)(N[C@@H](C)C(=O)OC)Oc3cccc4ncccc34)c2c1] |
| 83 | 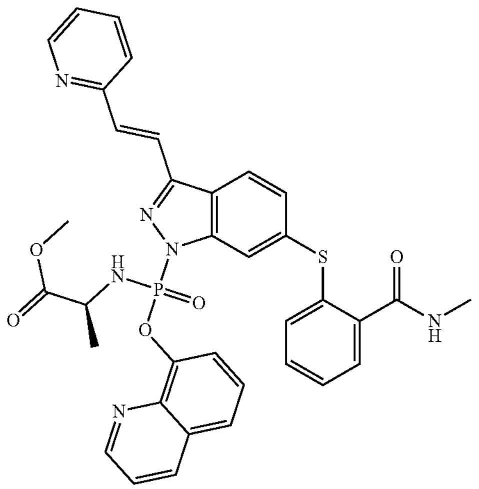 [SMILES: CNC(=O)c1ccccc1Sc1ccc2c(/C=C/c3ccccn3)nn(P(=O)(N[C@@H](C)C(=O)OC)Oc3cccc4cccnc34)c2c1] |
| 84 | 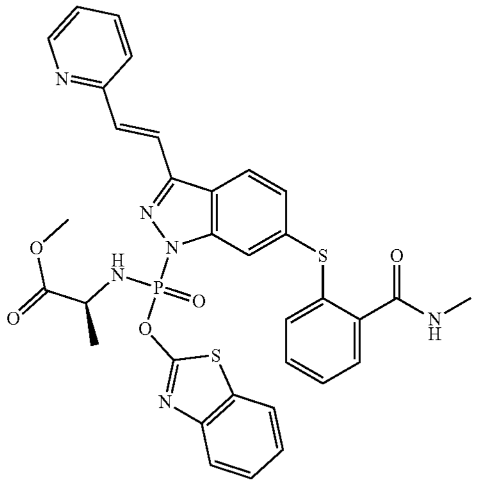 [SMILES: CNC(=O)c1ccccc1Sc1ccc2c(/C=C/c3ccccn3)nn(P(=O)(N[C@@H](C)C(=O)OC)Oc3nc4ccccc4s3)c2c1] |

TABLE 1-continued
| Examples of axitinib derivative compounds. |
|---|
85
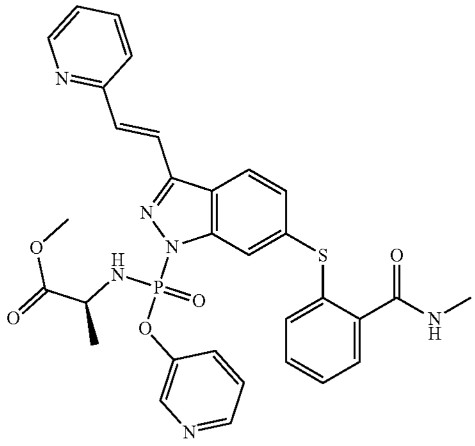 [SMILES: CNC(=O)c1ccccc1Sc1ccc2c(/C=C/c3ccccn3)nn(P(=O)(N[C@@H](C)C(=O)OC)Oc3cccnc3)c2c1]
86
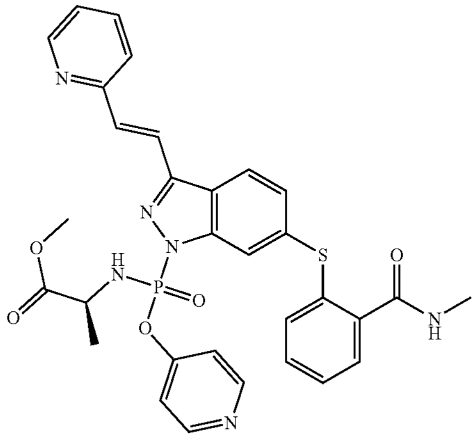 [SMILES: CNC(=O)c1ccccc1Sc1ccc2c(/C=C/c3ccccn3)nn(P(=O)(N[C@@H](C)C(=O)OC)Oc3ccncc3)c2c1]
87
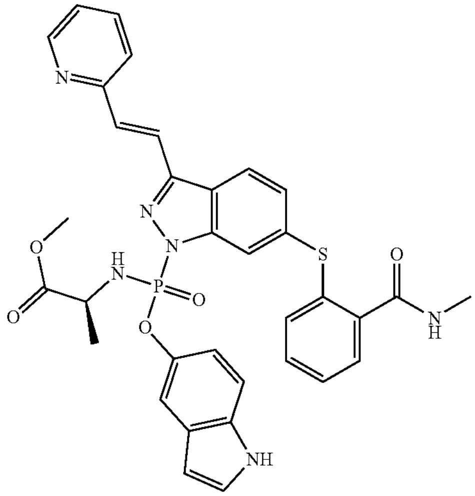 [SMILES: CNC(=O)c1ccccc1Sc1ccc2c(/C=C/c3ccccn3)nn(P(=O)(N[C@@H](C)C(=O)OC)Oc3ccc4[nH]ccc4c3)c2c1]

TABLE 1-continued
| Examples of axitinib derivative compounds. | |
|---|---|
| 88 | 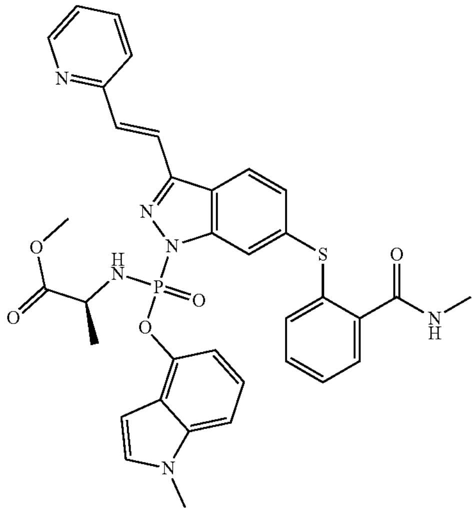 [SMILES: CNC(=O)c1ccccc1Sc1ccc2c(/C=C/c3ccccn3)nn(P(=O)(N[C@@H](C)C(=O)OC)Oc3cccc4c3ccn4C)c2c1] |
| 89 | 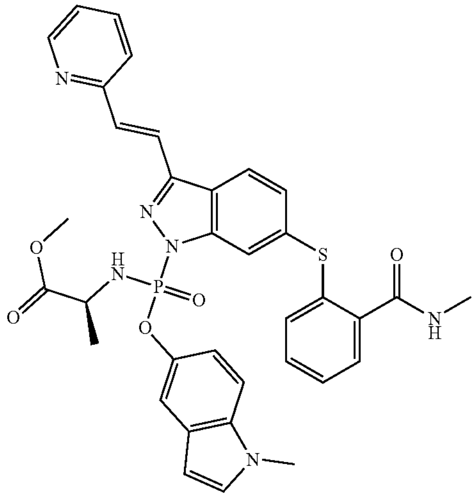 [SMILES: CNC(=O)c1ccccc1Sc1ccc2c(/C=C/c3ccccn3)nn(P(=O)(N[C@@H](C)C(=O)OC)Oc3ccc4c(ccn4C)c3)c2c1] |
| 90 | 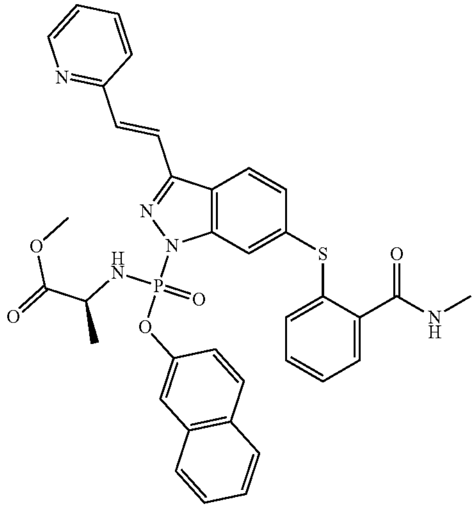 [SMILES: CNC(=O)c1ccccc1Sc1ccc2c(/C=C/c3ccccn3)nn(P(=O)(N[C@@H](C)C(=O)OC)Oc3ccc4ccccc4c3)c2c1] |

TABLE 1-continued
| Examples of axitinib derivative compounds. | |
|---|---|
| 91 | 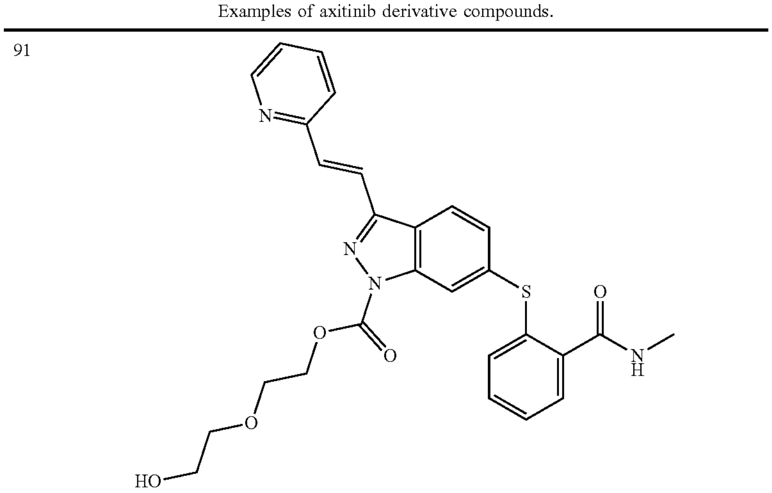 |
| 92 | 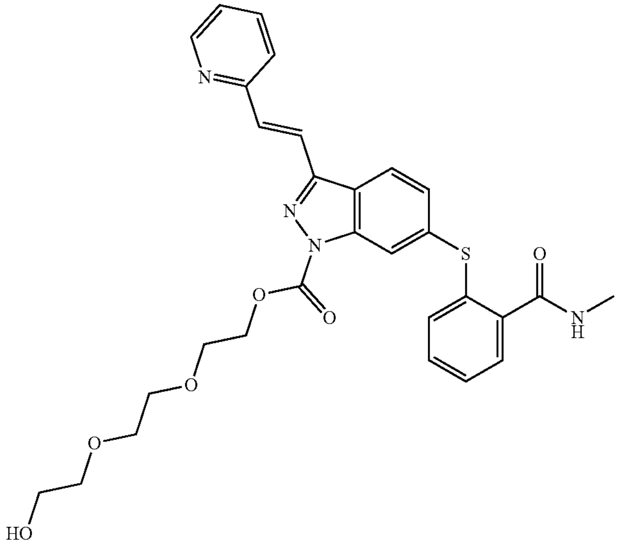 [SMILES: CNC(=O)c1ccccc1Sc1ccc2c(/C=C/c3ccccn3)nn(C(=O)OCCOCCOCCO)c2c1] |
| 93 | 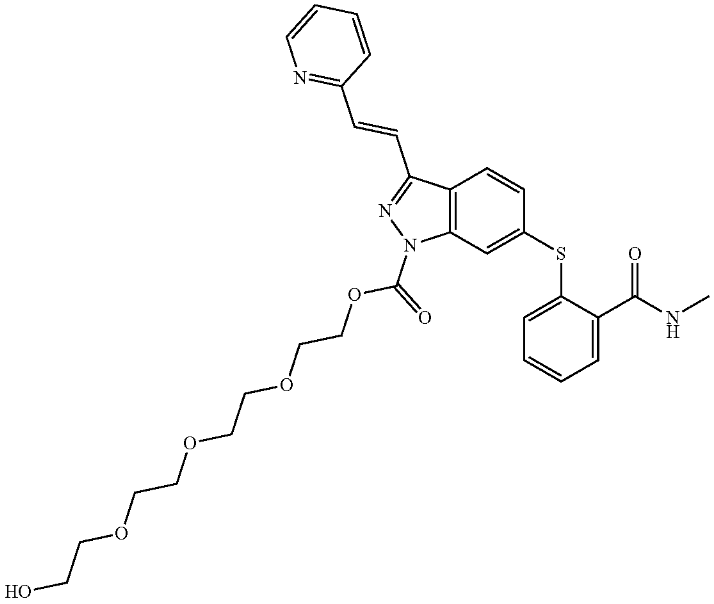 [SMILES: CNC(=O)c1ccccc1Sc1ccc2c(/C=C/c3ccccn3)nn(C(=O)OCCOCCOCCOCCO)c2c1] |

TABLE 1-continued
| Examples of axitinib derivative compounds. |
| --- |
94
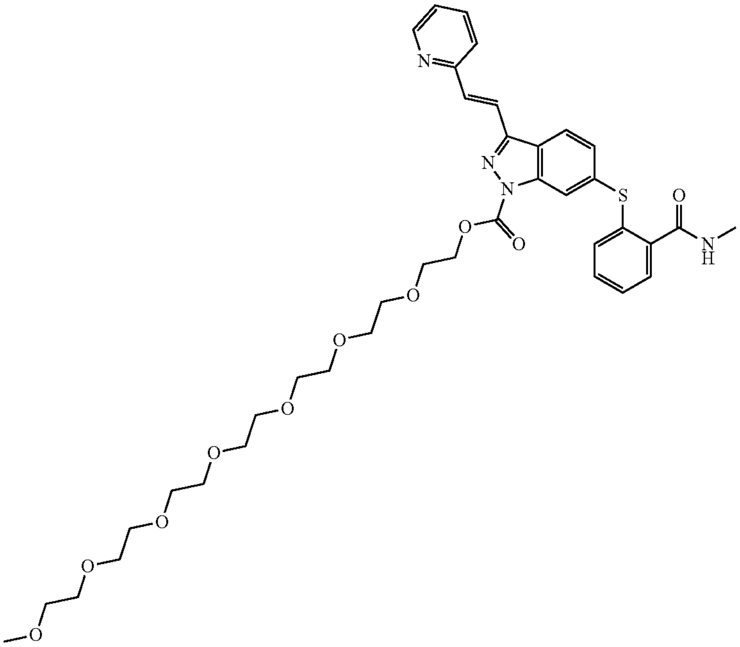
95
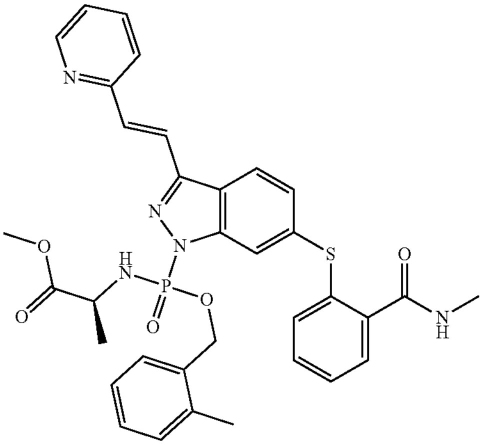
96
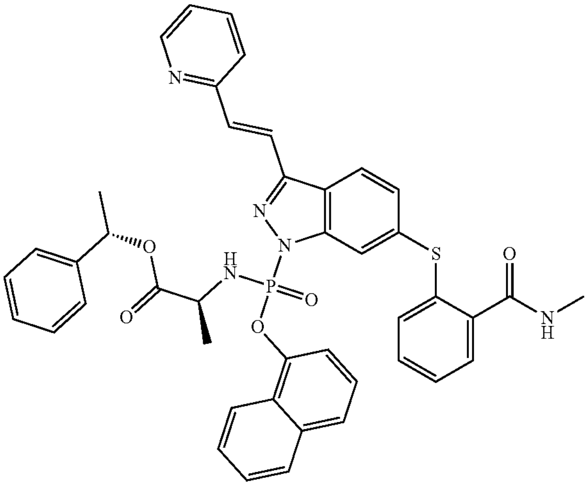 [SMILES: CNC(=O)c1ccccc1Sc1ccc2c(/C=C/c3ccccn3)nn(P(=O)(N[C@@H](C)C(=O)O[C@@H](C)c3ccccc3)Oc3cccc4ccccc34)c2c1]

TABLE 1-continued

Examples of axitinib derivative compounds.

97

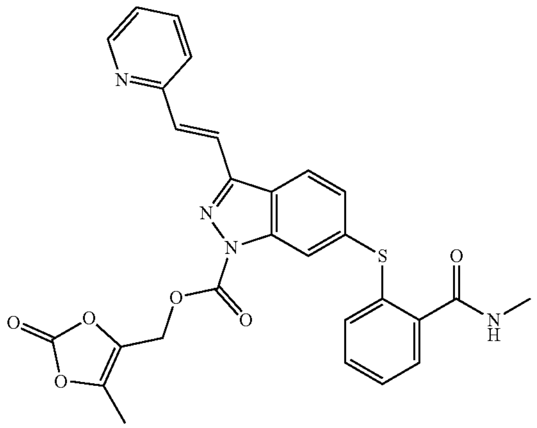 [SMILES: CNC(=O)c1ccccc1Sc1ccc2c(/C=C/c3ccccn3)nn(C(=O)OCc3oc(=O)oc3C)c2c1]

98

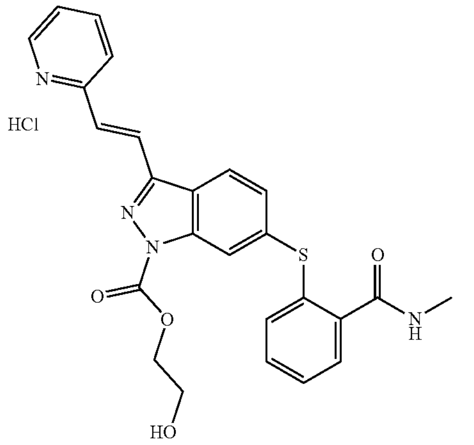 [SMILES: Cl ; CNC(=O)c1ccccc1Sc1ccc2c(/C=C/c3ccccn3)nn(C(=O)OCCO)c2c1]

In a second broad aspect, there are provided pharmaceutical compositions comprising a compound described herein, or a pharmaceutically acceptable salt thereof, and a pharmaceutically acceptable carrier. In some embodiments, there are provided pharmaceutical compositions comprising a compound of Formula I, II, or III, or a pharmaceutically acceptable salt thereof, and a pharmaceutically acceptable carrier.

In a third broad aspect, there are provided methods of inhibiting or modulating the activity of tyrosine kinases. In some embodiments, there are provided methods of treating disease states or conditions mediated by tyrosine kinases in a subject in need thereof comprising administering to the subject an effective amount of a compound and/or a pharmaceutical composition described herein. Non-limiting examples of disease states or conditions mediated by tyrosine kinases that may be treated according to methods provided herein include various tumors and cancers. Examples of tumors and cancers that may be treated include, without limitation, renal cell carcinoma (RCC), breast cancer, thyroid cancer, and other solid tumors.

In some embodiments, compounds of Formula I, II or III and/or pharmaceutical compositions thereof are administered to modulate the pharmacokinetic profile of axitinib, e.g., to increase bioavailability, change duration of the effective plasma concentration, decrease the variability of plasma levels, reduce the side effects of axitinib, and/or improve the therapeutic effect in a subject, as compared to administration of axitinib itself.

In other embodiments, compounds of Formula I, II or III and/or pharmaceutical compositions thereof are administered to improve biodistribution, reduce the metabolism, and/or broaden the therapeutic application of axitinib in a subject, as compared to administration of axitinib itself.

In another embodiment, compounds of Formula I, II or III and/or pharmaceutical compositions thereof are administrated to increase or modulate the half-life of axitinib through modification of the PK profile, and thereby decrease dose frequency of the compound to a subject, as compared to administration of axitinib itself.

In some embodiments, there are provided methods of treating a disease state or condition mediated by tyrosine kinases in a subject in need thereof, the method comprising administering an effective amount of a compound of Formula I, II or III or a pharmaceutical composition thereof to the subject, such that the disease state or condition is treated. In an embodiment, there is provided a method of treating a tumor or a cancer in a subject in need thereof, the method comprising administering an effective amount of a compound of Formula I, II or III or a pharmaceutical composition thereof to the subject, such that the tumor or the cancer is treated.

In another broad aspect, the compounds and methods of the present invention are used alone in treating a disease state or condition mediated by tyrosine kinases in a subject.

In some embodiment, for the treatment of a disease state or condition mediated by tyrosine kinases in a subject, the compounds and methods of the present invention are used in combination with therapeutic agents or methods, including, but not limited to, programmed cell death 1 (PD-1) and programmed cell death ligand 1 (PD-L1) inhibitors.

In further broad aspect, there are provided kits comprising one or more compound or pharmaceutical composition described herein. A kit may further comprise one or more additional therapeutic agents and/or instructions, for example, instructions for using the kit to treat a subject having disease states or conditions mediated by tyrosine kinases.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which.

DETAILED DESCRIPTION

Definitions

Figure 1:
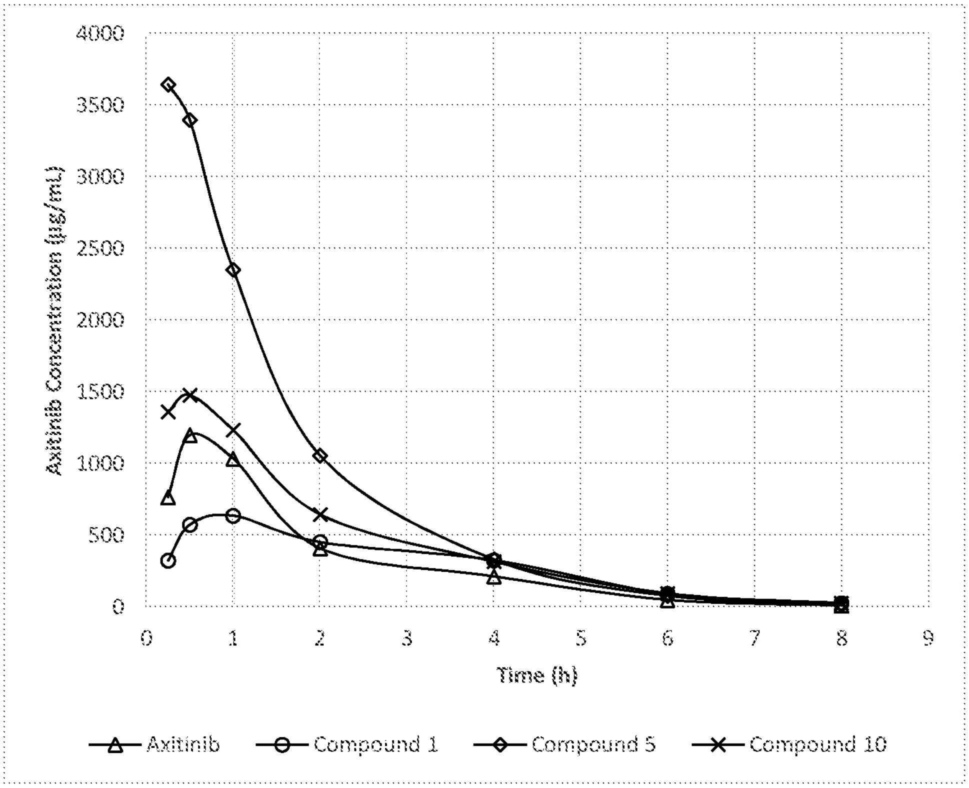
FIG. 1 shows plasma axitinib concentration-time curves in mice after oral administration of axitinib, compounds 1, 5, and 10 to the animals at a mole-equivalent dose of 30 mg/kg for all compounds: -○-, compound 1; -◇-, compound 2, -x-, compound 10; and -Δ-, axitinib.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "derivative" as used herein, is understood as being a substance similar in structure to another compound but differing in some slight structural detail.

The present description refers to a number of chemical terms and abbreviations used by those skilled in the art. Nevertheless, definitions of selected terms are provided for clarity and consistency.

As used herein, the term "substituted" or "with substitution" refers to a parent compound or a moiety has at least one (1) substituent group. The term "unsubstituted" or "without substitution" refers to a parent compound or a moiety has no other substituent group except that the unidentified valence is chemically saturated with hydrogen atoms.

As used herein, a "substituent" or a "substituent group" refers to a group selected from halogen (F, Cl, Br, or I), hydroxy, sulfhydryl, amino, nitro, carbonyl, carboxyl, alkyl, alkoxyl, alkylamino, aryl, aryloxyl, arylamino, acyl, thionyl, sulfonyl, phosphonyl, or other organic moiety as used and accepted in general organic chemistry.

As used herein, the term "alkyl" refers to saturated hydrocarbons having from one to twelve carbon atoms, including linear, branched, and cyclic alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, cyclopropyl, cyclopentyl, cyclohexyl, cycloheptyl, cyclooctyl, and the like. The term alkyl includes both unsubstituted alkyl groups and substituted alkyl groups. The term "$C_1$-$C_n$alkyl", wherein n is an integer from 2 to 12, refers to an alkyl group having from 1 to the indicated "n" number of carbon atoms. Alkyl residues may be substituted or unsubstituted. In some embodiments, for example, alkyl may be substituted by hydroxyl, amino, carboxyl, carboxylic ester, amide, carbamate, or aminoalkyl.

Unless the number of carbons is otherwise specified, "lower" as in "lower aliphatic," "lower alkyl," "lower alkenyl," and "lower alkylnyl", as used herein means that the moiety has at least one (two for alkenyl and alkynyl) and equal to or less than 6 carbon atoms.

The terms "cycloalkyl", "alicyclic", "carbocyclic" and equivalent expressions refer to a group comprising a saturated or partially unsaturated carbocyclic ring in a single, spiro (sharing one atom), or fused (sharing at least one bond) carbocyclic ring system having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The term "$C_3$-$C_n$cycloalkyl", wherein n is an integer from 4 to 15, refers to a cycloalkyl group having from 3 to the indicated "n" number of carbon atoms in the ring structure. Unless the number of carbons is otherwise specified, "lower cycloalkyl" groups as herein used, have at least 3 and equal to or less than 8 carbon atoms in their ring structure.

Cycloalkyl residues can be saturated or contain one or more double bonds within the ring system. In particular they can be saturated or contain one double bond within the ring system. In unsaturated cycloalkyl residues the double bonds can be present in any suitable positions. Monocycloalkyl residues are, for example, cyclopropyl, cyclobutyl, cyclopentyl, cyclopentenyl, cyclohexyl, cyclohexenyl, cycloheptyl, cycloheptenyl, cyclooctyl, cyclononyl, cyclodecyl, cycloundecyl, cyclododecyl or cyclotetradecyl, which can also be substituted, for example by $C_{1-4}$ alkyl. Examples of substituted cycloalkyl residues are 4-methylcyclohexyl and 2,3-dimethylcyclopentyl. Examples of parent structures of bicyclic ring systems are norbornane, bicyclo[2.2.1]heptane, bicyclo[2.2.2]octane and bicyclo[3.2.1]octane.

The term "heterocycloalkyl" and equivalent expressions refer to a group comprising a saturated or partially unsaturated carbocyclic ring in a single, spiro (sharing one atom), or fused (sharing at least one bond) carbocyclic ring system having from three to fifteen ring members, including one to six heteroatoms (e.g., N, O, S, P) or groups containing such heteroatoms (e.g., NH, $NR_x$ ($R_x$ is alkyl, acyl, aryl, heteroaryl or cycloalkyl), $PO_2$, SO, $SO_2$, and the like). Heterocycloalkyl groups may be C-attached or heteroatom-attached (e.g., via a nitrogen atom) where such is possible. Examples of heterocycloalkyl groups include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, 3H-indolyl, quinolizinyl, and sugars, and the like. The term heterocycloalkyl includes both unsubstituted heterocycloalkyl groups and substituted heterocycloalkyl groups. The term "$C_3$-$C_n$heterocycloalkyl", wherein n is an integer from 4 to 15, refers to a heterocycloalkyl group having from 3 to the indicated "n" number of atoms in the ring structure, including at least one hetero group or atom as defined above. Unless the number of carbons is otherwise specified, "lower heterocycloalkyl" groups as herein used, have at least 3 and equal to or less than 8 carbon atoms in their ring structure.

The terms "aryl" and "aryl ring" refer to aromatic groups having "4n+2".pi.(pi) electrons, wherein n is an integer from 1 to 3, in a conjugated monocyclic or polycyclic system (fused or not) and having six to fourteen ring atoms. A polycyclic ring system includes at least one aromatic ring. Aryl may be directly attached, or connected via a $C_1$-$C_3$alkyl group (also referred to as arylalkyl or aralkyl). Examples of aryl groups include, without limitation, phenyl, benzyl, phenetyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthernyl, anthracenyl, and the like. The term aryl includes both unsubstituted aryl groups and substituted aryl groups. The term "$C_6$-$C_n$aryl", wherein n is an integer from 6 to 15, refers to an aryl group having from 6 to the indicated "n" number of atoms in the ring structure, including at least one hetero group or atom as defined above.

The terms "heteroaryl" and "heteroaryl ring" refer to an aromatic groups having "4n+2".pi.(pi) electrons, wherein n is an integer from 1 to 3, in a conjugated monocyclic or polycyclic system (fused or not) and having five to fourteen ring members, including one to six heteroatoms (e.g. N, O, S) or groups containing such heteroatoms (e.g. NH, $NR_x$ ($R_x$ is alkyl, acyl, aryl, heteroaryl or cycloalkyl), SO, and the like). A polycyclic ring system includes at least one heteroaromatic ring. Heteroaryls may be directly attached, or connected via a $C_1$-$C_3$alkyl group (also referred to as heteroarylalkyl or heteroaralkyl). Heteroaryl groups may be C-attached or heteroatom-attached (e.g., via a nitrogen atom), where such is possible. Examples of heteroaryl groups include, without limitation, pyridyl, imidazolyl, pyrimidinyl, pyrazolyl, triazolyl, tetrazolyl, furyl, thienyl; isooxazolyl, thiazolyl, oxazolyl, isothiazolyl, pyrrollyl, quinolinyl, isoquinolinyl, indolyl, isoindolyl, chromenyl, isochromenyl, benzimidazolyl, benzofuranyl, cinnolinyl, indazolyl, indolizinyl, phthalazinyl, pyridazinyl, pyrazinyl, triazinyl, isoindolyl, pteridinyl, purinyl, oxadiazolyl, thiadiazolyl, furazanyl, benzofurazanyl, benzothiophenyl, benzothienyl, benzothiazolyl, benzoxazolyl, quinazolinyl, quinolizinyl, quinolonyl, isoquinolonyl, quinoxalinyl, naphthyridinyl, furopyridinyl, carbazolyl, phenanthridinyl, acridinyl, perimidinyl, phenanthrolinyl, phenazinyl, phenothiazinyl, phenoxazinyl, dibenzofurnayl, and the like. The term heteroaryl includes both unsubstituted heteroaryl groups and substituted heteroaryl groups. The term "$C_5$-$C_n$heteroaryl", wherein n is an integer from 6 to 15, refers to a heteroaryl group having from 5 to the indicated "n" number of atoms in the ring structure, including at least one hetero group or atom as defined above.

The terms "heterocycle" or "heterocyclic" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, and the like. The term heterocycle includes both unsubstituted heterocyclic groups and substituted heterocyclic groups.

The term "amine" or "amino," as used herein, refers to an unsubstituted or substituted moiety of the formula —$NR^aR^b$, in which $R^a$ and $R^b$ are each independently hydrogen, alkyl, aryl, or heterocyclyl, or $R^a$ and $R^b$, taken together with the nitrogen atom to which they are attached, form a heterocyclic ring. The term amino includes compounds or moieties in which a nitrogen atom is covalently bonded to at least one carbon or heteroatom. Thus, the terms "alkylamino" and "dialkylamino" as used herein mean an amine group having respectively one and at least two $C_1$-$C_6$alkyl groups attached thereto. The terms "arylamino" and "diarylamino" include groups wherein the nitrogen is bound to at least one or two aryl groups, respectively. The terms "amide" or "aminocarbonyl" include compounds or moieties which contain a nitrogen atom which is bound to the carbon of a carbonyl or a thiocarbonyl group. The term "acylamino" refers to an amino group directly attached to an acyl group as defined herein.

The term "alkylthio" refers to an alkyl group, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group having a carboxyl group attached thereto.

The terms "alkoxy" or "lower alkoxy" as used herein mean an alkyl group having an oxygen atom attached thereto. Representative alkoxy groups include groups having 1 to about 6 carbon atoms, e.g., methoxy, ethoxy, propoxy, tert-butoxy and the like. Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups, and the like. The term "alkoxy" includes both unsubstituted or substituted alkoxy groups, etc., as well as perhalogenated alkyloxy groups.

The terms "carbonyl" or "carboxy" include compounds and moieties which contain a carbon connected with a double bond to an oxygen atom. Examples of moieties which contain a carbonyl include aldehydes, ketones, carboxylic acids, amides, esters, anhydrides, etc.

The term "acyl" refers to a carbonyl group that is attached through its carbon atom to a hydrogen (i.e., formyl), an aliphatic group (C1-C6alkyl, C1-C6alkenyl, C1-C6alkynyl, e.g., acetyl), a cycloalkyl group (C3-C8cycloalkyl), a heterocyclic group (C3-C8 heterocycloalkyl and C5-C6 heteroaryl), an aromatic group (C6 aryl, e.g., benzoyl), and the like. Acyl groups may be unsubstituted or substituted acyl groups (e.g., salicyloyl).

The term "solvate" refers to a physical association of a compound with one or more solvent molecules, whether organic or inorganic. This physical association includes hydrogen bonding. In certain instances, a solvate will be capable of isolation, for example when one or more solvent molecules are incorporated in the crystal lattice of a crystalline solid. "Solvate" encompasses both solution-phase and isolable solvates. Exemplary solvates include, without limitation, hydrates, ethanolates, methanolates, hemiethanolates, and the like.

A "pharmaceutically acceptable salt" of a compound means a salt of a compound that is pharmaceutically acceptable. Desirable are salts of a compound that retain or improve the biological effectiveness and properties of the free acids and bases of the parent compound as defined herein or that take advantage of an intrinsically basic, acidic or charged functionality on the molecule and that are not biologically or otherwise undesirable. Examples of pharmaceutically acceptable salts are also described, for example, in Berge et al., "Pharmaceutical Salts", J. Pharm. Sci. 66, 1-19 (1977). Non-limiting examples of such salts include:

(1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, -hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, cyclohexylaminosulfonic acid, benzenesulfonic acid, sulfanilic acid, 4-chlorobenzenesulfonic acid, 2-napthalenesulfonic acid, 4-toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like;

(2) base addition salts, formed when an acidic proton present in the parent compound either is replaced by a metal ion, including, an alkali metal ion (e.g., lithium, sodium, potassium), an alkaline earth ion (e.g., magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like.

Pharmaceutically acceptable salts may be synthesized from a parent compound that contains a basic or acidic moiety, by conventional chemical methods. Generally, such salts are prepared by reacting the free acid or base forms of compounds with a stoichiometric amount of the appropriate base or acid in water or in an organic solvent, or in a mixture of the two. Salts may be prepared in situ, during the final isolation or purification of a compound or by separately reacting a compound in its free acid or base form with the desired corresponding base or acid, and isolating the salt thus formed. The term "pharmaceutically acceptable salts" also include zwitterionic compounds containing a cationic group covalently bonded to an anionic group, as they are "internal salts". It should be understood that all acid, salt, base, and other ionic and non-ionic forms of compounds described herein are intended to be encompassed. For example, if a compound is shown as an acid herein, the salt forms of the compound are also encompassed. Likewise, if a compound is shown as a salt, the acid and/or basic forms are also encompassed.

As used herein the term "effective amount" refers to the amount or dose of a therapeutic agent, such as a compound, upon single or multiple dose administration to a subject, which provides the desired therapeutic, diagnostic, or prognostic effect in the subject. An effective amount can be readily determined by an attending physician or diagnostician using known techniques and by observing results obtained under analogous circumstances. In determining the effective amount or dose of compound administered, a number of factors are considered including, but not limited to: the size, age, and general health of the subject; the specific disease involved; the degree of or involvement or the severity of the disease or condition to be treated; the response of the individual subject; the particular compound administered; the mode of administration; the bioavailability characteristics of the preparation administered; the dose regimen selected; the use of concomitant medication(s); and other relevant considerations.

"Pharmaceutically acceptable" refers to drugs, medicaments, inert ingredients etc., which the term describes, suitable for use in contact with the cells or tissues of humans and animals without undue toxicity, incompatibility, instability, irritation, allergic response, and the like, commensurate with a reasonable benefit/risk ratio. It generally refers to a compound or composition that is approved or approvable by a regulatory agency of the Federal or state government or listed in the U.S. Pharmacopoeia or other generally recognized pharmacopoeia for use in animals and more particularly in humans.

"Pharmaceutically acceptable vehicle" refers to a diluent, adjuvant, excipient, vehicle or carrier with which a compound is administered. The terms "Pharmaceutically acceptable vehicle" and "Pharmaceutically acceptable carrier" are used interchangeably herein.

"Pharmaceutical composition" refers to a composition comprising a compound as described herein and at least one component comprising a pharmaceutically acceptable carrier, diluent, adjuvant, excipient, or vehicle, such as a preserving agent, a filler, a disintegrating agent, a wetting agent, an emulsifying agent, a suspending agent, a sweetening agent, a flavoring agent, a perfuming agent, an antibacterial agent, an antifungal agent, a lubricating agent, a dispensing agent, and the like, depending on the nature of the mode of administration and dosage forms. "Preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease).

"Treating" or "treatment" of any disease or disorder refers, in some embodiments, to ameliorating at least one disease or disorder. In certain embodiments "treating" or "treatment" refers to ameliorating at least one physical parameter, which may or may not be discernible by the patient. In certain embodiments, "treating" or "treatment" refers to inhibiting the disease or disorder, either physically, (e.g., stabilization of a discernible symptom), physiologically, (e.g., stabilization of a physical parameter), or both. In some embodiments, "treating" or "treatment" refers to improving the quality of life or reducing the symptoms or side effects of a disease in a subject in need thereof. "Therapeutically effective amount" means the amount of a compound that, when administered to a subject for treating or preventing a disease, is sufficient to effect such treatment or prevention of the disease. The "therapeutically effective amount" will vary depending on the compound, the disease and its severity, and the age, weight, etc., of the subject having the disease to be treated or prevented. As used herein, the term "therapeutically effective amount" refers to an amount of a compound or composition sufficient to prevent, treat, inhibit, reduce, ameliorate or eliminate one or more causes, symptoms, or complications of a disease such as cancers.

The term "subject" includes animals, including mammals and humans, particularly humans.

The term "prodrug" and equivalent expressions refer to agents which can be converted in vitro or in vivo directly or indirectly to an active form (see, e.g., R. B. Silverman, 1992, "The Organic Chemistry of Drug Design and Drug Action," Academic Press, Chap. 8; Bundgaard, Hans; Editor. Neth. (1985), "Design of Prodrugs". 360 pp. Elsevier, Amsterdam; Stella, V.; Borchardt, R.; Hageman, M.; Oliyai, R.; Maag, H.; Tilley, J. (Eds.) (2007), "Prodrugs: Challenges and Rewards, XVIII, 1470 p. Springer). Prodrugs can be used to alter the bio-distribution (e.g., to allow agents which would not typically enter the reactive site of a protease) or the pharmacokinetics for a particular agent. A wide variety of groups have been used to modify compounds to form prodrugs, for example, esters, ethers, phosphates, etc. When a prodrug is administered to a subject, the group is cleaved, enzymatically or non-enzymatically, reductively, oxidatively, or hydrolytically, or otherwise to reveal the active form. As used herein, "prodrug" includes pharmaceutically acceptable salts thereof, or pharmaceutically acceptable solvates as well as crystalline forms of any of the foregoing. Prodrugs are frequently, although not necessarily, pharmacologically inactive until converted to the active form.

The term "ester" refers to compounds that can be represented by the formula RCOOR (carboxylic ester) or the formula RSO3R' (sulfonate ester), usually respectively formed by the reaction between a carboxylic or a sulfonic acid and an alcohol usually with the elimination of water.

The term "amino acid" generally refers to an organic compound comprising both a carboxylic acid group and an amine group. The term "amino acid" includes both "natural" and "unnatural" or "non-natural" amino acids. Additionally, the term amino acid includes O-alkylated and N-alkylated amino acids, as well as amino acids having nitrogen or oxygen-containing side chains (such as Lys, Cys, or Ser) in which the nitrogen or oxygen atom has been acylated or alkylated. Amino acids may be pure L or D isomers or mixtures of L and D isomers, including (but not limited to) racemic mixtures.

The term "natural amino acid" and equivalent expressions refer to L-amino acids commonly found in naturally-occurring proteins. Examples of natural amino acids include, without limitation, alanine (Ala), cysteine (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), tyrosine (Tyr), β-alanine (β-Ala), and γ-aminobutyric acid (GABA).

The term "unnatural amino acid" refers to any derivative of a natural amino acid including D forms, and α- and β-amino acid derivatives. The terms "unnatural amino acid" and "non-natural amino acid" are used interchangeably herein. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used according to the invention (common abbreviations in parentheses): 2-aminoadipic acid (Aad), 3-aminoadipic acid (β-Aad), 2-aminobutyric acid (2-Abu), α,β-dehydro-2-aminobutyric acid (8-AU), 1-aminocyclopropane-1-carboxylic acid (ACPC), aminoisobutyric acid (Aib), 3-aminoisobutyric acid (β-Aib), 2-amino-thiazoline-4-carboxylic acid, 5-aminovaleric acid (5-Ava), 6-aminohexanoic acid (6-Ahx), 2-aminoheptanoic acid (Ahe), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-NH2-Phe), 2-aminopimelic acid (Apm), biphenylalanine (Bip), para-bromophenylalanine (4-Br-Phe), ortho-chlorophenylalanine (2-C1-Phe), meta-chlorophenylalanine (3-Cl-Phe), para-chlorophenylalanine (4-C1-Phe), meta-chlorotyrosine (3-C1-Tyr), para-benzoylphenylalanine (Bpa), tert-butylglycine (TLG), cyclohexylalanine (Cha), cyclohexylglycine (Chg), desmosine (Des), 2,2-diaminopimelic acid (Dpm), 2,3-diaminopropionic acid (Dpr), 2,4-diaminobutyric acid (Dbu), 3,4-dichlorophenylalanine (3,4-C1-2-Phe), 3,4-difluororphenylalanine (3,4-F2-Phe), 3,5-diiodotyrosine (3,5-I2-Tyr), N-ethylglycine (EtGly), N-ethylasparagine (EtAsn), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), hydroxylysine (Hyl), allo-hydroxylysine (αHyl), 5-hydroxytryptophan (5-OH-Trp), 3- or 4-hydroxyproline (3- or 4-Hyp), para-iodophenylalanine (4-I-Phe), 3-iodotyrosine (3-I-Tyr), indoline-2-carboxylic acid (Idc), isodesmosine (Ide), allo-isoleucine (a-Ile), isonipecotic acid (Inp), N-methylisoleucine (Melle), N-methyllysine (MeLys), meta-methyltyrosine (3-Me-Tyr), N-methylvaline (MeVal), 1-naphthylalanine (1-Nal), 2-naphthylalanine (2-Nal), para-nitrophenylalanine (4-NO2-Phe), 3-nitrotyrosine (3-NO2-Tyr), norleucine (Nle), norvaline (Nva), ornithine (Orn), ortho-phosphotyrosine (H2PO3-Tyr), octahydroindole-2-carboxylic acid (Oic), penicillamine (Pen), pentafluorophenylalanine (F5-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th).

For compounds provided herein, it is intended that, in some embodiments, salts thereof are also encompassed, including pharmaceutically acceptable salts. Those skilled in the art will appreciate that many salt forms (e.g., TFA salt, tetrazolium salt, sodium salt, potassium salt, etc.) are possible; appropriate salts are selected based on considerations known in the art. The term "pharmaceutically acceptable salt" refers to salts prepared from pharmaceutically acceptable non-toxic acids or bases including inorganic acids and bases and organic acids and bases. For example, for compounds that contain a basic nitrogen, salts may be prepared from pharmaceutically acceptable non-toxic acids including inorganic and organic acids. Suitable pharmaceutically acceptable acid addition salts for the compounds of the present invention include without limitation acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include without limitation metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine.

In some embodiments, there are provided methods of increasing the therapeutic effectiveness of axitinib in a subject in need thereof, comprising administering an effective amount of a compound of Formula I, II or III or a pharmaceutical composition thereof as described herein to the subject, such that the therapeutic effectiveness of axitinib is increased as compared to administration of axitinib itself. In some embodiments, the compound is a prodrug of axitinib.

In some embodiments, one or more of the following is increased by administration of a compound, an axitinib prodrug, or a pharmaceutical composition provided herein: bioavailability of axitinib; AUC of axitinib in blood or plasma; $C_{max}$ of axitinib; $T_{max}$ of axitinib; $t_{1/2}$ of axitinib; therapeutic biodistribution of axitinib; therapeutic level of axitinib in a selected tissue; and/or bioabsorption of axitinib in a subject, as compared to administration of axitinib itself. In some embodiments, one or more of the following is reduced by administration of a compound, an axitinib prodrug, or a pharmaceutical composition provided herein: metabolism of axitinib; and side effects of axitinib in a subject, as compared to administration of axitinib itself.

In some embodiments, there are provided methods of attaining a target pharmacokinetic parameter for axitinib in a subject, comprising administering an effective amount of a compound, an axitinib prodrug, or a pharmaceutical composition thereof as described herein to the subject, such that the target pharmacokinetic parameter for axitinib is attained in the subject. Non-limiting examples of target pharmacokinetic parameters include a target bioavailability, AUC in blood or plasma, $C_{max}$, $T_{max}$, bio-distribution, level in a selected tissue, half-life ($t_{1/2}$), bioabsorption, and amount or rate of metabolism. Pharmacokinetic parameters may be calculated using methods known in the art.

Compositions

In an embodiment, there is provided a pharmaceutical composition comprising a compound of the invention, e.g., a compound of Formula I, II, or III, or a pharmaceutically acceptable salt, ester, solvate or polymorph thereof, and a pharmaceutically acceptable carrier. In an embodiment, there is provided a pharmaceutical composition comprising a compound in Table 1, or a pharmaceutically acceptable salt, ester, solvate or polymorph thereof, and a pharmaceutically acceptable carrier. In another embodiment, there is provided a pharmaceutical composition comprising a compound of Formula I, II, or III or a compound in Table 1, or a pharmaceutically acceptable salt thereof, and a pharmaceutically acceptable carrier.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Example 1: Synthesis of N-methyl-2-((1-pentoxycarbonyl-3-((1E)-2-(2-pyridinyl)ethenyl)-1H-indazol-6-yl)thio)benzamide (Compound 1)

In a flask were added 1-pentanol (500 mg, 5.67 mmol, 1.0 eq.), THF (10 mL) and triethylamine (1.15 g, 11.3 mmol., 2.0 eq.). The mixture was cooled to 0° C. with an ice-water bath, followed by addition of a solution of p-nitrophenyl chloroformate in THF (1.25 g, in 10 mL). The reaction mixture was warmed to room temperature (rt), and stirred for 1 hour (h) (TLC showed completion of the reaction.), followed by concentration to remove most of the solvent. To the residual material were added water and ethyl acetate (40 mL each) for extraction. The organic layer was separated and concentrated. The residual material was purified on a silica-gel column (eluent: pet-ether and ethyl acetate from 100:0 to 100:10), giving 4-nitrophenyl pentyl carbonate (1.0 g, 69%): 1H NMR (500 MHz, $CDCl_3$): δ ppm 0.92 (t, J=6.0 Hz, 3H), 1.39 (t, J=8.2 Hz, 4H), 1.63-1.84 (m, 2H), 4.17-4.35 (m, 2H), 7.37 (dd, J=9.0, 1.9 Hz, 2H), 8.26 (dd, J=9.0, 1.9 Hz, 2H).

In a flask were placed axitinib (100 mg, 0.259 mmol, 1.0 eq.), DMF (4 mL) and triethylamine (79 mg, 0.776 mmol, 3.0 eq.). To the stirred mixture was added 4-nitrophenyl pentyl carbonate (100 mg, 0.259 mmol, 1.0 eq.); and the obtained mixture was stirred at rt for 3 h, followed by addition of water (20 mL) and ethyl acetate (30 mL). The organic layer was separated and washed with brine (3×30 mL), and concentrated. The residual material was purified on a silica-gel column (eluent: DCM-methanol, from 100:0 to 100:3), providing compound 1 (100 mg, 77%): 1H NMR (500 MHz, DMSO-d6): δ ppm 0.89 (t, J=6.9 Hz, 3H), 1.36 (d, J=3.1 Hz, 4H), 1.66-1.81 (m, 2H), 2.75 (d, J=4.6 Hz, 3H), 4.43 (t, J=6.7 Hz, 2H), 7.20 (d, J=6.9 Hz, 1H), 7.37 (dt, J=12.9, 7.6 Hz, 4H), 7.49-7.54 (m, 1H), 7.74-7.82 (m, 2H), 7.86 (t, J=7.6 Hz, 1H), 7.92 (d, J=16.4 Hz, 1H), 8.12 (s, 1H), 8.31 (d, J=8.4 Hz, 1H), 8.39 (d, J=4.6 Hz, 1H), 8.65 (d, J=4.0 Hz, 1H); 13C NMR (125 MHz, CDCl3): δ ppm 14.03, 22.37, 26.85, 27.88, 28.42, 68.48, 116.88, 121.68, 122.03, 122.71, 123.17, 123.81, 127.17, 127.83, 128.99, 130.95, 133.03, 133.33, 134.30, 137.04, 137.73, 137.91, 141.52, 147.75, 149.73, 150.64, 154.54, 168.49; m/z (ESI+): 501.0 (M+H).

Example 2: Synthesis of N-methyl-2-((1-oxododecyl-3-((1E)-2-(2-pyridinyl)ethenyl)-1H-indazol-6-yl)thio)benzamide (Compound 2)

In a flask were added axitinib (200 mg, 0.517 mmol, 1.0 eq.), DMF (4 mL), Lauric acid (126 mg, 0.621 mmol, 1.2 eq.), diisopropylamine (110 mg, 0.776 mmol, 1.5 eq.), and HATU (1-[Bis(dimethylamino)methylene]-1H-1,2,3-triazolo[4,5-b]pyridinium 3-oxide hexafluorophosphate, hexafluorophosphate azabenzotriazole tetramethyl uronium) (236 mg, 0.621 mmol, 1.2 eq.). The mixture was stirred at rt overnight, and TLC monitoring indicated the completion of the reaction. Water (20 mL) and ethyl acetate (30 mL) were added to the flask and the content was extracted in a separatory funnel. The organic layer was separated, washed with brine (3×30 mL), and concentrated. The residual material was purified on a silica-gel column (eluent: DCM-methanol, from 100:0 to 100:3), giving compound 2 (200 mg, 68%): 1H NMR (500 MHz, CDCl3): δ ppm 0.87 (t, J=6.5 Hz, 3H), 1.31 (d, J=51.8 Hz, 14H), 1.43 (d, J=7.3 Hz, 2H), 1.76-1.86 (m, 2H), 2.94 (d, J=4.5 Hz, 3H), 3.20 (t, J=7.5 Hz, 2H), 6.39 (s, 1H), 7.24 (d, J=5.8 Hz, 1H), 7.33 (d, J=7.8 Hz, 4H), 7.50 (d, J=7.6 Hz, 1H), 7.64 (s, 1H), 7.68 (d, J=16.3 Hz, 1H), 7.73 (t, J=7.6 Hz, 1H), 7.85 (d, J=16.3 Hz, 1H), 7.93 (d, J=8.4 Hz, 1H), 8.50 (s, 1H), 8.66 (d, J=4.1 Hz, 1H); 13C NMR (125 MHz, $CDCl_3$): δ ppm 14.26, 22.82, 24.73, 26.90, 29.39, 29.48, 29.52, 29.64, 29.77, 32.04, 35.23, 117.98, 121.43, 123.00, 123.33, 124.21, 125.75, 127.94, 129.12, 131.02, 133.18, 133.35, 137.50, 137.76, 138.05, 140.89, 146.97, 149.40, 154.30, 168.57, 174.15; m/z (ESI+): 569.2 (M+H).

Example 3: Synthesis of N-methyl-2-((1-(N-(t-butoxycarbonyl)-L-valyl)-3-((1E)-2-(2-pyridinyl)ethenyl)-1H-indazol-6-yl)thio)benzamide (Compound 3)

In a flask were added axitinib (150 mg, 0.388 mmol, 1.0 eq.), DMF (4 mL), Boc-Val-OSu (N-Boc-L-valine N-succinimidyl ester) (134 mg, 0.426 mmol, 1.2 eq.), and triethylamine (117 mg, 1.16 mmol, 3.0 eq.). The mixture was stirred at rt overnight. The reaction was monitored by TLC, until the starting material disappeared. To the reaction flask were added water (20 mL) and ethyl acetate (30 mL), and the content was extracted in a separatory funnel. The organic layer was separated, washed with brine (3×30 mL), and concentrated. The residual material was purified (silica-gel column; eluent DCM-methanol from 100:0 to 100:3), giving compound 3 (150 mg, 66%): 1H NMR (500 MHz, CD3OD): δ ppm 0.95 (dd, J=32.0, 6.0 Hz, 6H), 1.16-1.53 (m, 9H), 2.34 (s, 1H), 2.78 (s, 3H), 5.43 (s, 1H), 7.02 (d, J=8.6 Hz, 1H), 7.26-7.40 (m, 5H), 7.44 (s, 1H), 7.67-7.89 (m, 4H), 8.05 (d, J=8.3 Hz, 1H), 8.38 (s, 1H), 8.54 (s, 1H); 13C NMR (125 MHz, CD3OD): δ ppm 17.92, 20.07, 26.75, 28.73, 32.15, 59.56, 80.66, 118.51, 122.66, 123.19, 124.23, 124.67, 125.09, 128.81, 129.25, 131.83, 134.05, 134.73, 135.29, 138.77, 140.03, 140.19, 141.93, 148.83, 150.47, 155.65, 158.25, 171.51, 173.97; m/z (ESI+): 586.1 (M+H).

Example 4: Synthesis of N-methyl-2-((1-(t-butoxycarbonyl)-3-((1E)-2-(2-pyridinyl)ethenyl)-1H-indazol-6-yl)thio)benzamide (Compound 4)

In a flask were placed axitinib (100 mg, 0.259 mmol, 1.0 eq.), DMF (4 mL), di-tert-butyl decarbonate (diBoc, 63 mg, 0.285 mmol, 1.1 eq.), and triethylamine (52 mg, 0.516 mmol, 2.0 eq). The reaction mixture was stirred at rt overnight. The reaction was monitored by TLC until the starting material disappeared. Then water (20 mL) and ethyl acetate (30 mL) were added to the mixture. The mixture was transferred into a separatory funnel. The organic layer was separated, washed with brine (3×30 mL), and concentrated. The residual material was purified on a silica-gel column (eluent: DCM-methanol from 100:0 to 100:3), giving compound 4 (110 mg, 87%): 1H NMR (500 MHz, CD3OD): δ ppm 1.64 (s, 9H), 2.84 (s, 3H), 7.36-7.43 (m, J=21.9, 12.9 Hz, 5H), 7.51 (d, J=6.5 Hz, 1H), 7.74 (t, J=12.6 Hz, 2H), 7.81-7.90 (m, 2H), 8.08 (d, J=7.6 Hz, 2H), 8.59 (s, 1H); 13C NMR (125 MHz, CDCl3): δ ppm 26.64, 26.78, 28.09, 85.57, 116.85, 121.50, 122.14, 122.73, 123.11, 123.75, 126.74, 127.71, 128.92, 130.88, 133.00, 133.35, 133.54, 137.17, 137.60, 137.73, 141.18, 147.02, 148.86, 149.44, 154.48, 168.50; m/z (ESI+): 486.9 (M+H).

Example 5: Synthesis of N-methyl-2-((1-((1-oxo-2,5,8,11-tetraoxadodec-1-yl)-L-valyl)-3-((1E)-2-(2-pyridinyl)ethenyl)-1H-indazol-6-yl)thio)benzamide (Compound 5)

In a flask were added, subsequently, triethylene glycol monomethyl ether (500 mg, 3.045 mmol, 1.0 eq.), THF (10 mL), and triethylamine (616 mg, 6.09 mmol, 2.0 eq.). The mixture was cooled to 0° C. (ice-water bath), followed by addition of a solution of p-nitrophenyl chloroformate in THF (675 mg in 10 mL THF, 3.350 mmol, 1.1 eq.) dropwise. The mixture was warmed to rt, and stirred at rt for 5 h, concentrated to remove most of the solvent. The residue was extracted between water and ethyl acetate (40 mL each). The organic layer was separated and concentrated. The residual material was purified (silica-gel column; eluent, pet-ether and ethyl acetate, from 100:0 to 100:10), giving 1-(3,6,9-trioxadecyl) 4-nitrophenyl carbonate (1.1 g, 99%): 1H NMR (500 MHz, CDCl3): δ ppm 3.36 (s, 3H), 3.51-3.58 (m, 2H), 3.66 (ddd, J=8.4, 6.8, 2.3 Hz, 6H), 3.80 (d, J=4.0 Hz, 2H), 4.39-4.48 (m, 2H), 7.37 (d, J=9.0 Hz, 2H), 8.26 (d, J=9.0 Hz, 2H).

In a flask were added, subsequently, axitinib (150 mg, 0.388 mmol, 1.0 eq.), DMF (4 mL), and triethylamine (79 mg, 0.776 mmol, 2.0 eq.). The mixture was stirred at rt. To the stirred mixture was added 1-(3,6,9-trioxadecyl) 4-nitrophenyl carbonate (121 mg, 0.427 mmol, 1.1 eq.), and the resultant mixture was stirred at rt overnight. After the starting material disappeared (TLC monitoring), the mixture was extracted between water (20 mL) and ethyl acetate (30 mL). The organic layer was separated, washed with brine (3×30 mL), and concentrated. The residual material was purified (silica-gel; eluent, DCM-methanol from 100:0 to 100:3), giving compound 5 (200 mg, 89%): 1H NMR (500 MHz, CD3OD): δ ppm 2.85 (s, 3H), 3.26 (s, 3H), 3.43 (d, J=4.2 Hz, 2H), 3.57 (d, J=4.6 Hz, 2H), 3.64 (s, 2H), 3.69 (s, 2H), 3.86 (s, 2H), 4.63 (s, 2H), 7.35-7.40 (m, 5H), 7.52 (d, J=6.2 Hz, 1H), 7.67-7.77 (m, 2H), 7.77-7.90 (m, 2H), 8.06 (d, J=8.2 Hz, 1H), 8.19 (s, 1H), 8.58 (s, 1H); 13C NMR (125 MHz, CDCl3): δ ppm 26.78, 59.00, 66.79, 68.71, 70.55, 70.66, 71.88, 117.27, 121.63, 121.89 122.82, 123.86, 127.47, 128.70, 130.83, 132.45, 133.79, 134.14, 137.14, 137.51, 137.77, 141.37, 147.87, 149.53, 150.36, 154.32, 168.57; m/z (ESI+): 576.9 (M+H).

Example 6: Synthesis of N-methyl-2-((1-(2,2,2-trifluoroethyloxycarbonyl)-3-((1E)-2-(2-pyridinyl)ethenyl)-1H-indazol-6-yl)thio)benzamide (compound 6)

Trifluoroethanol (500 mg, 4.98 mmol, 1.0 eq.), THF (10 mL), and triethylamine (1.1 g, 9.96 mmol, 2.0 eq.) were added subsequently into a flask. The mixture was cooled to 0° C. (ice-water bath), followed by addition (to the mixture) of a solution of p-nitrophenyl chloroformate in THF (1.1 g in 10-mL THF, 5.48 mmol, 1.1 eq.). The reaction mixture was warmed to rt, and stirred at rt overnight, until the starting material disappeared (monitored by TLC). The mixture was concentrated to remove most of the solvent, followed by addition of water and ethyl acetate (40 mL each), and transferred into a separatory funnel. The organic layer was separated and concentrated. The residual material was purified (silica-gel; eluent, pet-ether:ethyl acetate from 100:0 to 100:30), providing 4-nitrophenyl 2,2,2-trifluoroethyl carbonate (1.1 g, 75%): 1H NMR (500 MHz, CDCl3): δ ppm 4.65 (q, J=8.0 Hz, 2H), 7.35-7.52 (m, 2H), 8.22-8.36 (m, 1H).

Into a flask were subsequently added axitinib (200 mg, 0.517 mmol, 1.0 eq.), DMF (4 mL), and triethylamine (104.7 mg, 1.03 mmol, 2.0 eq.). To the stirred mixture was added 4-nitrophenyl 2,2,2-trifluoroethyl carbonate (164.6 mg, 0.621 mmol, 1.2 eq.). The reaction mixture was stirred at rt overnight. After the starting material disappeared (monitored by TLC), water (20 mL) and ethyl acetate (30 mL) were added to the mixture. The content of the flask was transferred into a separatory funnel. The organic layer was separated, washed with brine (3×30 mL), and concentrated. The residual material was purified (silica-gel; DCM-methanol from 100:0 to 100:5), giving compound 6 (200 mg, 75%): 1H NMR (500 MHz, DMSO-d6): δ ppm 2.73 (d, J=4.3 Hz, 3H), 5.15 (q, J=8.8 Hz, 2H), 7.20 (d, J=6.1 Hz, 1H), 7.35 (d, J=4.5 Hz, 3H), 7.41 (d, J=8.1 Hz, 1H), 7.50 (d, J=6.6 Hz, 1H), 7.79 (t, J=11.8 Hz, 2H), 7.85 (t, J=7.9 Hz, 1H), 7.91 (d, J=16.4 Hz, 1H), 8.08 (s, 1H), 8.32 (d, J=8.2 Hz, 1H), 8.38 (d, J=3.9 Hz, 1H), 8.64 (d, J=4.5 Hz, 1H); 13C NMR (125 MHz, DMSO-d6): δ ppm 25.98, 62.40, 116.08, 120.73, 122.02, 122.46, 123.20, 123.52, 124.23, 127.22, 127.85, 127.96, 130.37, 131.57, 133.19, 134.91, 137.00, 138.32, 138.45, 140.97, 148.02, 148.48, 149.71, 153.68, 167.65; m/z (ESI+): 513.0 (M+H).

Example 7: Synthesis of N-methyl-2-((1-((1S)-(1-methoxycarbonylethyl))amino)(phenoxy)phosphinyl-3-((1E)-2-(2-pyridinyl)ethenyl)-1H-indazol-6-yl)thio)benzamide (Compound 7)

The reaction mixture of axitinib (200 mg, 0.517 mmol, 1.0 eq.), DMF (4 mL), N-(chloro(phenyloxy)phosphinyl)-L-alanine methyl ester (172.4 mg, 0.621 mmol, 1.2 eq.), and triethylamine (104.7 mg, 1.03 mmol, 2.0 eq.) in a flask was stirred overnight at rt, until the starting material disappeared as monitored by TLC, followed by addition of water (20 mL) and ethyl acetate (30 mL). The organic layer was separated (separatory funnel), washed with brine (3×30 mL), and concentrated. The residual material was purified (silica-gel; DCM-methanol from 100:0 to 100:5), giving compound 7 (130 mg, 40%): 1H NMR (500 MHz, CD3OD): δ ppm 1.40 (d, J=22.1 Hz, 3H), 2.82 (s, 3H), 3.49 (d, J=65.4 Hz, 3H), 4.29 (s, 1H), 7.35-6.99 (m, 10H), 7.45 (s, 1H), 7.73 (d, J=73.1 Hz, 4H), 8.00 (d, J=48.9 Hz, 2H), 8.32 (s, 1H), 8.53 (s, 1H); 13C NMR (125 MHz, CD3OD): δ ppm 20.24, 26.76, 51.82, 52.73, 117.3, 121.56, 122.44, 123.51, 123.80, 123.91, 124.09, 124.40, 126.71, 128.03, 128.31, 129.09, 130.76, 131.68, 133.24, 133.73, 135.52, 137.85, 138.71, 139.41, 146.56, 149.22, 150.40, 150.45, 151.10, 151.15, 155.97, 171.47, 174.94; 31P NMR (203 MHz, DMSO-d6): δ ppm −1.82, −2.52; m/z (ESI+): 628.1 (M+H).

Example 8: N-methyl-2-((1-pivaloyl-3-((1E)-2-(2-pyridinyl)ethenyl)-1H-indazol-6-yl)thio)benzamide (Compound 8)

Under nitrogen atmosphere, axitinib (400 mg, 1.04 mmol, 1.0 eq.), DCM (35 mL), and triethylamine (315.1 mg, 3.12 mmol, 3.0 eq.) were added to a flask and the mixture was cooled with an ice-water bath, followed by addition of pivaloyl chloride (188 mg, 1.24 mmol, 1.2 eq.) dropwise. After the addition was completed, the cold bath was removed and the mixture was stirred at rt overnight. The reaction was monitored by TLC until the starting material was completely consumed. The mixture was then concentrated directly, and the residual material was purified (silica-gel; DCM-methanol from 100:0 to 100:5), giving compound 8 (400 mg, 81%): 1H NMR (500 MHz, CDCl3): δ ppm 1.58 (s, 9H), 2.95 (d, J=4.8 Hz, 3H), 6.38 (s, 1H), 7.23-7.26 (m, 1H), 7.28-7.38 (m, 4H), 7.52 (d, J=7.8 Hz, 1H), 7.60-7.72 (m, 2H), 7.76 (s, 1H), 7.93 (dd, J=24.1, 12.2 Hz, 2H), 8.56 (s, 1H), 8.67 (s, 1H); 13C NMR (125 MHz, $CDCl_3$): δ ppm 26.85, 27.97, 42.16, 119.02, 121.13, 122.74, 122.99, 123.20, 123.42, 127.75, 127.88, 129.10, 130.94, 133.00, 133.36, 133.69, 137.17, 137.67, 142.23, 146.12, 149.70, 154.54, 168.57, 178.39; m/z (ESI+): 471.0 (M+H).

Example 9: N-methyl-2-((1-((1S)-(1-methoxycarbonylethyl))amino)(1-naphthoxy)phosphinyl-3-((1E)-2-(2-pyridinyl)ethenyl)-1H-indazol-6-yl)thio)benzamide (Compound 10)

1-naphthol (720 mg, 4.99 mmol, 1.0 eq.) and diethyl ether (20 mL) were placed in a flask. Under nitrogen atmosphere, the system was cooled at −78° C., followed by addition of phosphorus oxychloride (765 mg, 4.99 mmol, 1.0 eq.) and triethylamine (504 mg, 4.99 mmol, 1.0 eq.) dropwise and subsequently. The mixture was stirred at −78° C. for 1 h. The reaction temperature was raised to rt gradually, and the mixture stirred at rt overnight. The insoluble material was removed by filtration; and the filtrate was concentrated, giving 1-naphthyl phosphorodichloridate (1.2 g, 92%): 1H NMR (500 MHz, CDCl3): δ ppm 7.47 (t, J=8.0 Hz, 1H), 7.53-7.68 (m, 3H), 7.82 (d, J=8.0 Hz, 1H), 7.91 (d, J=7.7 Hz, 1H), 8.10 (d, J=7.9 Hz, 1H).

1-Naphthyl phosphorodichloridate (1.1 g, 4.2 mmol, 1.0 eq.), dichloromethane (30 mL), and L-alanine methyl ester hydrochloride (586 mg, 4.2 mmol, 1.0 eq.) were placed in a flask. Under nitrogen protection, the reaction system was cooled to −78° C., followed by dropwise addition of triethylamine (848 mg, 8.4 mmol, 2.0 eq.) to the mixture. After the addition was completed, the mixture was stirred at −78° C. for 1 h. Then the reaction mixture was warmed to rt, and stirred at rt for 1 h. The mixture was concentrated; and the residual material was purified (silica-gel; pet-ether:ethyl acetate from 100:0 to 50:50), giving (1-naphthoxy)((1S)-(1-methoxycarbonylehtyl)amino)phosphinyl chloride (790 mg, 57%): 1H NMR (500 MHz, CDCl3): δ ppm 1.55 (dd, J=11.6, 7.2 Hz, 3H), 3.78 (d, J=25.2 Hz, 3H), 4.31 (s, 1H), 4.50 (dd, J=34.5, 11.2 Hz, 1H), 7.43 (t, J=7.6 Hz, 1H), 7.57 (dd, J=18.4, 7.1 Hz, 3H), 7.73 (d, J=7.7 Hz, 1H), 7.87 (d, J=6.9 Hz, 1H), 8.07 (t, J=6.7 Hz, 1H).

In a flask were placed, subsequently, axitinib (200 mg, 0.517 mmol, 1.0 eq.), DMF (4 mL), (1-naphthoxy)((1S)-(1-methoxycarbonylehtyl)amino)phosphinyl chloride (186.5 mg, 0.569 mmol, 1.1 eq.), and triethylamine (131.9 mg, 1.29 mmol, 2.5 eq.). The mixture was stirred at rt for 5 h, followed by addition of water (20 mL) and ethyl acetate (30 mL). The organic layer was separated, washed with brine (3×30 mL), and concentrated. The residual material was purified on a silica-gel column (DCM-methanol, from 100:0 to 100:5), giving compound 10 (126.1 mg, 34%): 1H NMR (500 MHz, DMSO-d6): δ ppm 1.28-1.38 (d, 3H), 2.76 (s, 3H), 3.35-3.50 (s, 3H), 4.35 (s, 1H), 6.90 (d, J=9.6 Hz, 1H), 7.23-7.43 (m, 7H), 7.48 (s, 1H), 7.60 (dd, J=21.1, 14.3 Hz, 3H), 7.66-7.77 (m, 2H), 7.87 (dd, J=20.2, 11.4 Hz, 3H), 8.12-8.29 (m, 3H), 8.42 (s, 1H), 8.65 (s, 1H); 13C NMR (125 MHz, DMSO-d6): δ ppm 19.11, 19.63, 26.04, 50.05, 51.79, 115.10, 117.02, 121.53, 121.71, 121.99, 122.44, 123.25, 125.10, 125.47, 126.72, 126.30, 126.84, 127.58, 127.83, 129.69, 129.85, 130.22, 132.50, 134.22, 134.83, 134.98, 135.24, 136.9, 137.26, 144.87, 145.52, 147.16, 149.47, 153.86, 167.72, 173.07; m/z (ESI+): 678.2 (M+H).

Example 10: Synthesis of N-methyl-2-((1-((1S)-(1-isopropoxycarbonylethyl))amino)(phenoxy)phosphinyl-3-((1E)-2-(2-pyridinyl)ethenyl)-1H-indazol-6-yl)thio)benzamide (Compound 11)

In a flask were added phenol (470 mg, 4.99 mmol, 1.0 eq.) and diethyl ether (20 mL). The reaction system was cooled to −78° C., followed by addition of phosphorus oxychloride (765 mg, 4.99 mmol, 1.0 eq.) and triethylamine (504 mg, 4.99 mmol, 1.0 eq.), dropwise. The mixture was stirred at −78° C. for 1 h, then at rt overnight. The insoluble material was removed by filtration, and the filtrate was concentrated, giving phenyl dichlorophosphate (900 mg, 85%).

In a flask were placed phenyl dichlorophosphate (882 mg, 4.2 mmol, 1.0 eq.), DCM (30 mL), and L-alanine isopropyl ester hydrochloride (701.4 mg, 4.2 mmol, 1.0 eq.). The reaction system was protected under nitrogen atmosphere and cooled to −78° C., followed by addition of triethylamine (848 mg, 8.4 mmol, 2.0 eq.). The mixture was stirred at −78° C. for 1 h, at rt for 1 h, and then concentrated. The residual material was purified on silica-gel column (eluent, pet ether and ethyl acetate from 100:0 to 50:50), giving (phenoxy)((1S)-(1-isopropoxyethyl)amino)phosphinyl chloride (720 mg, 57%).

Subsequently added to a flask were axitinib (200 mg, 0.517 mmol, 1.0 eq.), DMF (4 mL), (phenoxy)((1S)-(1-isopropoxyethyl)amino))phosphinyl chloride (173.9 mg, 0.569 mmol, 1.1 eq.), and triethylamine (131.9 mg, 1.29 mmol, 2.5 eq.). The mixture was stirred at rt overnight (TLC indicating completion of the reaction), followed by addition of water (20 mL) and ethyl acetated (30 mL). The mixture was transferred into a separatory funnel; and the organic layer was separated, washed with brine (3×30 mL), and concentrated. The residual material was purified (silica-gel; eluent, DCM-methanol, from 100:0 to 100:5), giving compound 11 (128.7 mg, 38%): 1H NMR (500 MHz, DMSO-d6): δ ppm 0.97 (ddd, J=29.3, 28.5, 5.8 Hz, 6H), 1.30 (dd, J=27.7, 6.4 Hz, 3H), 2.76 (d, J=1.9 Hz, 3H), 4.20 (m, 1H), 4.69 (m, 1H), 6.86-7.00 (m, 1H), 7.00-7.21 (m, 4H), 7.29 (s, 5H), 7.41 (s, 1H), 7.50 (d, J=5.1 Hz, 1H), 7.68-7.89 (m, 2H), 7.97 (dd, J=23.9, 16.1 Hz, 2H), 8.15 (s, 1H), 8.25 (d, J=8.3 Hz, 1H), 8.43 (s, 1H), 8.67 (s, 1H); 13C NMR (125 MHz, CDCl3): δ ppm 21.06, 21.72, 26.72, 50.51, 50.92, 69.47, 115.62, 115.71, 120.60, 121.39, 122.82, 123.15, 123.68, 123.86, 125.60, 126.32, 127.81, 129.02, 130.78, 131.66, 133.22, 136.74, 137.99, 145.5, 148.09, 148.84, 149.81, 154.31, 168.71, 172.66; m/z (ESI+): 656.1 (M+H).

Example 11: Synthesis of N-methyl-2-((1-((1S)-(1-isopropoxycarbonylethyl))amino)(1-naphthoxy)phosphinyl-3-((1E)-2-(2-pyridinyl)ethenyl)-1H-indazol-6-yl)thio)benzamide (Compound 12)

In a flask were placed 1-naphthol (720 mg, 4.99 mmol, 1.0 eq.) and diethyl ether (20 mL). Under nitrogen protection, the reaction system was cooled to −78° C., followed by dropwise addition of phosphorus oxychloride (765 mg, 4.99 mmol, 1.0 eq.) and triethylamine (504 mg, 4.99 mmol, 1.0 eq.). The mixture was stirred at −78° C. for 1 h, warmed up to rt, and stirred at rt overnight. The insoluble material was removed by filtration. The filtrate was concentrated, giving 1-naphthyl dichlorophosphate (1.2 g, 92%): 1H NMR (500 MHz, CDCl3): δ ppm 7.47 (t, J=8.0 Hz, 1H), 7.53-7.68 (m, 3H), 7.82 (d, J=8.0 Hz, 1H), 7.91 (d, J=7.7 Hz, 1H), 8.10 (d, J=7.9 Hz, 1H).

In a flask were added 1-naphthyl dichlorophosphate (1.1 g, 4.2 mmol, 1.0 eq.), DCM (30 mL), and L-alanine isopropyl ester hydrochloride (701.4 mg, 4.2 mmol, 1.0 eq.). The reaction system was protected with nitrogen atmosphere, and cooled to −78° C. To this cold mixture was added dropwise triethylamine (848 mg, 8.4 mmol, 2.0 eq.). The mixture was stirred at −78° C. for 1 h, then warmed to rt, and stirred at rt for 1 h. Then the mixture was concentrated; and the residual material was purified (silica-gel; eluent, pet-ether:ethyl acetate from 100:0 to 50:50), providing ((1S)-(1-isopropoxycarbonyl)ethyl)amino)(1-naphthoxy)phosphinyl chloride (800 mg, 53%): 1H NMR (500 MHz, CDCl3): δ ppm 1.23-1.34 (m, 6H), 1.54 (t, J=8.4 Hz, 3H), 2.05 (s, 1H), 4.24 (dt, J=17.3, 8.8 Hz, 1H), 4.48 (dt, J=39.8, 10.7 Hz, 1H), 5.08 (ddd, J=18.6, 12.4, 6.2 Hz, 1H), 7.44 (t, J=7.9 Hz, 1H), 7.67-7.51 (m, 3H), 7.73 (d, J=8.1 Hz, 1H), 7.87 (d, J=7.4 Hz, 1H), 8.08 (t, J=8.4 Hz, 1H).

Axitinib (200 mg, 0.517 mmol, 1.0 eq.), DMF (4 mL), ((1S)-(1-isopropoxycarbonyl)ethyl)amino)(1-naphthoxy) phosphinyl chloride (201.9 mg, 0.569 mmol, 1.1 eq.), and triethylamine (131.9 mg, 1.29 mmol, 2.5 eq.) were mixed in a flask, and stirred at rt overnight. After the reaction was completed, water (20 mL) and ethyl acetate (30 mL) were added to the mixture. The organic layer was separated, washed with brine (3×30 mL), and concentrated. The residual material was purified (silica-gel; DCM-methanol, from 100:0 to 100:5), giving compound 12 (112 mg, 30%): 1H NMR (500 MHz, DMSO-d6): δ ppm 0.96 (ddd, J=48.9, 35.2, 6.2 Hz, 6H), 1.31 (dd, J=57.4, 6.9 Hz, 3H), 2.76 (d, J=4.0 Hz, 3H), 4.18-4.53 (m, 1H), 4.71 (dd, J=11.8, 5.8 Hz, 1H), 6.82-6.97 (m, 1H), 7.18-7.42 (m, 7H), 7.48 (s, 1H), 7.64 (dt, J=31.8, 17.2 Hz, 5H), 7.78-7.94 (m, 3H), 8.13-8.23 (m, 2H), 8.27 (d, J=8.0 Hz, 1H), 8.39 (s, 1H), 8.63 (s, 1H); 13C NMR (125 MHz, CDCl3): δ ppm 21.10, 21.71, 26.68, 50.59, 50.94, 69.50, 115.69, 121.33, 121.97, 122.87, 122.98, 123.05, 123.28, 125.46, 126.33, 126.50, 126.58, 126.81, 127.76, 129.01, 130.76, 133.20, 134.81, 136.74, 137.47, 138.12, 145.51, 146.04, 148.25, 149.21, 154.52, 168.65, 172.64; 31P NMR (203 MHz, DMSO-d6): δ ppm −1.77, −2.22; m/z (ESI+): 706.2 (M+H).

Example 12: N-methyl-2-((1-(N-(t-butoxycarbonyl)-L-phenylalanyl)-3-((1E)-2-(2-pyridinyl)ethenyl)-1H-indazol-6-yl)thio)benzamide (Compound 13)

To a flask were added axitinib (300 mg, 0.778 mmol, 1.0 eq.), DMF (4 mL), N-Boc-L-phenylalanine (247 mg, 0.934 mmol, 1.2 eq.), N,N-diisopropylethylamine (151 mg, 1.16 mmol, 1.5 eq.), and HATU (354 mg, 0.934 mmol, 1.2 eq). The mixture was stirred at rt overnight, followed by addition of water (20 mL) and ethyl acetate (30 mL). The mixture was transferred to a separatory funnel; and the organic layer was separated, washed with brine (3×30 mL), and concentrated. The residual material was purified (silica-gel; eluent, DCM-methanol, from 100:0 to 100:3), giving compound 13 (300 mg, 60%): 1H NMR (500 MHz, CD3OD): δ ppm 1.29 (m, 9H), 2.83 (d, J=18.4 Hz, 3H), 2.19-3.09 (m, 1H), 3.21 (s, 1H), 5.76 (s, 1H), 7.17 (d, J=7.4 Hz, 1H), 7.25 (t, J=7.3 Hz, 2H), 7.31 (d, J=6.5 Hz, 2H), 7.38 (d, J=12.5 Hz, 5H), 7.50 (s, 1H), 7.77 (d, J=16.1 Hz, 2H), 7.86 (d, J=16.5 Hz, 2H), 8.08 (d, J=8.1 Hz, 1H), 8.39 (s, 1H), 8.61 (s, 1H); 13C NMR (125 MHz, $CDCl_3$): δ ppm 26.69, 26.96, 28.26, 39.12, 49.38, 54.41, 79.96, 117.37, 121.37, 123.18, 123.24, 126.95, 127.88, 128.43, 128.99, 129.37, 130.83, 133.08, 133.34, 134.33, 136.12, 137.04, 138.33, 140.87, 147.99, 149.68, 154.18, 155.19, 168.36, 171.81; m/z (ESI+): 634.2 (M+H).

Example 13: N-methyl-2-((1-(N-(t-butoxycarbonyl)-L-histidyl)-3-((1E)-2-(2-pyridinyl)ethenyl)-1H-indazol-6-yl)thio)benzamide (Compound 14)

To a flask were added axitinib (300 mg, 0.78 mmol, 1.0 eq.), DMF (6 mL), N(α)-(t-Boc)-L-histidine (219 mg, 0.86 mmol, 1.1 eq.), DPPA (234 mg, 0.86 mmol, 1.1 eq.), and triethylamine (95 mg, 0.94 mmol, 1.2 eq.). The mixture was stirred at rt overnight, followed by addition of water (20 mL) and ethyl acetate (30 mL). The mixture was transferred to a separatory funnel; and the organic layer was separated, washed with brine (3×30 mL), and concentrated. The residual material was purified (silica-gel; eluent, DCM-methanol, 10:1), giving compound 14 (195 mg, 40.1%): 1H NMR (500 MHz, CD3OD): δ ppm 1.30 (d, J=65.8 Hz, 9H), 2.76 (s, 3H), 3.10 (s, 2H), 5.58 (s, 1H), 6.84 (s, 1H), 7.64-7.03 (m, 8H), 8.01-7.65 (m, 4H), 8.35 (dd, J=24.2, 15.7 Hz, 3H), 8.67 (s, 1H); 13C NMR (125 MHz, DMSO-d6): δ ppm 26.50, 28.60, 29.22, 54.00, 55.32, 79.04, 117.76, 121.57, 122.85, 124.04, 127.52, 128.24, 128.45, 128.98, 130.84, 131.79, 134.22, 135.23, 135.32, 137.54, 138.49, 138.75, 140.78, 147.65, 150.25, 154.28, 155.83, 168.19, 172.60; m/z (ESI+): 624.4 (M+H).

Example 14: Synthesis of N-methyl-2-((1-(4-fluorophenoxy)((1S)-(1-methoxycarbonylethyl))amino)phosphinyl-3-((1E)-2-(2-pyridinyl)ethenyl)-1H-indazol-6-yl)thio)benzamide (Compound 15)

In a flask were placed 4-fluorophenol (4.3 g, 38.7 mmol, 1.0 eq.) and diethyl ether (20 mL). The reaction system was protected with nitrogen atmosphere and cooled to −78° C., followed by dropwise addition of phosphorus oxychloride (6 g, 38.7 mmol, 1.0 eq.) and triethylamine (3.92 g, 38.7 mmol, 1.0 eq.). The mixture was stirred for 1 h at −78° C. The temperature of the reaction was gradually raised to rt; and then the mixture was stirred at rt for 1 h. The insoluble material was removed by filtration; and the filtrate was concentrated, giving 4-fluorophenyl phosphorodichloridate (8 g, 90%).

To a flask were added subsequently 4-fluorophenyl phosphorodichloridate (8 g, 35.2 mmol, 1.0 eq.), DCM (30 mL), and L-alanine methyl ester hydrochloride (3.20 g, 27.1 mmol, 0.8 eq.). The mixture, under nitrogen atmosphere, was cooled at −78° C., followed by dropwise addition of triethylamine (7.84 g, 77.4 mmol, 2.4 eq.). The mixture was stirred for 1 h at −78° C. The temperature of the reaction was gradually raised to rt; and then the mixture was stirred at rt for 1 h. The mixture was then concentrated; and the residual material was purified (silica-gel; eluent: pet-ether and ethyl acetate, from 100:0 to 50:50), giving (4-fluorophenoxy)((1S)-(1-methoxycarbonylethyl))amino)phosphinyl chloride (3.0 g, 38%).

To a flask were added axitinib (400 mg, 1.03 mmol, 1.0 eq.), N,N-dimethylformamide (6 mL), (4-fluorophenoxy)((1S)-(1-methoxycarbonylethyl))amino)phosphinyl chloride (678.5 mg, 2.30 mmol, 2.2 eq.), and triethylamine (260.5 mg, 2.6 mmol, 2.5 eq.). The mixture was stirred at rt for 5 h, followed by addition of water (20 mL) and ethyl acetate (30 mL) for extraction. The organic layer was separated, washed with brine (3×30 mL), and concentrated. The residual material was purified (silica-gel; DCM-methanol from 100:0 to 100:2), providing compound 15 (205 mg, 31.7%): 1H NMR (500 MHz, CD3OD): δ 1.42 (dd, J=16.2, 6.7 Hz, 3H), 2.84 (s, 3H), 3.54 (d, J=61.5 Hz, 3H), 4.32 (d, J=34.9 Hz, 1H), 6.98 (s, 2H), 7.15 (d, J=23.4 Hz, 3H), 7.28-7.43 (m, 4H), 7.48 (s, 1H), 7.2 Hz, 2H), 7.72 (dd, J=16.5, 2H), 7.83 (d, J=16.3 Hz, 2H), 8.00-8.04 (m, 2H), 8.59 (s, 1H); 13C NMR (125 MHz, CD3OD): δ 18.81, 25.33, 50.86, 115.80, 121.03, 121.91, 122.39, 122.57, 123.05, 126.66, 127.02, 127.74, 130.29, 132.22, 134.00, 136.70, 137.37, 138.23, 145.23, 145.67, 148.00, 149.03, 154.63, 159.05, 160.98, 170.14, 173.33; 31P NMR (203 MHz, CD3OD): δ −2.22, −1.77; m/z (ESI−): 644.1 (M−H).

Example 15: Synthesis of N-methyl-2-((1-((1S)-(1-methoxycarbonylethyl))amino)(4-methylphenoxy)phosphinyl-3-((1E)-2-(2-pyridinyl)ethenyl)-1H-indazol-6-yl)thio)benzamide (Compound 17)

To a flask were added 4-methylphenol (5 g, 46.2 mmol, 1.0 eq.) and diethyl ether (200 mL). The reaction system was protected with nitrogen atmosphere and cooled to −78° C., followed by dropwise addition of phosphorus oxychloride (7.1 g, 46.2 mmol, 1.0 eq.) and triethylamine (4.66 g, 46.2 mmol, 1.0 eq.). The mixture was stirred for 1 h at −78° C. The temperature of the reaction was gradually raised to rt; and then the mixture was stirred at rt for 1 h. The insoluble material was removed by filtration; and the filtrate was concentrated, giving 4-methylphenyl phosphorodichloridate (9.0 g, 87%).

4-methylphenyl phosphorodichloridate (7.29 g, 32.37 mmol, 1.0 eq.), DCM (150 mL), and L-alanine methyl ester hydrochloride (4.52 g, 32.37 mmol, 1.0 eq.) were added in a flask. The reaction system was protected with nitrogen atmosphere and cooled to −78° C., followed by dropwise addition of triethylamine (6.54 g, 64.74 mmol, 2.0 eq.). The mixture was stirred for 1 h at −78° C. The temperature of the reaction was gradually raised to rt; and then the mixture was stirred at rt for 1 h. The mixture was concentrated; and the residual material was purified (silica-gel; pet-ether and ethyl acetate, from 100:0 to 50:50), providing ((1S)-(1-methoxy-carbonylethyl)amino)(4-methylphenoxy)phosphinyl chloride (1.4 g, 30%): 1H NMR (500 MHz, CDCl3): δ ppm 1.51 (d, J=4.7 Hz, 3H), 2.32 (s, 3H), 3.78 (d, J=8.5 Hz, 3H), 4.18 (d, J=7.7 Hz, 1H), 4.42 (d, J=28.9 Hz, 1H), 7.11 (d, J=30.0 Hz, 4H).

To a flask were added subsequently axitinib (450 mg, 1.16 mmol, 1.0 eq.), DMF (15 mL), ((1S-1-methoxycarbonyl-ethyl)amino)(4-methylphenoxy)phosphinyl chloride (1.37 g, 4.66 mmol, 4.0 eq.), and triethylamine (476 mg, 4.66 mmol, 4.0 eq.). The mixture was stirred at rt for 16 h, followed by addition of water and ethyl acetate (60 mL each). The organic layer was separated, washed with brine (3×60 mL), and concentrated. The residual material was purified on a silica-gel column (eluent, DCM-methanol, from 100:0 to 100:5, v/v), giving compound 17 (300 mg, 40%): 1H NMR (500 MHz, DMSO-d6): δ ppm 1.31 (dd, J=20.8, 6.8 Hz, 3H), 2.76 (d, J=4.0 Hz, 3H), 3.43 (d, J=56.9 Hz, 3H), 4.25 (s, 1H), 7.14-6.91 (m, 6H), 7.32 (d, J=23.1 Hz, 4H), 7.49 (s, 1H), 7.72 (dd, J=20.0, 10.5 Hz, 2H), 8.00-7.82 (m, 2H), 8.12 (d, J=5.6 Hz, 1H), 8.25 (d, J=8.1 Hz, 1H), 8.39 (s, 1H), 8.64 (s, 1H); 13C NMR (125 MHz, DMSO-d6): δ ppm 19.34, 20.10, 25.98, 50.02, 51.66, 116.88, 119.91, 121.69, 121.96, 122.33, 123.11, 126.25, 127.32, 127.80, 129.74, 129.91, 130.01, 130.15, 132.71, 134.46, 134.82, 135.11, 136.94, 137.07, 144.82, 147.05, 147.31, 149.64, 154.06, 167.66, 173.03; 31P NMR (203 MHz, DMSO-d6): δ ppm −1.78, −2.54; m/z (ESI+): 642.1 (M+H).

Example 16: Synthesis of N-methyl-2-((1-(4-chlorophenoxy)((1S)-(1-methoxycarbonylethyl))amino) phosphinyl-3-((1E)-2-(2-pyridinyl)ethenyl)-1H-indazol-6-yl)thio)benzamide (Compound 19)

To a flask were added 4-chlorophenol (4.2 g, 38.7 mmol, 1.0 eq.) and diethyl ether (20 mL). The reaction system was protected with nitrogen atmosphere and cooled to −78° C., followed by dropwise addition of phosphorus oxychloride (6 g, 38.7 mmol, 1.0 eq.) and triethylamine (3.92 g, 38.7 mmol, 1.0 eq.). The mixture was stirred for 1 h at −78° C. The temperature of the reaction was gradually raised to rt; and then the mixture was stirred at rt overnight. The insoluble material was removed by filtration; and the filtrate was concentrated, giving 4-chlorophenyl phosphorodichloridate (8.0 g, 85%).

In a flask were placed 4-chlorophenyl phosphorodichloridate (8.0 g, 32.9 mmol, 1.0 eq.), DCM (30 mL), and L-alanine methyl ester hydrochloride (3.20 g, 27.1 mmol, 0.8 eq.). The reaction system was protected with nitrogen atmosphere and cooled to −78° C., followed by dropwise addition of triethylamine (7.84 g, 77.4 mmol, 2.4 eq.). The mixture was stirred for 1 h at −78° C. The temperature of the reaction was gradually raised to rt; and then the mixture was stirred at rt for 1 h. The mixture was concentrated; and the residual material was purified (silica-gel; pet-ether and ethyl acetate, from 100:0 to 50:50), providing (4-chlorophenoxy)((S-1-methoxycarbonylethyl)amino)phosphinyl chloride (3.0 g, 42%).

Axitinib (400 mg, 1.03 mmol, 1.0 eq.), DMF (6 mL), (4-chlorophenoxy)((1S-1-methoxycarbonylethyl)amino) phosphinyl chloride (702.5 mg, 2.30 mmol, 2.2 eq.), and triethylamine (260.5 mg, 2.6 mmol, 2.5 eq.) were subsequently placed in a flask. The mixture was stirred at rt for 5 h, followed by addition of water (20 mL) and ethyl acetate (30 mL). The organic layer was separated, washed with brine (3×30 mL), and concentrated. The residual material was purified (silica-gel column; eluent, DCM-methanol from 100:0 to 100:2), giving compound 19 (210 mg, 30.8%): 1H NMR (500 MHz, CD3OD) δ 1.43 (s, 3H), 2.84 (s, 3H), 3.53 (d, J=60.8 Hz, 3H), 4.31 (d, J=32.5 Hz, 1H), 7.22 (dd, J=60.7, 41.0 Hz, 9H), 7.48 (s, 1H), 7.84 (s, 2H), 8.04 (s, 2H), 7.71 (s, 2H), 8.30 (s, 1H), 8.57 (s, 1H); 13C NMR (125 MHz, CD3OD) δ 25.32, 50.24, 115.73, 121.84, 122.58, 123.08, 126.63, 127.08, 127.76, 129.35, 130.32, 130.69, 132.10, 132.47, 133.91, 136.85, 137.42, 138.33, 148.39, 149.02, 154.63, 170.16; 31P NMR (203 MHz, CD3OD) δ −1.47, −0.88; m/z (ESI−): 660.1 (M−H).

Example 17: Synthesis of N-methyl-2-((1-ethoxy-carbonyl-3-((1E)-2-(2-pyridinyl)ethenyl)-1H-indazol-6-yl)thio)benzamide (Compound 22)

To a flask were added ethanol (0.5 g, 11.0 mmol, 1.0 eq.), THF (50 mL), and triethylamine (2.4 g, 23.9 mmol, 2.2 eq.). The reaction mixture was cooled to 0° C. (ice-water bath), followed by addition to the mixture of a solution of p-nitrophenyl chloroformate (4.3 g, 21.7 mmol, 2.0 eq.) in THF (30 mL), dropwise. After completion of the addition, the reaction temperature was raised to rt. The mixture was stirred at rt for 4 h, and then concentrated. To the residual material were added water and ethyl acetate (40 mL each). The organic layer was separated, washed with brine (3×30 mL), and concentrated. The residual material was purified on a silica-gel column (eluent, pet-ether and ethyl acetate from 100:0 to 95:5), giving ethyl p-nitrophenyl carbonate (1.5 g, 65.2%).

To a flask were added axitinib (400 mg, 1.03 mmol, 1.0 eq.), DMF (12 mL), and triethylamine (312.1 mg, 3.09 mmol, 3.0 eq.). To the stirred mixture was added ethyl p-nitrophenyl carbonate (282.7 mg, 1.34 mmol, 1.3 eq.). The mixture was further stirred at rt overnight, followed by addition of water (50 mL) and ethyl acetate (90 mL). The organic layer was separated, washed with brine (3×70 mL), and concentrated. The residual material was purified on a silica-gel column (eluent: DCM-methanol from 100:0 to 100:3), giving compound 22 (350 mg, 74.3%): 1H NMR (500 MHz, DMSO-d6): δ ppm 1.36 (t, J=7.1 Hz, 3H), 2.75 (d, J=4.7 Hz, 3H), 4.48 (q, J=7.0 Hz, 2H), 7.21 (d, J=7.4 Hz, 1H), 7.32-7.43 (m, 4H), 7.52 (d, J=7.2 Hz, 1H), 7.79 (dd, J=12.0, 8.2 Hz, 2H), 7.87 (t, J=7.8 Hz, 1H), 7.93 (d, J=16.4 Hz, 1H), 8.12 (s, 1H), 8.31 (d, J=8.5 Hz, 1H), 8.40 (d, J=4.6 Hz, 1H), 8.66 (d, J=4.3 Hz, 1H); 13C NMR (125 MHz, DMSO-d6): δ ppm 14.06, 26.03, 63.95, 116.34, 121.03, 122.20, 122.97, 123.45, 126.98, 127.28, 127.96, 130.40, 131.59, 133.38, 134.18, 137.02, 137.70, 138.47, 140.90, 146.90, 149.76, 153.84, 167.72; m/z (ESI+): 459.2 (M+H).

Example 18: Synthesis of N-methyl-2-((1-dodecyloxycarbonyl-3-((1E)-2-(2-pyridinyl)ethenyl)-1H-indazol-6-yl)thio)benzamide (Compound 25)

1-Dodecanol (3 g, 16.1 mmol, 1.0 eq.), THF (50 mL), and triethylamine (4.88 g, 48.3 mmol, 3.0 eq.) were placed in a flask and cooled to 0° C. (ice-water bath), followed by addition, dropwise, of a solution of p-nitrophenyl chloroformate (3.89 g, 19.32 mmol, 1.2 eq.) in THF (30 mL). After addition, the temperature of the reaction was raised to rt; and the mixture was stirred at rt for 4 h, then concentrated to remove most of the solvent, followed by addition of water and ethyl acetate (40 mL each). The organic layer was separated and concentrated. The residue was purified (silica-gel column; eluent, pet-ether to ethyl acetate from 100:0 to 95:5), providing 1-dodecyl p-nitrophenyl carbonate (4.1 g, 71.8%).

To a flask were added axitinib (400 mg, 1.03 mmol, 1.0 eq.), DMF (12 mL), and triethylamine (312.1 mg, 3.09 mmol, 3.0 eq.). To the mixture under effective stirring was added 1-dodecyl p-nitrophenyl carbonate (472 mg, 1.34 mmol, 1.3 eq.). The latter mixture was stirred at rt for 3 h, followed by addition to the mixture of water (50 mL) and ethyl acetate (90 mL). The organic layer was separated, washed with brine (3×70 mL), and concentrated. The residual material was purified (silica-gel column; eluent DCM-methanol from 100:0 to 100:3), giving compound 25 (512 mg, 82.3%): 1H NMR (500 MHz, CDCl3) δ ppm 0.87 (t, J=6.8 Hz, 3H), 1.26 (s, 14H), 1.34 (d, J=14.4 Hz, 2H), 1.39-1.50 (m, 2H), 1.78-1.93 (m, 2H), 2.95 (d, J=4.9 Hz, 3H), 4.50 (t, J=7.0 Hz, 2H), 6.38 (s, 1H), 7.19-7.25 (m, 1H), 7.29-7.38 (m, 4H), 7.49 (d, J=7.7 Hz, 1H), 7.62-7.68 (m, 1H), 7.68-7.75 (m, 2H), 7.87 (d, J=16.4 Hz, 1H), 7.97 (d, J=8.4 Hz, 1H), 8.23 (s, 1H), 8.65 (d, J=4.3 Hz, 1H); 13C NMR (125 MHz, CDCl3) δ ppm 14.15, 22.70, 25.71, 26.78, 28.66, 29.25, 29.36, 29.52, 29.59, 29.65, 31.92, 68.42, 116.89, 121.56, 121.70, 122.62, 123.74, 127.14, 127.68, 128.86, 130.84, 132.84, 133.41, 134.49, 136.75, 137.64, 137.82, 141.44, 147.70, 149.87, 150.57, 154.56, 168.47; m/z (ESI+): 599.4 (M+H).

Example 19: Synthesis of N-methyl-2-((1-(2-oxo-4H-1,3,2-benzodioxaphosphorin-2-yl)-3-((1E)-2-(2-pyridinyl)ethenyl)-1H-indazol-6-yl)thio)benzamide (Compound 27)

2-Hydroxybenzyl alcohol (4 g, 32.23 mmol, 1.0 eq.) and DCM (120 mL) were mixed in a flask. Under nitrogen atmosphere, the mixture was cooled to −78° C., followed by dropwise addition of, to the mixture, phosphorus oxychloride (4.94 g, 32.23 mmol, 1.0 eq.) and triethylamine (6.5 g, 64.46 mmol, 2.0 eq.). The mixture was stirred at −78° C. for 1 h; and the reaction temperature was then raised to rt. The mixture was further stirred at rt for 3 h. At this point, pentafluorophenol (5.94 g, 32.23 mmol, 1.0 eq.) was introduced into the reaction mixture under nitrogen atmosphere. Under nitrogen protection, the reaction system was cooled to −78° C., followed by addition of triethylamine (3.26 g, 32.23 mmol, 2.0 eq.) dropwise. The resultant mixture was stirred at −78° C. for 1 h, brought to rt, and further stirred at rt for 1 h. The mixture was then concentrated; and the residual material was purified (silica-gel column; eluent pet-ether to ethyl acetate from 100:0 to 50:50) to give 2-oxo-4H-2-pentafluorophenoxy-1,3,2-benzodioxaphosphorin (6.1 g, 53.7%).

In a flask were added axitinib (300 mg, 0.776 mmol, 1.0 eq.), DMF (12 mL), and DBU (141.7 mg, 0.931 mmol, 1.2 eq.). The mixture was cooled to −20° C., followed by addition, dropwise, of 2-oxo-4H-2-pentafluorophenoxy-1,3,2-benzodioxaphosphorin (327.9 mg, 0.931 mmol, 1.2 eq.) in DMF (1 mL). The mixture was stirred at −20° C. for 40 min, followed by addition of water (50 mL) and ethyl acetate (70 mL). The organic layer was separated, washed with brine (3×50 mL), and concentrated. The residue was purified on a silica-gel column (eluent, DCM-methanol from 100:0 to 97:3), giving compound 27 (243 mg, 56.5%): 1H NMR (500 MHz, DMSO-d6) δ ppm: 2.77 (d, J=4.6 Hz, 3H), 5.78 (dd, J=18.6, 14.3 Hz, 1H), 5.88-5.98 (m, 1H), 7.16 (d, J=7.6 Hz, 1H), 7.22 (d, J=8.1 Hz, 1H), 7.29-7.41 (m, 5H), 7.44 (t, J=8.0 Hz, 2H), 7.52 (d, J=7.3 Hz, 1H), 7.67 (dd, J=20.4, 12.1 Hz, 2H), 7.82 (dd, J=16.8, 12.0 Hz, 2H), 8.07 (s, 1H), 8.33 (d, J=7.9 Hz, 1H), 8.41 (d, J=4.4 Hz, 1H), 8.60 (d, J=4.3 Hz, 1H); 13C NMR (125 MHz, DMSO-d6) δ ppm: 26.11, 70.59, 115.53, 118.15, 121.12, 121.60, 122.40, 122.60, 123.49, 125.12, 126.35, 126.93, 127.77, 127.99, 130.20, 130.49, 131.00, 134.01, 134.13, 137.02, 137.10, 137.84, 144.58, 149.02, 149.60, 153.73, 167.79; 31P NMR (203 MHz, DMSO-d6): δ ppm: −15.28; m/z (ESI+): 555.2 (M+H).

Example 20: Synthesis of N-methyl-2-((1-(P(S)-((1S)-(1-isopropoxycarbonylethyl))amino)(phenoxy) phosphinyl(-3-((1E)-2-(2-pyridinyl)ethenyl)-1H-indazol-6-yl)thio)benzamide (Compound 39)

A flask loaded with (((1S)-1-isopropoxycarbonylethyl) amino)(phenoxy)phosphinyl chloride (8.7 g, 28.4 mmol, 1.0 eq.) and DCM (100 mL) was protected under nitrogen atmosphere and cooled to 0° C. To this cold mixture was added TEA (2.9 g, 31.2 mmol, 1.1 eq.) and a solution of pentafluorophenol (5.2 g, 28.4 mmol, 1.0 eq.) in DCM (20 mL). The resulting mixture was stirred at 0° C. for 4 h, and then concentrated to a residue. The residual material was treated with methyl t-butyl ether (100 mL). Insoluble material was removed by filtration; and the filtrate was concentrated to dryness. The solid material thus obtained was stirred in a mixture of ethyl acetate and hexane (20 to 80, v/v; total 50 mL) overnight. The white solid was collected, giving N—(P(S)-(phenoxy)(pentafluorophenoxy)phosphinyl)-L-alanine isopropyl ester (5.8 g, 45.1%).

To a flask were added axitinib (500 mg, 1.3 mmol, 1.0 eq.), DMF (13 mL), and N—(P(S)-(phenoxy)(pentafluorophenoxy)phosphinyl)-L-alanine isopropyl ester (704 mg, 1.6 mmol, 1.2 eq.). The mixture was cooled to −50° C., followed by addition of DBU (208 mg, 1.4 mmol, 1.1 eq.); and the mixture was stirred at −50° C. for 1 h. The reaction was quenched by addition of 4 mL of 0.5 M HCl solution. The mixture was then extracted with ethyl acetate (30 mL). The organic layer was separated, washed with brine (3×30 mL), and concentrated. The residual material was purified on a silica-gel column (eluent, DCM-methanol from 100:0 to 100:2, v/v), giving compound 39 (280 mg, 32.8%): 1H NMR (500 MHz, DMSO-d6): δ ppm 1.02 (d, J=6.2 Hz, 3H), 1.09 (d, J=6.3 Hz, 3H), 1.31 (d, J=7.2 Hz, 3H), 2.79 (d, J=4.6 Hz, 3H), 4.24 (d, J=7.3 Hz, 1H), 4.66-4.84 (m, 1H), 6.94-7.00 (m, 1H), 7.06 (dd, J=13.8, 10.3 Hz, 1H), 7.15-7.24 (m, 3H), 7.28-7.41 (m, 6H), 7.49-7.55 (m, 1H), 7.68-7.77 (m, 2H), 7.97-7.85 (m, 2H), 8.16 (s, 1H), 8.27 (d, J=8.3 Hz, 1H), 8.42 (d, J=4.5 Hz, 1H), 8.66 (d, J=4.1 Hz, 1H); 13C NMR (125 MHz, DMSO-d6): δ ppm 20.25, 21.71, 26.56, 50.74, 68.46, 117.54, 120.78, 122.36, 122.63, 122.88, 123.65, 123.73, 125.84, 126.70, 128.04, 128.33, 130.26, 130.76, 133.20, 135.28, 135.88, 137.28, 137.47, 145.19, 145.28, 147.56, 147.65, 150.12, 154.54, 168.22, 172.64; 31P NMR (203 MHz, DMSO-d6): δ ppm −2.69; m/z (ESI+): 656.2 (M+H).

Example 21: Synthesis of N-methyl-2-((1-(b-L-asparaginyl)-3-((1E)-2-(2-pyridinyl)ethenyl)-1H-indazol-6-yl)thio)benzamide bis(trifluoroacetate) (Compound 40)

In a flask were mixed axitinib (500 mg, 1.3 mmol, 1.0 eq.), DMF (10 mL), N-(t-Boc)-L-aspartic acid 1-t-butyl ester (413 mg, 1.4 mmol, 1.1 eq.), and TEA (328 mg, 3.3 mmol, 2.5 eq.), followed by addition of DPPA (716 mg, 2.6 mmol, 2 eq.) dropwise. The mixture was stirred at rt for 4 h, and then to the mixture were added water (50 mL) and ethyl acetate (200 mL). The organic layer was separated, washed with brine (3×50 mL), and concentrated. The residual material was purified on a silica-gel column (eluent, DCM-methanol, 10:1), providing Boc-protected intermediate (800 mg, 93.6%). This intermediate (800 mg) was taken in DCM (20 mL) in a flask, followed by addition of TFA (10 mL) dropwise. The mixture was stirred at rt for 2.5 h, and then concentrated. The crude product thus obtained was stirred in methanol-ethyl acetate (5:95, v/v; total 10 mL); and the solid material was collected by filtration and dried, providing compound 40 (380 mg, 52.0%): 1H NMR (500 MHz, DMSO-d6): δ ppm 2.78 (s, 3H), 3.81 (s, 1H), 3.92 (d, J=17.3 Hz, 1H), 4.52 (s, 1H), 7.24 (s, 1H), 7.41 (s, 3H), 7.53 (d, J=17.2 Hz, 2H), 7.91 (dd, J=40.1, 22.8 Hz, 4H), 8.33 (s, 1H), 8.41 (s, 4H), 8.70 (s, 1H); 13C NMR (125 MHz, DMSO-d6): δ ppm 26.33, 39.63, 48.56, 117.38, 121.42, 123.01, 124.04, 124.20, 127.73, 128.51, 128.51, 130.93, 132.01, 133.90, 135.29, 137.80, 138.88, 139.08, 140.61, 147.98, 150.10, 153.99, 158.72, 168.18, 169.82, 170.36; m/z (ESI+): 502.0 (M+H).

Example 22: N-methyl-2-((1-(P(S)-(1S)-(1-methoxycarbonylethyl))amino)(1-naphthoxy)phosphinyl-3-((1E)-2-(2-pyridinyl)ethenyl)-1H-indazol-6-yl)thio)benzamide (Compound 41)

(1S)-(1-Methoxycarbonylethyl))amino)(1-naphthoxy) phosphinyl chloride (8.4 g, 17.7 mmol, 1.0 eq.) and DCM (100 mL) were placed in a flask. The system was protected with nitrogen atmosphere, and cooled to 0° C., followed by addition of TEA (2.0 g, 19.5 mmol, 1.1 eq.) dropwise. Then to the mixture was added a solution of pentafluorophenol (3.2 g, 17.7 mmol, 1.0 eq.) in DCM (20 mL). The mixture was stirred at 0° C. for 4 h, and then concentrated. The residual material was dissolved in methyl t-butyl ether (100 mL) and filtered. The filtrate was concentrated to dryness, providing a solid. The material was stirred in a mixture of ethyl acetate and hexane (20:80, v/v; total 50 mL) overnight. The white solid was collected and dried, giving N—(P(S)-(1-naphthoxy)(pentafluorophenoxy)phosphinyl)-L-alanine methyl ester (6.0 g, 71.3%).

Axitinib (500 mg, 1.3 mmol, 1.0 eq.) and N—(P(S)-(1-naphthoxy)(pentafluorophenoxy)phosphinyl)-L-alanine methyl ester (741 mg, 1.6 mmol, 1.2 eq.) were mixed in DMF (13 mL) in a flask and cooled to −50° C., followed by addition of DBU (208 mg, 1.4 mmol, 1.1 eq.) dropwise. The mixture was stirred at −50° C. for 1 h, and then the reaction was quenched by addition of 0.5 M HCl (4 mL). The mixture was extracted with ethyl acetate (30 mL). The organic layer was separated, washed with brine (3×30 mL), and concentrated. The residual material was purified on a silica-gel column (eluent: DCM-methanol, from 100:0 to 100:2), giving compound 41 (201 mg, 22.8%): 1H NMR (500 MHz, DMSO-d6): δ ppm 1.28 (d, J=7.2 Hz, 3H), 2.76 (d, J=4.6 Hz, 3H), 3.50 (s, 3H), 4.27-4.40 (m, 1H), 6.90 (d, J=7.3 Hz, 1H), 7.23-7.41 (m, 7H), 7.49 (d, J=6.7 Hz, 1H), 7.53-7.66 (m, 3H), 7.70 (dd, J=17.7, 7.3 Hz, 2H), 7.84 (dd, J=15.7, 7.7 Hz, 2H), 7.91 (d, J=8.1 Hz, 1H), 8.13 (s, 1H), 8.19 (d, J=8.3 Hz, 1H), 8.25 (d, J=8.4 Hz, 1H), 8.41 (d, J=4.6 Hz, 1H), 8.57-8.72 (m, 1H); 13C NMR (125 MHz, DMSO-d6): δ ppm 20.16, 26.55, 50.63, 52.33, 115.69, 117.47, 121.78, 122.00, 122.55, 123.01, 123.70, 125.62, 130.22, 130.77, 133.22, 134.69, 135.82, 137.27, 137.51, 145.32, 145.91, 145.96, 147.60, 147.69, 150.20, 154.46, 168.21, 173.69; 31P NMR (203 MHz, DMSO-d6): δ ppm −2.12; m/z (ESI+): 678.3 (M+H).

Example 23: Synthesis of N-methyl-2-((1-nicotinoyl-3-((1E)-2-(2-pyridinyl)ethenyl)-1H-indazol-6-yl)thio)benzamide (Compound 42)

In a flask were placed axitinib (300 mg, 0.778 mmol, 1.0 eq.), DMF (5 mL), nicotinic acid (116 mg, 0.945 mmol, 1.2 eq.), N,N-diisopropylethylamine (151 mg, 1.16 mmol, 1.5 eq.), and HATU (354 mg, 0.934 mmol, 1.2 eq). The mixture was stirred at rt overnight, followed by addition of water (20 mL) and ethyl acetate (30 mL). The organic layer was separated, washed with brine (3×30 mL), and concentrated. The residual material was purified (silica-gel column; eluent, DCM-methanol from 100:0 to 100:3), giving compound 42 (240 mg, 63%): 1H NMR (500 MHz, CD3OD): δ ppm 2.86 (s, 3H), 7.32 (s, 1H), 7.41 (s, 4H), 7.51 (s, 1H), 7.62 (d, J=26.9 Hz, 3H), 7.77 (d, J=46.4 Hz, 2H), 8.03 (s, 1H), 8.41-8.58 (m, 3H), 8.73 (s, 1H), 9.19 (s, 1H); 13C NMR (125 MHz, CDCl3): δ ppm 26.69, 117.73, 121.35, 123.19, 123.98, 128.09, 128.87, 129.11, 130.78, 132.80, 133.37, 134.68, 136.74, 138.25, 138.71, 138.94, 141.63, 148.31, 149.81, 151.94, 152.45, 154.17, 165.87, 168.51; m/z (ESI+): 492.1 (M+H).

Example 24: Synthesis of N-acetyl-N-methyl-2-((1-acetyl-3-((1E)-2-(2-pyridinyl)ethenyl)-1H-indazol-6-yl)thio)benzamide (Compound 43)

p-Nitrophenol (9.7 g, 63.86 mmol, 1.0 eq.), DCM (50 mL), and triethylamine (12.9 g, 127.6 mmol, 2.0 eq.) were mixed in a flask. The reaction system was protected under nitrogen atmosphere and cooled in an ice-water bath. Acetyl chloride (5 g, 70.24 mmol, 1.1 eq.) was added dropwise into the above reaction system. After completion of the addition, the cold bath was removed. The mixture was stirred at rt for 3 h, and then concentrated. The residue was purified (silica-gel column; eluent, pet ether to ethyl acetate from 100:0 to 90:10), providing p-nitrophenyl acetate (10 g, 86.4%).

Axitinib (1 g, 2.59 mmol, 1.0 eq.), DCM (50 mL), and triethylamine (784.7 mg, 7.77 mmol, 3.0 eq.) were mixed in a flask, and cooled in an ice-water bath under nitrogen atmosphere. To the cold mixture was added dropwise acetyl chloride (405 mg, 5.18 mmol, 2.0 eq.). The cold bath was then removed; and the mixture was stirred at rt for 16 h, followed by addition of water (60 mL). The organic layer was separated, washed with brine (60 mL), and concentrated. The residue was purified (silica-gel column; eluent, DCM-methanol from 100:0 to 100:3), giving N-methyl-2-((1-acetyl-3-((1E)-2-(2-pyridinyl)ethenyl)-1H-indazol-6-yl)thio)benzamide (1.1 g, 99%).

N-methyl-2-((1-acetyl-3-((1E)-2-(2-pyridinyl)ethenyl)-1H-indazol-6-yl)thio)benzamide (1.1 g, 2.58 mmol, 1.0 eq.) and THF (35 mL) were placed in a flask. Under nitrogen atmosphere, the mixture was cooled in an ice-water bath, followed by addition to the mixture of Lithium bis(trimethylsilyl)amide (LiHMDS, 1.0 M solution in THF; 7.74 mL, 7.74 mmol, 3.0 eq.). The mixture was stirred in the cold bath for 30 min., followed by addition of a solution of p-nitrophenyl acetate (1.4 g) in THF (10 mL), and continued being stirred for 2 h in the cold bath and for 1 h at rt afterwards. After addition of water (40 mL) and ethyl acetate (70 mL), the organic layer was separated and concentrated. The residue was purified on a silica-gel column (eluent: pet-ether and ethyl acetate, from 100:0 to 60:40), giving compound 43

(200 mg, 16.4%): 1H NMR (500 MHz, CDCl3): δ ppm 2.41 (s, 3H), 2.78 (s, 3H), 3.11 (s, 3H), 7.27-7.30 (m, 1H), 7.32 (dd, J=8.4, 1.5 Hz, 1H), 7.41 (d, J=2.7 Hz, 4H), 7.53 (d, J=7.6 Hz, 1H), 7.73 (d, J=16.3 Hz, 1H), 7.78 (t, J=7.6 Hz, 1H), 7.90 (d, J=16.2 Hz, 1H), 7.96 (d, J=8.3 Hz, 1H), 8.45 (d, J=0.8 Hz, 1H), 8.67 (d, J=4.9 Hz, 1H); 13C NMR (126 MHz, CDCl3): δ ppm 22.98, 26.46, 33.11, 117.35, 121.20, 121.67, 122.78, 124.08, 127.07, 127.53, 128.36, 130.90, 131.70, 133.59, 133.91, 136.91, 136.81, 137.23, 139.14, 140.44, 147.00, 149.69, 154.20, 170.92, 171.71, 173.16; m/z (ESI+): 471 (M+H).

Example 25: Synthesis of N-methyl-2-((1-(2-methoxyethoxycarbonyl)-3-((1E)-2-(2-pyridinyl)ethenyl)-1H-indazol-6-yl)thio)benzamide (Compound 44)

A mixture of 2-methoxyethanol (4 g, 52.56 mmol, 1.0 eq.), THF (50 mL), and triethylamine (10.62 g, 105.12 mmol, 2.0 eq.) was cooled in an ice-water bath, followed by addition of a solution of p-nitrophenyl chloroformate (13.7 g, 68.34 mmol, 1.3 eq.) in THF (50 mL). Temperature was then raised to rt; and the mixture was stirred at rt for 4 h. After concentration, the residue was extracted between water (100 mL) and ethyl acetate (100 mL). The organic layer was separated and concentrated. The residual material was purified (silica-gel column; eluent, pet-ether and ethyl acetate from 100:0 to 90:10), providing 2-methoxyethyl p-nitrophenyl carbonate (7.2 g, 56.8%).

Axitinib (450 mg, 1.16 mmol, 1.0 eq.), DMF (12 mL), and triethylamine (351.48 mg, 3.48 mmol, 3.0 eq.) were mixed and stirred in a flask, followed by addition of 2-methoxyethyl p-nitrophenyl carbonate (337.1 mg, 1.39 mmol, 1.2 eq.). The mixture was stirred at rt for 3 h, followed by addition of water (100 mL) and ethyl acetate (120 mL). The organic layer was separated, washed with brine (3×70 mL), and concentrated. The residue was purified on a silica-gel column (eluent: DCM-methanol, from 100:0 to 100:3), giving compound 44 (452 mg, 79.8%): 1H NMR (500 MHz, CDCl3) δ ppm 2.94 (d, J=4.9 Hz, 3H), 3.43 (s, 3H), 3.72-3.85 (m, 2H), 4.59-4.69 (m, 2H), 6.39 (s, 1H), 7.23 (dd, J=7.0, 5.2 Hz, 1H), 7.31-7.38 (m, 4H), 7.49 (d, J=7.8 Hz, 1H), 7.61-7.68 (m, 1H), 7.73 (dd, J=14.9, 5.9 Hz, 2H), 7.87 (d, J=16.4 Hz, 1H), 7.96 (d, J=8.4 Hz, 1H), 8.22 (s, 1H), 8.65 (d, J=4.2 Hz, 1H); 13C NMR (125 MHz, CDCl3) δ ppm 26.77, 59.02, 66.56, 70.01, 116.94, 121.52, 122.70, 123.10, 123.77, 127.25, 127.62, 128.69, 130.82, 132.82, 133.47, 134.58, 136.78, 137.76, 138.00, 141.40, 147.93, 149.86, 150.40, 154.48, 168.57; m/z (ESI+): 489.1 (M+H).

Example 26: Synthesis of N-methyl-2-((1-(1-oxo-2,5,8-trioxananyl)-3-((1E)-2-(2-pyridinyl)ethenyl)-1H-indazol-6-yl)thio)benzamide (Compound 45)

2-(2-Methyloxyethoxy)ethanol (6.3 g, 52.56 mmol, 1.0 eq.), THF (50 mL), and triethylamine (10.62 g, 105.12 mmol, 2.0 eq.) were mixed in a flask and cooled to 0° C. in an ice-water bath, followed by addition of a solution of p-nitrophenyl chloroformate (13.7 g, 68.34 mmol, 1.3 eq) in THF (50 mL). The temperature was raised to rt; and the mixture was stirred at rt for 4 h. Solvent was removed on a rotary evaporator; and the residual material was treated with ethyl acetate and water (100 mL each). The organic layer was separated and concentrated. The residue was purified (silica-gel column; eluent, pet-ether and ethyl acetate from 100:0 to 90:10), providing 2-(2-methoxyethoxy)ethyl p-nitrophenyl carbonate (8.0 g, 53.7%).

Axitinib (450 mg, 1.16 mmol, 1.0 eq.), DMF (12 mL), and triethylamine (351.48 mg, 3.48 mmol, 3.0 eq.) were mixed and stirred at rt, followed by addition of 2-(2-methoxyethoxy)ethyl p-nitrophenyl carbonate (396.2 mg, 1.39 mmol, 1.2 eq.). The mixture was stirred at rt for 3 h, followed by addition of water (100 mL) and ethyl acetate (120 mL). The organic layer was separated, washed with brine (3×70 mL), and concentrated. The residual material was purified on a silica-gel column (eluent: DCM-methanol, from 100:0 to 100:3), giving compound 45 (500 mg, 80.6%): 1H NMR (500 MHz, DMSO-d6): δ ppm 2.76 (d, J=4.6 Hz, 3H), 3.21 (s, 3H), 3.46 (dd, J=5.6, 3.9 Hz, 2H), 3.60 (dd, J=5.6, 3.9 Hz, 2H), 3.74-3.83 (m, 2H), 4.52-4.61 (m, 2H), 7.13-7.19 (m, 1H), 7.32-7.43 (m, 4H), 7.53 (dd, J=7.2, 1.9 Hz, 1H), 7.79 (t, J=12.1 Hz, 2H), 7.87 (td, J=7.7, 1.7 Hz, 1H), 7.94 (d, J=16.3 Hz, 1H), 8.20 (s, 1H), 8.36 (dd, J=37.4, 6.6 Hz, 2H), 8.66 (d, J=4.6 Hz, 1H); 13C NMR (125 MHz, CDCl3): δ ppm 26.78, 59.06, 66.76, 68.74, 70.60, 71.91, 117.20, 121.56, 122.75, 123.12, 123.87, 127.50, 128.74, 130.83, 132.59, 133.67, 134.59, 136.80, 137.59, 137.78, 141.39, 147.95, 149.88, 150.39, 154.51, 168.55; m/z (ESI+): 533.2 (M+H).

Example 27: Synthesis of N-methyl-2-((1-(1-oxo-2,5,8,11,14-pentaoxapentadecyl)-3-((1E)-2-(2-pyridinyl)ethenyl)-1H-indazol-6-yl)thio)benzamide (Compound 46)

3,6,9,12-Tetraoxatridecan-1-ol (4 g, 19.2 mmol, 1.0 eq.), THF (50 mL), and triethylamine (5.8 g, 57.69 mmol, 3.0 eq.) were mixed in a flask and cooled to 0° C. in an ice-water bath, followed by addition of a solution of p-nitrophenyl chloroformate (3.87 g, 19.23 mmol, 1.0 eq.) in THF (20 mL). The temperature was raised to rt after completion of addition. Then the mixture was stirred at rt for 4 h, concentrated to remove most of the solvent, followed by addition of water and ethyl acetate (100 mL each). The organic layer was separated and concentrated. The residual material was purified (silica-gel column; eluent, pet-ether and ethyl acetate from 80:20 to 50:50), giving p-nitrophenyl 3,6,9,12-tetraoxatridecyl carbonate (5.3 g, 73.9%).

Axitinib (400 mg, 1.03 mmol, 1.0 eq.), DMF (12 mL), and triethylamine (313.6 mg, 3.1 mmol, 3.0 eq.) were mixed and stirred in a flask, followed by addition of p-nitrophenyl 3,6,9,12-tetraoxatridecyl carbonate (462.9 mg, 1.24 mmol, 1.2 eq.). The mixture was stirred at rt overnight. Water (100 mL) and ethyl acetate (120 mL) were added to the reaction mixture. The organic layer was separated, washed with brine (3×70 mL), and concentrated. The residue was purified (silica-gel column; eluent, DCM-methanol from 100:0 to 100:3), giving compound 46 (456 mg, 71.32%): 1H NMR (500 MHz, CDCl3) δ ppm 2.95 (d, J=4.9 Hz, 3H), 3.37 (d, J=16.9 Hz, 3H), 3.53 (dt, J=6.2, 4.6 Hz, 2H), 3.59-3.62 (m, 4H), 3.62-3.67 (m, 4H), 3.68-3.75 (m, 2H), 3.84-3.92 (m, 2H), 4.61-4.68 (m, 2H), 6.51 (s, 1H), 7.23 (dd, J=7.0, 5.2 Hz, 1H), 7.28-7.39 (m, 4H), 7.49 (d, J=7.9 Hz, 1H), 7.60-7.67 (m, 1H), 7.69-7.79 (m, 2H), 7.87 (d, J=16.4 Hz, 1H), 7.98 (d, J=8.4 Hz, 1H), 8.24 (s, 1H), 8.65 (d, J=4.3 Hz, 1H); 13C NMR (125 MHz, CDCl3) δ ppm 26.74, 58.95, 66.76, 68.68, 70.41, 70.50, 70.55, 70.60, 71.84, 117.23, 121.49, 121.56, 122.74, 123.12, 123.82, 127.42, 127.54, 128.66, 130.77, 132.39, 133.82, 134.55, 136.80, 137.49, 137.78, 141.34, 147.91, 149.83, 150.33, 154.44, 168.57; m/z (ESI+): 621.3 (M+H).

Example 28: Synthesis of N-methyl-2-((1-(2-(2-hydroxyethoxy)ethoxycarbonyl)-3-((1E)-2-(2-pyridinyl)ethenyl)-1H-indazol-6-yl)thio)benzamide hydrochloride (Compound 49)

In a flask were subsequently added diethylene glycol (3.5 g, 33.0 mmol, 5.0 eq.), DCM (10 mL), DMAP (0.16 g, 1.3 mmol, 0.2 eq.), TEA (0.67 g, 6.6 mmol, 1.0 eq.), and DCM (10 mL). The mixture was cooled to 0° C., followed by addition of a solution of TBSCl (1.0 g, 6.6 mmol, 1.0 eq.) in DCM (2.5 mL). The reaction temperature was raised to rt; and the reaction continued at rt for 3 h, followed by washing the reaction mixture with saturated ammonium chloride solution (30 mL) and brine (30 mL) subsequently. The organic layer was concentrated, providing diethylene glycol mono-(tert-butyldimethylsilyl) ether (1.3 g, 89.4%).

Diethylene glycol mono-(tert-butyldimethylsilyl) ether (1.3 g, 5.9 mmol, 1.0 eq.), DCM (15 mL), and TEA (0.66 g, 6.5 mmol, 1.1 eq.) were mixed in a flask. The mixture was cooled to 0° C., followed by dropwise addition of a solution of p-nitrophenyl chloroformate (1.1 g, 5.3 mmol, 0.9 eq.) in DCM (6 mL). The reaction temperature was raised to rt; and the reaction continued at rt for 3 h. The mixture was soaked on silica gel and loaded on a silica-gel column for purification (eluent: pet-ether and ethyl acetate, from 100:0 to 100:20), giving 2-(2-(tert-butyldimethylsilyloxy)ethoxy) ethyl p-nitrophenyl carbonate (1.6 g, 78.3%).

In a flask were placed axitinib (835 mg, 2.2 mmol, 1.0 eq.), DMF (21 mL), TEA (556 mg, 5.5 mmol, 2.5 eq.), and a solution of 2-(tert-butyldimethylsilyloxyethoxy)ethyl p-nitrophenyl carbonate (1.0 g, 2.6 mmol, 1.2 eq.) in DMF (5 mL). At room temperature the mixture was stirred overnight, followed by addition of water (60 mL) and ethyl acetate (90 mL). The organic layer was separated, washed with brine (3×50 mL), and concentrated. The residual material was purified on a silica-gel column (eluent: DCM-methanol, from 100:0 to 100:3), giving N-methyl-2-((1-(2-(2-(tert-butyldimethysilyloxy)ethoxy)ethoxycarbonyl)-3-((1E)-2-(2-pyridinyl)ethenyl)-1H-indazol-6-yl)thio)benzamide (1.7 g, 81.0%). The above obtained product (1.0 g) was stirred in a solution of 1% hydrochloric acid in ethanol (60 mL) at rt for 2 h. The mixture was then concentrated to dryness, giving compound 49 (780 mg, 87.8%): 1H NMR (500 MHz, D2O): δ ppm 2.71 (s, 3H), 3.56-3.65 (m, 2H), 3.65-3.73 (m, 2H), 3.80 (s, 2H), 4.46 (s, 2H), 6.90 (d, J=8.4 Hz, 1H), 7.20 (t, J=11.3 Hz, 2H), 7.32 (d, J=7.7 Hz, 1H), 7.42 (dq, J=18.9, 7.6 Hz, 5H), 7.89 (t, J=6.8 Hz, 1H), 8.17 (d, J=8.2 Hz, 1H), 8.45 (d, J=8.1 Hz, 1H), 8.60 (d, J=5.8 Hz, 1H); 13C NMR (125 MHz, D2O): δ ppm 26.24, 60.34, 67.51, 67.79, 71.82, 114.51, 120.76, 121.52, 123.10, 124.11, 126.28, 126.76, 127.79, 128.27, 130.94, 131.41, 132.70, 137.40, 139.10, 139.51, 141.11, 144.71, 146.69, 147.49, 149.14, 170.21; m/z (ESI+): 519.2 (M+H).

Example 29: Synthesis of N-methyl-2-((1-(2-(2-(2-hydroxyethoxy)ethoxy)ethoxycarbonyl)-3-((1E)-2-(2-pyridinyl)ethenyl)-1H-indazol-6-yl)thio)benzamide hydrochloride (Compound 50)

In a flask were added triethylene glycol (5.0 g, 33.0 mmol, 5.0 eq.), DCM (10 mL), DMAP (0.16 g, 1.3 mmol, 0.2 eq.), TEA (0.67 g, 6.6 mmol, 1.0 eq.), and DCM (10 mL). The mixture was cooled to 0° C., followed by dropwise addition of a solution of TBSCl (1.0 g, 6.6 mmol, 1.0 eq.) in DCM (2.5 mL). The reaction temperature was raised to rt; and the mixture was stirred at rt for 4 h. The mixture was then washed with saturated ammonium chloride solution (30 mL) and with brine (30 mL), subsequently. The organic layer was concentrated to dryness, providing 10,10,11,11-tetramethyl-3,6,9-trioxa-10-siladodecan-1-ol (1.4 g, 80.2%).

10,10,11,11-Tetramethyl-3,6,9-trioxa-10-siladodecan-1-ol (1.4 g, 5.3 mmol, 1.0 eq.), DCM (15 mL), and TEA (0.64 g, 6.4 mmol, 1.2 eq.) were mixed in a flask and cooled to 0° C., followed by addition of p-nitrophenyl chloroformate (1.2 g, 5.8 mmol, 1.1 eq.; dissolved in DCM, 6 mL) dropwise. The reaction temperature was raised to rt; and the mixture was stirred at rt for 3 h. The mixture was absorbed on silica-gel, loaded onto a silica-gel column, and purified with eluent of a mixture pet-ether and ethyl acetate (from 100:0 to 100:20), giving p-nitrophenyl 10,10,11,11-tetramethyl-3,6,9-trioxa-10-siladodec-1-yl carbonate (1.6 g, 70.3%).

Axitinib (1.2 g, 3.1 mmol, 1.0 eq.), DMF (30 mL), TEA (783 mg, 7.75 mmol, 2.5 eq.), and a solution of the carbonate obtained from the reaction above (1.6 g, 3.7 mmol, 1.2 eq.) in DMF (6 mL) were mixed in a flask. The mixture was stirred overnight, followed by addition of water (60 mL) and ethyl acetate (90 mL). The organic layer was separated, washed with brine (3×50 mL), and concentrated. The residual material was purified (silica-gel column; eluent, DCM-methanol from 100:0 to 100:3), providing the sily-protected intermediate (1.7 g, 81.0%). This intermediate (677 mg) was taken into a solution of 1% hydrochloric acid in ethanol (50 mL); and the mixture was stirred at rt for 2 h, and then concentrated to dryness, giving compound 50 (478 mg, 79.8%): 1H NMR (500 MHz, D2O): δ ppm 2.73 (s, 3H), 3.50 (s, 2H), 3.59 (d, J=11.1 Hz, 6H), 3.74 (s, 2H), 4.36 (s, 2H), 6.77 (s, 1H), 7.01 (d, J=15.6 Hz, 2H), 7.13-7.34 (m, 5H), 7.41 (s, 1H), 7.76 (s, 1H), 7.99 (d, J=7.3 Hz, 1H), 8.30 (s, 1H), 8.47 (s, 1H); 13C NMR (125 MHz, D2O): δ ppm 26.24, 60.34, 67.39, 67.96, 69.44, 69.84, 71.75, 114.85, 120.83, 121.70, 124.06, 126.06, 126.96, 127.17, 128.31, 131.01, 131.71, 132.54, 137.27, 138.90, 139.58, 141.83, 144.99, 145.92, 148.01, 149.22, 170.30; m/z (ESI+): 563.2 (M+H).

Example 30: Synthesis of N-methyl-2-((1-(13-hydroxy-1-oxo-2,5,8,11-tetraoxatridec-1-yl)-3-((1E)-2-(2-pyridinyl)ethenyl)-1H-indazol-6-yl)thio)benzamide hydrochloride (Compound 51)

Tetraethylene glycol (8 g, 41.18 mmol, 5.0 eq.), DCM (25 mL), DMAP (201 mg, 8.24 mmol, 0.2 eq.), and triethylamine (833.1 mg, 8.24 mmol, 1.0 eq.) were mixed in a flask and cooled to 0° C. in an ice-water bath, followed by addition of a solution of TBSCl (1.24 g, 8.24 mmol, 1.0 eq.) in DCM (5 mL). The temperature of the reaction was raised to rt; and the mixture was stirred at rt for 5 h. The mixture was washed with saturated ammonium chloride aqueous solution (2×30 mL); and the organic layer was separated and concentrated to dryness, providing 13,13,14,14-tetramethyl-3,6,9,12-tetraoxa-13-silapentadecan-1-ol (2.1 g, 82.6%).

13,13,14,14-Tetramethyl-3,6,9,12-tetraoxa-13-silapentadecan-1-ol (2.1 g, 6.8 mmol, 1.0 eq.), DCM (30 mL), and triethylamine (826.6 mg, 8.16 mmol, 1.2 eq.) were mixed in a flask, and cooled to 0° C. in an ice-water bath, followed by dropwise addition of p-nitrophenyl chloroformate (1.4 g dissolved in 10 mL DCM, 6.8 mmol, 1.0 eq.). The temperature of the reaction was raised to rt; and the mixture was stirred at rt for 5 h. The reaction mixture was then concentrated to dryness, and the residue was extracted with ethyl acetate and water (40 mL each). The organic layer was separated and concentrated. The residue was purified (silica-gel column; eluent, pet-ether and ethyl acetated from 100:0 to 100:10), providing p-nitrophenyl 13,13,14,14-tetramethyl-3,6,9,12-tetraoxa-13-silapentadec-1-yl carbonate (1.6 g, 49.7%).

A mixture of axitinib (550 mg, 1.42 mmol, 1.0 eq.), DMF (10 mL), and triethylamine (368 mg, 3.63 mmol, 2.5 eq.) was stirred in a flask, followed by addition of the above prepared carbonate (800 mg, 1.75 mmol, 1.2 eq.). The mixture was stirred at rt overnight, followed by addition of water (40 mL) and ethyl acetate (60 mL) for extraction. The organic layer was separated, washed with brine (3×40 mL), and concentrated. The residual material was purified (silica-gel column; eluent, DCM-methanol from 100:0 to 100:3), providing N-methyl-2-((1-(13,13,14,14-tetramethyl-3,6,9,12-tetraoxa-13-silapentadec-1-yl)-3-((1E)-2-(2-pyridinyl)ethenyl)-1H-indazol-6-yl)thio)benzamide (850 mg, 83.1%), which was treated, under stirring, in a solution of hydrochloric acid in ethanol (1 mL conc. HCl in 99 mL ethanol) for 3 h (TLC indicating completion of the reaction at this point). The latter mixture was concentrated to dryness, giving compound 51 (723 mg, 95.3%): 1H NMR (500 MHz, CD3OD) δ ppm: 2.86 (s, 3H), 3.44-3.51 (m, 2H), 3.51-3.57 (m, 2H), 3.57-3.64 (m, 4H), 3.64-3.75 (m, 4H), 3.87 (s, 2H), 4.64 (s, 2H), 7.34 (d, J=8.6 Hz, 1H), 7.39 (s, 1H), 7.43 (d, J=3.5 Hz, 2H), 7.55 (dd, J=5.7, 3.3 Hz, 1H), 7.87 (d, J=16.7 Hz, 1H), 7.99 (d, J=6.3 Hz, 1H), 8.07-8.22 (m, 3H), 8.55 (d, J=8.3 Hz, 1H), 8.63 (t, J=7.3 Hz, 1H), 8.80 (d, J=4.7 Hz, 1H); 13C NMR (125 MHz, D2O) δ ppm: 26.06, 60.00, 67.07, 67.59, 68.99, 69.18, 69.28, 69.37, 71.25, 114.57, 120.68, 121.34, 122.79, 123.95, 125.99, 126.65, 127.99, 130.73, 131.37, 132.19, 136.71, 138.50, 139.24, 140.69, 144.52, 146.47, 147.16, 148.87, 169.84; m/z (ESI+): 607.3 (M+H).

Example 31. Synthesis of N-methyl-2-((1-(indol-4-oxy)((1S)-1-methoxycarbonylethyl))amino)phosphinyl-3-((1E)-2-(2-pyridinyl)ethenyl)-1H-indazol-6-yl)thio)benzamide (Compound 61)

Under nitrogen atmosphere, 1H-indol-4-ol (6 g, 45.06 mmol, 1.0 eq.) and DCM (200 mL) were placed in a flask, and cooled to −78° C., followed by addition dropwise of phosphorus oxychloride (6.91 g, 45.06 mmol, 1.0 eq.) and triethylamine (4.55 g, 45.06 mmol, 1.0 eq.), subsequently. The mixture was stirred at −78° C. for 1 h. The reaction temperature was raised gradually to rt; and the mixture was stirred at rt overnight. To the mixture was added L-alanine methyl ester hydrochloride (6.29 g, 45.06 mmol, 1.0 eq.), followed by cooling the mixture to −78° C. under nitrogen atmosphere. Triethylamine (9.1 g, 90.12 mmol, 2.0 eq.) was then added dropwise to the cold mixture. The resulting mixture was stirred at −78° C. for 1 h. The temperature was raised gradually to rt; and the mixture was stirred at rt for 1 more hour, and then concentrated. The residue was purified (silica-gel column; eluent, pet-ether and ethyl acetate from 100:0 to 50:50), providing N-(chloro(indol-4-oxy)phosphinyl)-L-alanine methyl ester (9.2 g, 64.4%).

Axitinib (400 mg, 1.03 mmol, 1.0 eq.), DMF (12 mL), and N-(chloro(indol-4-oxy)phosphinyl)-L-alanine methyl ester (1.47 g, 4.65 mmol, 4.5 eq.), and triethylamine (0.575 g, 5.69 mmol, 5.5 eq.) were mixed in a flask and stirred at rt for 5 h. To the mixture were added water (50 mL) and ethyl acetate (70 mL) for extraction. The organic layer was separated, washed with brine (3×50 mL), and concentrated. The residue was purified (silica-gel column; eluent, DCM-methanol from 100:0 to 97:3), giving compound 61 (210 mg, 30.4%): 1H NMR (500 MHz, DMSO-d6) δ ppm: 1.31 (dd, J=60.5, 7.2 Hz, 3H), 2.76 (d, J=4.4 Hz, 3H), 3.46 (d, J=41.4 Hz, 3H), 4.37 (dt, J=17.5, 8.7 Hz, 1H), 6.49 (d, J=15.3 Hz, 1H), 6.75 (dd, J=34.7, 7.8 Hz, 1H), 6.88 (ddd, J=18.8, 13.3, 8.4 Hz, 2H), 7.07 (dt, J=25.2, 12.7 Hz, 1H), 7.15 (dd, J=14.2, 8.2 Hz, 1H), 7.30 (ddd, J=19.9, 14.5, 8.0 Hz, 5H), 7.48 (d, J=7.0 Hz, 1H), 7.68 (ddd, J=20.2, 14.7, 5.6 Hz, 2H), 7.81-7.94 (m, 2H), 8.11-8.25 (m, 2H), 8.39 (d, J=4.7 Hz, 1H), 8.64 (s, 1H), 11.22 (d, J=13.2 Hz, 1H); 13C NMR (125 MHz, DMSO-d6) δ ppm: 19.98, 20.62, 50.85, 52.32, 98.70, 109.51, 117.99, 120.92, 121.50, 122.15, 122.39, 122.55, 122.94, 123.77, 125.96, 126.62, 128.11, 128.35, 130.03, 130.81, 133.15, 134.90, 136.14, 137.14, 137.60, 138.41, 142.76, 145.46, 147.43, 150.25, 154.64, 168.30, 173.86; 31P NMR (203 MHz, DMSO-d6): δ ppm: −2.83, −2.39; m/z (ESI+): 667.4 (M+H).

Example 32: Synthesis of N-methyl-2-((1-((1S)-(9H-carbazol-4-oxy)(1-methoxycarbonylethyl))amino)phosphinyl-3-((1E)-2-(2-pyridinyl)ethenyl)-1H-indazol-6-yl)thio)benzamide (Compound 66)

4-Hydroxycarbazole (5 g, 27.29 mmol, 1.0 eq.) and DCM (200 mL), under protection of nitrogen atmosphere, were mixed in a flask and cooled to −78° C., followed by addition dropwise of phosphorus oxychloride (4.2 g, 27.29 mmol, 1.0 eq.) and triethylamine (2.76 g, 27.29 mmol, 1.0 eq.), subsequently. The mixture was stirred at −78° C. for 1 h; the temperature was gradually raised to rt. The mixture was further stirred at rt for 1 h. To the mixture at this point was added L-alanine methyl ester hydrochloride (3.81 g, 27.29 mmol, 1.0 eq.). The mixture was then cooled, under nitrogen atmosphere, to −78° C., followed by addition dropwise of triethylamine (5.51 g, 54.58 mmol, 2.0 eq.), and continued to be stirred at −78° C. for 1 h. The reaction temperature was raised gradually to rt. The mixture was stirred at rt for 1 h, and then concentrated. The residue was purified on a silica-gel column (eluent: pet-ether and ethyl acetate from 100:0 to 50:50), providing (4-carbazol-4-oxy)((1S)-(1-methoxycarbonylethyl)amino)phosphinyl chloride (4.1 g, 40.9%).

Axitinib (400 mg, 1.03 mmol, 1.0 eq.), DMF (12 mL), (4-carbazol-4-oxy)((1S)-(1-methoxycarbonylethyl)amino)phosphinyl chloride (1.89 g, 5.18 mmol, 5.0 eq.), and triethylamine (0.63 g, 6.18 mmol, 6.0 eq.) were mixed in a flask and stirred at rt for 5 h, followed by addition of water (50 mL) and ethyl acetate (70 mL). The organic layer was separated, washed with brine (3×50 mL), and concentrated. The residual material was purified (silica-gel column; eluent, DCM-methanol from 100:0 to 97:3), giving compound 67 (330 mg, 44.7%): 1H NMR (500 MHz, CDCl3) δ ppm: 1.31 (dd, J=87.4, 7.0 Hz, 3H), 2.81 (d, J=4.9 Hz, 3H), 3.54 (d, J=75.1 Hz, 3H), 4.20-4.59 (m, 2H), 6.39 (s, 1H), 7.07-7.25 (m, 9H), 7.37 (dd, J=21.4, 7.9 Hz, 3H), 7.49-7.62 (m, 2H), 7.71 (t, J=7.6 Hz, 1H), 7.81-7.89 (m, 2H), 8.14 (s, 1H), 8.39 (dd, J=11.8, 7.8 Hz, 1H), 8.48 (d, J=7.6 Hz, 1H), 8.66 (s, 1H); 13C NMR (125 MHz, $CDCl_3$) δ ppm: 20.85, 26.68, 50.62, 52.49, 108.22, 109.78, 110.66, 115.68, 119.71, 120.95, 121.21, 121.71, 122.02, 122.97, 123.21, 125.99, 126.35, 127.54, 128.61, 130.67, 132.85, 133.30, 136.76, 136.89, 137.83, 139.53, 141.59, 145.26, 148.37, 149.83, 154.78, 168.92, 173.63; 31P NMR (203 MHz, CDCl3): δ ppm: −1.70, −2.50; m/z (ESI+): 717.3 (M+H).

Example 33: Synthesis of N-methyl-2-((1-((1S)-(naphth-2-oxy)(1-methoxycarbonylethyl))amino)phosphinyl-3-((1E)-2-(2-pyridinyl)ethenyl)-1H-indazol-6-yl)thio)benzamide (Compound 90)

Under nitrogen protection, 2-naphthol (720 mg, 4.99 mmol, 1.0 eq.) and diethyl ether (20 mL) were mixed in a flask and cooled to −78° C., followed by addition of phosphorus oxychloride (765 mg, 4.99 mmol, 1.0 eq.) and triethylamine (504 mg, 4.99 mmol, 1.0 eq.) dropwise and subsequently. The stirred mixture was kept at −78° C. for 1 h, raising the reaction temperature gradually to rt, and kept at rt overnight. Insoluble material was removed by filtration; and the filtrate was concentrated to give naphth-2-yl dichlorophosphate (1.2 g, 92%).

Naphth-2-yl dichlorophosphate (1.1 g, 4.2 mmol, 1.0 eq.), DCM (30 mL), and L-alanine methyl ester hydrochloride (586 mg, 4.2 mmol, 1.0 eq.) were mixed in a flask. Under nitrogen atmosphere, the mixture was cooled to −78° C., followed by addition of triethylamine (848 mg, 8.4 mmol, 2.0 eq.) dropwise. The mixture was stirred at −78° C. for 1 h, and at rt for 1 h (after the reaction temperature was slowly raised to rt.). The mixture was concentrated; and the residual material was purified (silica-gel column; eluent, pet-ether and ethyl acetate from 100:0 to 50:50), providing N-(chloro(naphth-2-yl)phosphinyl)-L-alanine methyl ester (790 mg, 57%).

Axitinib (200 mg, 0.518 mmol, 1.0 eq.), DMF (4 mL), N-(chloro(naphth-2-yl)phosphinyl)-L-alanine methyl ester (186.5 mg, 0.569 mmol, 1.1 eq.), and triethylamine (131.9 mg, 1.29 mmol, 2.5 eq.) were mixed in a flask and stirred at rt for 5 h. To the mixture were added water (20 mL) and ethyl acetate (30 mL). The organic layer was separated, washed with brine (3×30 mL), and concentrated. Purification of the residual material on a silica-gel column (eluent, DCM-methanol from 100:0 to 100:5) gave compound 90 (126.1 mg, 34%): 1H NMR (500 MHz, CDCl3): δ 1.48 (dd, J=41.1, 6.6 Hz, 3H), 2.72-2.92 (m, 3H), 3.65 (dd, J=72.4, 1.6 Hz, 3H), 4.28-4.78 (m, 2H), 6.53 (s, 1H), 7.25 (ddd, J=26.1, 11.7, 4.9 Hz, 6H), 7.45 (t, J=8.0 Hz, 2H), 7.56 (s, 1H), 7.59-7.66 (m, 2H), 7.66-7.74 (m, 3H), 7.79 (dd, J=16.1, 8.2 Hz, 2H), 7.85-7.99 (m, 2H), 8.11 (d, J=6.9 Hz, 1H), 8.69 (s, 1H); 13C NMR (125 MHz, CDCl3): δ 21.00, 26.66, 50.66, 52.65, 115.53, 117.40, 120.22, 121.32, 122.83, 123.20, 125.82, 126.26, 126.85, 127.75, 128.97, 129.95, 130.80, 131.13, 132.31, 133.04, 133.24, 133.70, 136.78, 137.74, 137.92, 138.11, 145.44, 147.37, 148.22, 149.23, 149.40, 154.51, 168.73, 173.71; 31P NMR (203 MHz, CDCl3): δ −2.75, −1.99; m/z (ESI+): 678.2 (M+H).

Example 34: Synthesis of N-methyl-2-((1-(1-oxo-2,5,8,11,14,17,20,23-octaoxatetracos-1-yl)-3-((1E)-2-(2-pyridinyl)ethenyl)-1H-indazol-6-yl)thio)benzamide (Compound 94)

Heptaethylene glycol monomethyl ether (400 mg, 1.17 mmol, 1.0 eq.), THF (5 mL), and triethylamine (177.59 g, 1.76 mmol, 1.5 eq.) were mixed in a flask and cooled to 0° C. in an ice water bath, followed by addition of a solution of p-nitrophenyl chloroformate (258.69 mg, 1.29 mmol, 1.1 eq.) in THF (5 mL) dropwise. The reaction temperature was raised to rt; the mixture was stirred at rt for 4 h, and then concentrated. The residual material was purified on a silica-gel column (eluent: pet-ether and ethyl acetate from 100:0 to 70:30), giving 3,6,9,12,15,18,21-heptaoxadocos-1-yl p-nitrophenyl carbonate (400 mg, 67.8%).

In a flask were mixed axitinib (280 mg, 0.72 mmol, 1.0 eq.), DMF (10 mL), and triethylamine (145.44 mg, 1.44 mmol, 2.0 eq.). The mixture was stirred at rt while 3,6,9,12,15,18,21-heptaoxadocos-1-yl p-nitrophenyl carbonate (400.0 mg, 0.79 mmol, 1.1 eq.) was added. The mixture was stirred at rt for 16 h, followed by addition of water (100 mL) and ethyl acetate (120 mL). The organic layer was separated, washed with brine (3×70 mL), and concentrated. The residual material was purified (silica-gel column; eluent, DCM-methanol from 100:0 to 100:3), giving compound 94 (310 mg, 57%): 1H NMR (500 MHz, DMSO-d6): δ 2.76 (d, J=4.6 Hz, 3H), 3.21 (s, 3H), 3.38-3.49 (m, 20H), 3.50-3.56 (m, 2H), 3.57-3.64 (m, 2H), 3.75-3.88 (m, 2H), 4.46-4.65 (m, 2H), 7.16 (d, J=7.3 Hz, 1H), 7.37 (ddd, J=16.0, 14.5, 7.9 Hz, 4H), 7.52 (dd, J=7.1, 1.6 Hz, 1H), 7.74-7.82 (m, 2H), 7.85 (dt, J=7.6, 3.8 Hz, 1H), 7.92 (d, J=16.4 Hz, 1H), 8.19 (s, 1H), 8.31 (d, J=8.4 Hz, 1H), 8.38 (d, J=4.5 Hz, 1H), 8.65 (d, J=4.3 Hz, 1H); 13C NMR (125 MHz, DMSO-d6): δ 26.52, 58.47, 67.32, 68.50, 70.17, 71.71, 117.50, 121.50, 122.81, 123.62, 123.97, 127.38, 128.41, 130.89, 131.51, 134.54, 134.76, 137.51, 137.85, 138.33, 147.57, 150.25, 154.30, 168.18; m/z (ESI+): 753.6 (M+H).

Example 35: Synthesis of N-methyl-2-((1-((1S)-(2-methylbenzyloxy)(1-methoxycarbonylethyl))amino) phosphinyl-3-((1E)-2-(2-pyridinyl)ethenyl)-1H-indazol-6-yl)thio)benzamide (Compound 95)

Under nitrogen protection, phosphorus oxychloride (1.9 g, 12.3 mmol, 1.0 eq.) and DCM (50 mL) were placed in a flask and cooled to −78° C., followed by addition, to the cold mixture, of 2-methylbenzyl alcohol (1.5 g, 12.3 mmol, 1.0 eq.) and a solution of triethylamine (1.2 g, 12.3 mmol, 1.0 eq.) in DCM (20 mL). The mixture was stirred at −78° C. for 3 h, followed by addition of L-alanine methyl ester hydrochloride (1.5 g, 11.1 mmol, 0.9 eq.) under nitrogen atmosphere at −78° C., and by addition dropwise of triethylamine (2.5 g, 24.6 mmol, 2.0 eq.). The mixture was stirred at −78° C. for 1.5 h. Then reaction temperature was raised slowly to rt, and the mixture was stirred for one more hour at rt. The mixture was cooled to 0° C., followed by addition of pentafluorophenol (1.6 g, 8.88 mmol, 0.8 eq.) and triethylamine (1.1 g, 11.1 mmol, 1.0 eq.). This mixture was stirred at rt for 1 h, and then treated with brine (30 mL). The organic layer was separated, filtered, and concentrated. The residual material was purified on a silica-gel column (eluent: pet-ether and ethyl acetate, from 100:0 to 35:65), giving N-((2-methylbenzyloxy)(pentefluorophenoxy)phosphinyl)-L-alanine methyl ester (2.8 g, 71.9%).

In a flask were added axitinib (400 mg, 1.0 mmol, 1.0 eq.), DMF (15 mL), and N-((2-methylbenzyloxy)(pentefluorophenoxy)phosphinyl)-L-alanine methyl ester (563 mg, 1.2 mmol, 1.2 eq.), followed by addition dropwise of DBU (183 mg, 1.2 mmol, 1.2 eq.). The mixture was stirred at rt for 0.5 h, and then treated with water (10 mL) and ethyl acetate (30 mL). The organic layer was separated, washed with brine (3×10 mL), and concentrated. The residual material was purified using a silica-gel column (eluent: DCM-methanol, from 100:0 to 97:3), giving compound 95 (328 mg, 50.0%): 1H NMR (500 MHz, CDCl3): δ ppm 1.27-1.43 (m, 3H), 2.31 (d, J=2.7, 3H), 2.91 (t, J=4.5, 3H), 3.58 (d, J=66.0, 3H), 3.96-4.39 (m, 2H), 4.97 (td, J=12.2, 7.0, 1H), 5.07-5.26 (m, 1H), 6.53 (s, 1H), 7.09 (dd, J=16.9, 8.9, 2H), 7.14-7.26 (m, 4H), 7.32 (d, J=2.5, 3H), 7.47 (d, J=7.7, 1H), 7.54-7.67 (m, 2H), 7.73 (t, J=7.4, 1H), 7.79-7.98 (m, 2H), 8.13 (d, J=18.3, 1H), 8.65 (d, J=4.1, 1H); 13C NMR (125 MHz, CDCl3): δ ppm 18.8, 20.81, 26.67, 50.22, 52.40, 67.59, 116.03, 121.16, 122.57, 122.85, 125.93, 126.38, 127.42, 127.46, 128.78, 128.93, 129.29, 130.33, 132.65, 132.90, 132.95, 133.65, 133.77, 136.18, 136.78, 137.04, 137.74, 145.05, 147.84, 149.80, 154.74, 168.70, 173.81; 31P NMR (203 MHz, CDCl3): δ ppm 1.43, 2.03; m/z (ESI+): 656.2 (M+H).

Example 36: Synthesis of N-methyl-2-((1-((1S)-(naphthoxy)(1-(1S-1-phenylethoxycarbonyl)ethyl))amino)phosphinyl-3-((1E)-2-(2-pyridinyl)ethenyl)-1H-indazol-6-yl)thio)benzamide (Compound 96)

In a flask were placed N-(t-Boc)-L-alanine (2 g, 10.57 mmol, 1.0 eq.), DDC (2.61 g, 12.69 mmol, 1.2 eq.), DMAP (1.29 g, 10.57 mmol, 1.0 eq.), and acetonitrile (20 mL); and the mixture was stirred at rt for 20 min., followed by addition of (S)-(−)-1-phenylethanol (1.29 g, 10.57 mmol, 1.0 eq.) dropwise. The mixture was stirred overnight at rt, and filtered to remove insoluble material. The filtrate was concentrated; and the residue was purified on a silica-gel column (eluent: pet-ether and ethyl acetate, from 100:0 to 20:80), providing N-(tert-butoxycarbonyl)-L-alanine (S)-1-phenylethyl ester (2.8 g, 90.2%). This ester (2.8 g, 9.54 mmol, 1.0 eq.) was treated in a solution of 4M HCl in dioxane (15 mL, 6.3 eq.) diluted with dioxane (10 mL) by stirring at rt for 3 h. Concentration of the reaction solution gave L-alanine (S)-1-phenylethyl ester hydrochloride salt (2.1 g, 95.8%).

Naphthol (313.7 mg, 2.18 mmol, 1.0 eq.) and DCM (30 mL) were loaded in a flask, cooled to −78° C. under nitrogen atmosphere, followed by addition of phosphorus oxychloride (334 mg, 2.176 mmol, 1.0 eq.) and triethylamine (220 mg, 2.176 mmol, 1.0 eq.) subsequently and dropwise. The mixture was stirred at −78° C. for 1 h; and the temperature of the reaction was raised to rt. The mixture was further stirred at rt overnight, followed by addition of (S)-1-phenylethyl ester hydrochloride salt (499.8 mg, 2.176 mmol, 1.0 eq.) under nitrogen protection. After the mixture was cooled to −78° C., triethylamine (437.25 mg, 4.352 mmol, 2.0 eq.) was introduced dropwise. The mixture was stirred at −78° C. for 1 h; and the temperature of the reaction was raised to rt. The mixture was further stirred at rt for 1 h, followed by addition of pentafluorophenol (400 mg, 2.176 mmol, 1.0 eq.). Under nitrogen atmosphere, the reaction mixture was cooled to −78° C.; and triethylamine (220 mg, 2.176 mmol, 1.0 eq.) was added dropwise. The resultant mixture was stirred at −78° C. for 1 h, warmed to rt gradually, and stirred at rt for 1 h, and then concentrated. The residual material was purified (silica-gel column; eluent, pet-ether and ethyl acetate from 100:0 to 80:20), giving N-chloro(naphth-1-yloxy)(pentafluorophenoxy)phosphonyl-L-alanine (S)-1-phenylethyl ester (450 mg, 36.6%).

Axitinib (256.3 mg, 0.663 mmol, 1.0 eq.), DMF (12 mL), and DBU (121.2 mg, 0.796 mmol, 1.2 eq.) were mixed in a flask and cooled to −20° C., followed by addition a solution of N-chloro(naphth-1-yloxy)(pentafluorophenoxy)phosphonyl-L-alanine (S)-1-phenylethyl ester (450 mg, 0.796 mmol, 1.2 eq.) in DMF (1 mL). The mixture was stirred at −20° C. for 40 min, followed by addition of water (50 mL) and ethyl acetate (70 mL). The organic layer was separated, washed with brine (3×50 mL), and concentrated. The residue was purified (silica-gel column; eluent, DCM and methanol from 100:0 to 97:3), giving compound 96 (300 mg, 58.9%): 1H NMR (500 MHz, DMSO-d6) δ ppm: 1.14-1.40 (m, 6H), 2.76 (d, J=4.3 Hz, 3H), 4.30-4.52 (m, 1H), 5.56-5.72 (m, 1H), 6.83-6.94 (m, 1H), 7.15-7.43 (m, 12H), 7.49 (d, J=4.9 Hz, 1H), 7.53-7.74 (m, 5H), 7.80-7.96 (m, 3H), 8.12-8.24 (m, 2H), 8.24-8.30 (m, 1H), 8.40 (s, 1H), 8.63 (s, 1H); 13C NMR (125 MHz, DMSO-d6) δ ppm: 19.41, 22.01, 26.13, 50.22, 72.56, 115.12, 117.15, 121.59, 121.77, 122.15, 122.47, 123.25, 125.16, 125.54, 125.76, 126.24, 126.36, 126.52, 126.92, 127.60, 127.88, 128.27, 128.34, 129.71, 130.29, 132.81, 134.28, 134.89, 135.44, 136.83, 137.06, 141.42, 144.90, 145.58, 147.33, 149.74, 154.03, 167.79, 171.91; 31P NMR (203 MHz, DMSO-d6): δ ppm: −2.26, −1.76; m/z (ESI+): 768.5 (M+H).

Example 37: Synthesis of N-methyl-2-((1-((5-methyl-2-oxo-1,3-dioxol-4-yl)methoxycarbonyl)-3-((1E)-2-(2-pyridinyl)ethenyl)-1H-indazol-6-yl)thio)benzamide (Compound 97)

(5-Methyl-2-oxo-1,3-dioxol-4-yl)methanol (500 mg, 3.84 mmol, 1.0 eq.), DCM (10 mL), and triethylamine (0.78 g, 7.68 mmol, 2.0 eq.) were mixed in a flask and the mixture was cooled to 0° C. in an ice-water bath. To the cold mixture was added a solution of p-nitrophenyl chloroformate (0.78 g, 7.68 mmol, 1.5 eq.) in DCM (10 mL) dropwise. The mixture was warmed to rt, stirred at rt for 16 h, and then concentrated to remove most of the solvent. The residue was purified (silica-gel column; eluent, pet-ether and ethyl acetate from 100:0 to 50:50), providing 5-methyl-2-oxo-1,3-dioxol-4-yl)methyl p-nitrophenyl carbonate (600 mg, 54%).

Axitinib (400 mg, 1.04 mmol, 1.0 eq.), DMF (6 mL), and triethylamine (157 mg, 1.56 mmol, 1.5 eq.) were stirred in a flask, followed by addition of 5-methyl-2-oxo-1,3-dioxol-4-yl)methyl p-nitrophenyl carbonate (366 mg, 1.24 mmol, 1.2 eq.). The mixture was stirred at rt for 16 h, followed by addition of water (20 mL) and ethyl acetate (30 mL). The organic layer was separated, washed with brine (3×30 mL), and concentrated. The residual material was purified on a silica-gel column (eluent, DCM-methanol from 100:0 to 100:3), giving compound 97 (355 mg, 54%): 1H NMR (500 MHz, DMSO-d6): δ 2.25 (s, 3H), 2.76 (d, J=4.3 Hz, 3H), 5.40 (s, 2H), 7.19 (s, 1H), 7.37 (s, 3H), 7.42 (d, J=8.2 Hz, 1H), 7.51 (s, 1H), 7.75-7.84 (m, 2H), 7.87 (s, 1H), 7.93 (d, J=16.0 Hz, 1H), 8.16 (s, 1H), 8.32 (d, J=8.2 Hz, 1H), 8.40 (s, 1H), 8.66 (s, 1H); 13C NMR (125 MHz, DMSO-d6): δ 9.47, 26.53, 57.47, 117.08, 121.27, 122.89, 123.63, 124.40, 124.11, 127.55, 128.44, 130.89, 131.75, 133.08, 134.17, 134.98, 137.55, 138.20, 138.60, 141.46, 141.66, 147.83, 149.92, 150.23, 152.24, 154.21, 168.18; m/z (ESI+): 543.0 (M+H).

Example 38: Synthesis of N-methyl-2-((1-(2-hydroxyethoxycarbonyl)-3-((1E)-2-(2-pyridinyl)ethenyl)-1H-indazol-6-yl)thio)benzamide (compound 48) and its hydrochloride (Compound 98)

A mixture of ethylene glycol (4.2 g, 71.7 mmol, 5.0 eq.), DCM (40 mL), triethylamine (1.15 g, 11.3 mmol, 2.0 eq.), tert-butyldimethylsilyl chloride (2 g, 13.3 mmol, 1.0 eq), and 4-dimethylaminopyridine (322 mg, 2.66 mmol, 0.2 eq) was stirred at rt for 16 h, and concentrated to remove the solvent. The residual material was purified on a silica-gel column (eluent: per-ether and ethyl acetate from 100:0 to 80:20), providing 2-(tert-butyldimethylsilyloxy)ethanol (1.93 g, 82%).

2-(tert-Butyldimethylsilyloxy)ethanol (1.93 g, 11.0 mmol, 1.0 eq.) was mixed with DCM (10 mL) and triethylamine (2.22 g, 22.0 mmol, 2.0 eq.) in a flask and cooled to 0° C. in an ice-water bath. To the cold mixture was added a solution of p-nitrophenyl chloroformate (2.65 g, 13.2 mmol, 1.2 eq.) in DCM (10 mL) dropwise. After the reaction temperature was raised to rt, the mixture was stirred at rt for 16 h. The mixture was concentrated; and the residual material was extracted between ethyl acetate and water (40 mL each). The organic layer was separated and concentrated to a residue. The residual material was purified (silica-gel column; eluent, pet-ether and ethyl acetate from 100:0 to 80:20), giving 2-(tert-butyldimethylsilyloxy)ethyl p-nitrophenyl carbonate (3 g, 81%). Axitinib (400 mg, 1.04 mmol, 1.0 eq.), DMF (6 mL), and triethylamine (79 mg, 2.08 mmol, 2.0 eq.) were mixed in a flask and stirred, followed by addition of 2-(tert-butyldimethylsilyloxy)ethyl p-nitrophenyl carbonate (424 mg, 1.25 mmol, 1.2 eq.). The mixture was stirred at rt for 16 h, followed by addition of water (20 mL) and ethyl acetate (30 mL). The organic layer was separated, washed with brine (3×30 mL), and concentrated. The residual material was purified (silica-gel column; eluent, DCM-methanol from 100:0 to 100:3), giving N-methyl-2-((1-(2-(tert-butyldimetylsilyoxyethoxycarbonyl)-3-((1E)-2-(2-pyridinyl)ethenyl)-1H-indazol-6-yl)thio)benzamide (600 mg, 98%) as silyl-protected intermediate. The intermediate (600 mg) was stirred in ethanol (10 mL) containing concentrated HCl (0.1 mL) at rt for 3 h. The solid material was collected by filtration, dissolved in water, and freeze-dried, giving compound 98 (290 mg, 56%): 1H NMR (500 MHz, DMSO-d6): δ 2.75 (d, J=4.4 Hz, 3H), 3.55-3.88 (m, 2H), 4.36-4.64 (m, 2H), 7.21 (d, J=7.1 Hz, 1H), 7.38 (dd, J=10.2, 5.5 Hz, 3H), 7.53 (d, J=7.1 Hz, 1H), 7.73-7.86 (m, 1H), 8.01 (d, J=16.7 Hz, 1H), 8.13 (s, 1H), 8.25-8.35 (m, 2H), 8.43 (dd, J=22.1, 3.9 Hz, 3H), 8.80 (d, J=5.2 Hz, 1H); 13C NMR (125 MHz, DMSO-d6): δ 26.54, 59.24, 70.07, 116.96, 122.47, 123.24, 124.78, 125.72, 127.14, 127.74, 128.12, 128.48, 130.94, 132.13, 133.77, 138.57, 138.91, 141.39, 143.95, 144.19, 146.31, 150.35, 168.28; m/z (ESI+): 475.1 (M+H).

Compound 98 (1.0 g, 1.7 mmol, 1.0 eq.) was dissolved in water (20 mL), followed by addition of DCM (100 mL). The pH of the mixture was adjusted to 7-8 with aq. $NaHCO_3$. Solid material was removed by precipitation. MeOH (20 mL) was added dropwise to the mixture. The organic layer was separated, washed with brine (3×20 mL), dried ($Na_2SO_4$), and evaporated to dryness. The residue was triturated with MTBE (30 mL) and filtered to afford compound 48 as a white solid (600 mg, 74.5%): $^1H$ NMR (500 MHz, DMSO-$d_6$): δ 2.75 (d, J=4.4 Hz, 3H), 3.74 (d, J=4.2 Hz, 2H), 4.47 (s, 2H), 5.07 (t, J=5.4 Hz, 1H), 7.18 (d, J=6.9 Hz, 1H), 7.38 (dd, J=16.8, 7.2 Hz, 4H), 7.52 (d, J=5.2 Hz, 1H), 7.78 (t, J=11.9 Hz, 2H), 7.86 (t, J=6.8 Hz, 1H), 7.93 (d, J=16.4 Hz, 1H), 8.17 (s, 1H), 8.31 (d, J=8.4 Hz, 1H), 8.43 (d, J=4.5 Hz, 1H), 8.65 (d, J=3.0 Hz, 1H); $^{13}C$ NMR (125 MHz, DMSO-$d_6$): δ 26.16, 58.89, 69.45, 116.88, 121.07, 122.35, 123.13, 123.57, 127.10, 127.74, 128.04, 130.54, 131.34, 133.91, 134.23, 137.11, 137.49, 138.14, 140.97, 147.00, 149.92, 153.88, 167.88; m/z (ESI+): 475.1 (M+H).

Example 39: Pharmacokinetic Studies (a)

Test articles were prepared in suspension in a mixture of DMSO (5%) and 0.5%-CMC-Na (95%, v/v), at a concentration of 3 mg/mL axitinib-molar-equivalence for each test article. Male ICR mice (64, body weight ranging 18-22 g) were grouped randomly in 4 groups (16 animals per group). Test articles were administered to animals through oral-gavage, at a dose of molar-equivalent to 30 mg/kg of axitinib, after the animals were fasted for 12 h. Blood samples were collected from orbit to heparinized EP tube at time points of 0.25, 0.5, 1, 2, 4, 6, and 8 h following the administration of the dosing solution. Blood samples were centrifuged at 5,000 rpm and 4° C. for 10 min, and plasma samples were collected and kept at −80° C. Sample analysis: Plasma sample (10 μL) was mixed well with acetonitrile (110 μL). The sample was then centrifuged at 12,000 rpm and 4° C. The supernatant was analyzed with an LC-MS/MS instrument, and the target analytes were axitinib and its corresponding prodrug molecules. The axitinib plasma concentration-time curves are given in FIG. 1 after oral administration of axitinib, compounds 1, 5, and 10 to the animals.

Example 40: Pharmacokinetic Studies (b)

Male ICR mice (body weight: 18 to 22 g) were divided into 6 groups randomly with 6 animals per group, with blood sample collection from 6 animals at each time point for a total of 6 time points. Dosing solution of a test article was prepared by dissolving or suspending a compound in a solvent system as indicated in Table 2. For all the compounds, the concentration of dosing solution was 3 mg/mL of axitinib molar equivalent, and the dose was 30 mg/kg of axitinib molar equivalent. Animals were fasted for 12 h, and then given the test article in dosing media at a dosing volume calculated according to the above information. After dosing, blood samples were collected at the pre-set time points of 0.5, 1, 2, 4, 6, and 8 h. Blood samples were centrifuged at 5,000 rpm and 4° C. for 10 min, and plasma samples were collected and kept at −80° C. Sample analysis: Plasma sample (20 μL) was mixed well with acetonitrile (220 μL). The sample was then centrifuged at 12,000 rpm and 4° C. The supernatant was analyzed with an LC-MS/MS instrument, and the target analytes were axitinib and its corresponding prodrug molecules. Table 2 gives pharmacokinetic parameters for some test compounds following administration of the corresponding prodrugs to the animals.

TABLE 2

PK parameters for axitinib following administration of prodrugs to the animals.

| Compd number | $AUC_{(0-t)}$ (ug/L*h) | t½z (h) | Tmax (h) | Vz/F (L/kg) | CLz/F (L/h/kg) | Cmax (ug/L) | Solvent media* |
|---|---|---|---|---|---|---|---|
| 2 | 19 | 6 | 6 | 7090 | 820 | 4 | B |
| 3 | 554 | 4 | 2 | 237 | 38 | 103 | A |
| 4 | 1431 | 3 | 4 | 70 | 18 | 298 | A |
| 6 | 64 | 6 | 2 | 2265 | 243 | 12 | B |
| 7 | 4978 | 2 | 1 | 14 | 6 | 2455 | C |
| 8 | 1753 | 3 | 1 | 65 | 13 | 366 | C |
| 11 | 2729 | 2 | 1 | 29 | 10 | 1009 | D |
| 12 | 1856 | 1 | 2 | 25 | 16 | 469 | E |
| 13 | 2725 | 1 | 1 | 16 | 11 | 736 | B |
| 15 | 3485 | 1 | 0.8 | 9 | 6 | 1210 | E |
| 17 | 3901 | 1 | 1.3 | 8 | 5 | 1232 | B |
| 19 | 5515 | 1 | 0.8 | 5 | 4 | 2391 | B |
| 22 | 300 | 2.2 | 146 | 82 | 75 | 300 | B |
| 39 | 2179 | 1 | 1.3 | 14 | 9 | 679 | B |
| 44 | 1187 | 1.4 | 0.6 | 32.3 | 17 | 556 | B |
| 45 | 693 | 2.4 | 0.4 | 96 | 27 | 429 | B |
| 46 | 491 | 2.6 | 0.4 | 158 | 41 | 322 | B |
| 48 | 7340.25 | 1.0 | 1.2 | 7.4 | 5 | 2888 | F |
| 49 | 10169 | 1.5 | 0.4 | 5.0 | 2 | 7474 | B |
| 50 | 9389 | 1 | 0.4 | 3.5 | 2 | 5818 | B |
| 51 | 4162 | 1 | 0.4 | 7.6 | 5 | 3340 | B |
| 67 | 3156 | 1.3 | 3 | 12.5 | 7 | 785 | B |
| 92 | 11342 | 0.8 | 0.4 | 2.1 | 1.9 | 5260 | B |
| 98 | 6394 | 0.8 | 0.7 | 5.75 | 4.96 | 2732 | B |

*A: 0.5% CMC-Na; B: 5% DMSO and 95% 0.5%-CMC-Na; C: 2% DMSO, 10% EtOH, and 88% 0.5% CMC-Na; D: 10% DMSO and 90% 0.5%-CMC-Na; E: 2% DMSO and 98% 0.5%-CMC-Na; F: 5% DMSO + 93% (0.5% CMC-Na) + 2% HCOOH.

Figure 2:
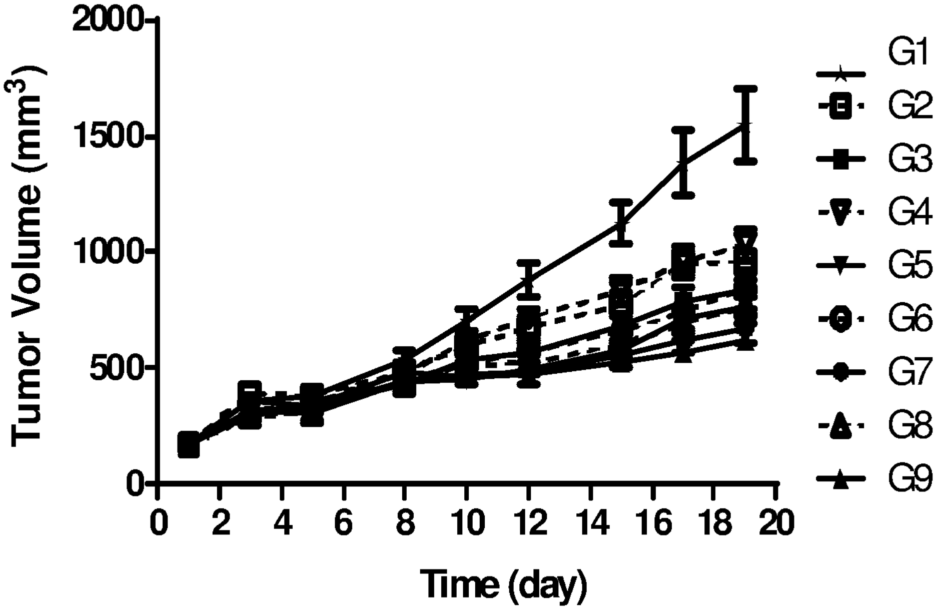
FIG. 2 gives tumor volumes ($mm^3$) from the control group and all the treatment groups at the end of 19-day treatment: all the doses refer to a molar equivalent dose for axitinib; G1, Control; G2, axitinib—10 mg/kg; G3, axitinib—30 mg/kg, G4, compound 1—10 mg/kg; G5, compound 1—30 mg/kg; G6, compound 5—10 mg/kg; G7, compound 5—30 mg/kg; G8, compound 10—10 mg/kg; G9, compound 10—30 mg/kg.
Figure 3:
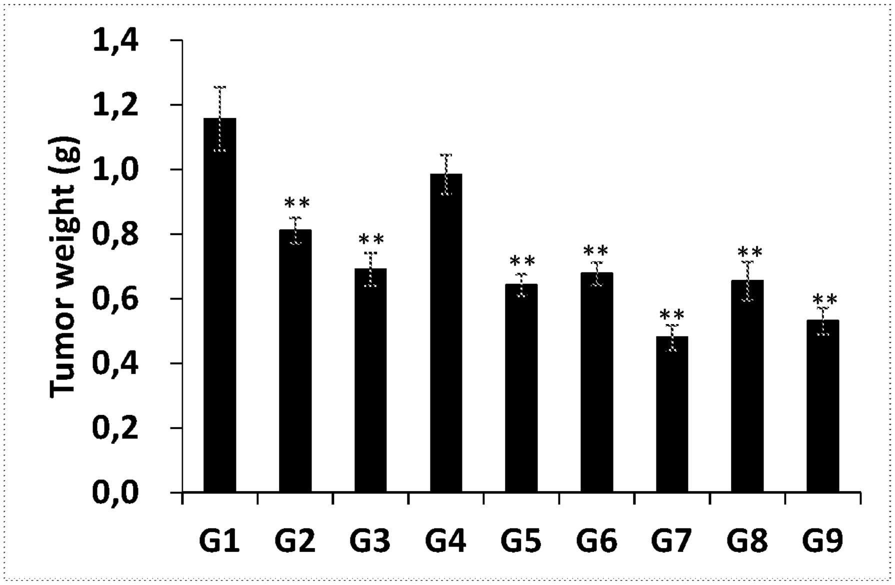
FIG. 3 shows a bar-graph representing average tumor weights (g) from different animal groups (control group and all the treatment groups) at the end of 19-day treatment: all the doses refer to an molar equivalent dose for axitinib; G1, Control; G2, axitinib—10 mg/kg; G3, axitinib—30 mg/kg, G4, compound 1—10 mg/kg; G5, compound 1—30 mg/kg; G6, compound 5—10 mg/kg; G7, compound 5—30 mg/kg; G8, compound 10—10 mg/kg; G9, compound 10—30 mg/kg.

Example 41: Anti-Tumor Activity of Selected Compounds in an EN1903-3 HT-29 Animal Model The HT29 model was created using male Balb/c Nude mice, 16-18 g body weight, (Balb/c Nude mice, SPF grade from Shanghai Qinlong Biotechnology Co., Ltd., Shanghai, China), as follows: a) HT29 cells were cultured and expanded until enough cells were obtained, then the cells were collected; b) HT29 cells were suspended in serum-free M5A culture media at a concentration of $3.0\times10^7$ cells/mL, total 15 mL; c) A total of 130 Balb/c nude mice were subcutaneously inoculated with 0.1 mL cell suspension per mouse (or $3.0\times10^6$ cells/mouse). After the tumor reached 100 $mm^3$ to 200 $mm^3$ in size, 90 animals with adequate tumor sizes were grouped randomly (10 animals per group), and assigned to day 1. Each group was given a number as follows: G1, Control; G2, axitinib at 10 mg/kg; G3, axitinib at 30 mg/kg; G4, compound 1 at 10 mg/kg molar equivalent of axitinib; G5, compound 1 at 30 mg/kg of molar equivalent of axitinib; G6, compound 5 at 10 mg/kg molar equivalent of axitinib; G7, compound 5 at 30 mg/kg molar equivalent of axitinib; G8, compound 10 at 10 mg/kg molar equivalent of axitinib; G9, compound 10 at 30 mg/kg of molar equivalent of axitinib. All the test articles were dosed in dosing media of 5% DMSO+95%(0.5% CMC-Na) through oral gavage at a dosing volume of 10 mL/kg. During the first 7 days (day 1 to day 7), the animals were treated with the test article once a day (QID). From day 8, the treatment was twice daily (BID) until day 19, when the study was terminated. On day 19, the tumor size and weight were measured and recorded. The average tumor size and weight for each group is given in FIG. 2 and FIG. 3. No animal death was observed during the entire study period for all groups.

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. A compound of Formula I, or a pharmaceutically acceptable salt or ester thereof:

(I)

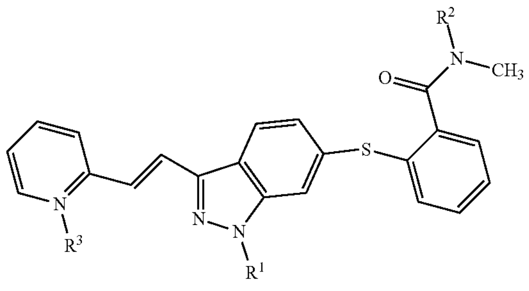

where, $R^1$ and $R^2$ are independently a hydrogen or a protecting group, wherein the protecting group is $R^4W(R^5R^6C)_m$—, where m is an integer selected from 0 to 6; W is absent; $R^5$ and $R^6$ are independently a hydrogen or a lower alkyl group; and (a) $R^4$ is

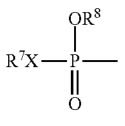 or 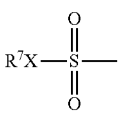 , where X is oxygen (—O—), sulfur (—S—), nitrogen (—NH—), or a methylene (—$CH_2$—) group; $R^7$ and $R^8$ are independently a hydrogen, a substituted or unsubstituted alkyl or cycloalkyl, an aryl or heteroaryl group without or with substitution, a PEG moiety, or an ester-forming group; or, the combination of $R^7$ and X is an aryl group with or without further substitution; or (b) $R^4$ is

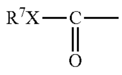 , where $R^7$ is a PEG moiety and X is O, S, NH or —$CH_2$—;

and $R^3$ is absent or a protecting group selected from acyl group, carbonyl group, thiocarbonyl group, carbamoyl group, substituted or unsubstituted acetyl, substituted or unsubstituted aminoalkanoyl, substituted or unsubstituted α-aminoalkanoyl, an acyl group derived from a natural or an unnatural amino acid with or without substitution, an acyl group of a peptide residue, cycloalkane-carbonyl, heterocycloalkane-carbonyl, alkoxycarbonyl, aryloxycarbonyl, heteroalkoxycarbonyl, and heteroaryloxycarbonyl;

provided that the compound of Formula I is not axitinib.

2. A compound of Formula II, or a pharmaceutically acceptable salt or ester thereof:

(II)

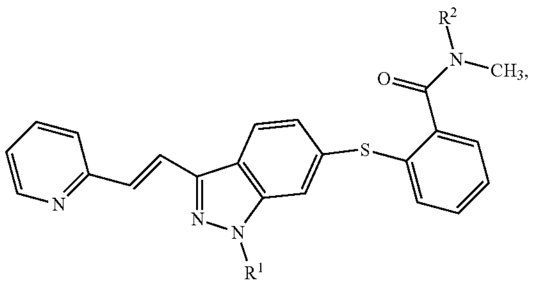

where, $R^1$ and $R^2$ are independently a hydrogen or a protecting group, wherein:

the protecting group is $R^4W(R^5R^6C)_m$—, where m is an integer selected from 0 to 6; W is oxygen (—O—), sulfur (—S—), nitrogen (—NH—), or absent; $R^5$ and $R^6$ are independently a hydrogen or a lower alkyl group; and (a) $R^4$ is

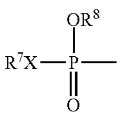 or 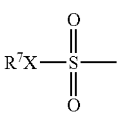 , where X is oxygen (—O—), sulfur (—S—), nitrogen (—NH—), or a methylene (—$CH_2$—) group; $R^7$ and $R^8$ are independently a hydrogen, a substituted or unsubstituted alkyl or cycloalkyl, an aryl or heteroaryl group without or with substitution, a PEG moiety, or an ester-forming group; or, the combination of $R^7$ and X is an aryl group with or without further substitution;

provided that when $R^4$ is

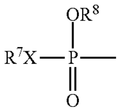

and X is O, then $R^7$ and $R^8$ are not both hydrogen;

or (b) $R^4$ is

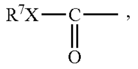

where $R^7$ is a PEG moiety and X is O, S, NH or $-CH_2-$;

provided that the compound of Formula II is not axitinib.

3. The compound of claim 2, wherein the PEG moiety is $R^{10}-(OCH_2CH_2)_n-$, where n is 1 to 10, and $R^{10}$ is a hydrogen or a lower alkyl.

4. The compound of claim 2, wherein the ester-forming group is a lower alkyl or an aryl group.

5. A compound of Formula III, or a pharmaceutically acceptable salt or ester thereof:

(III)

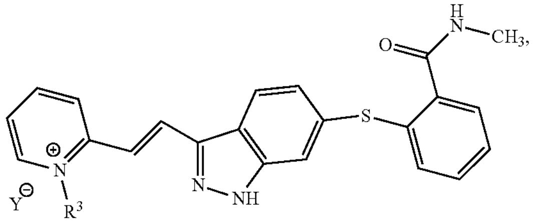

where, $R^3$ is absent or a protecting group, wherein:

(a) the protecting group is selected from acyl group, carbonyl group, thiocarbonyl group, carbamoyl group, substituted or unsubstituted acetyl, substituted or unsubstituted aminoalkanoyl, substituted or unsubstituted a-aminoalkanoyl, an acyl group derived from a natural or an unnatural amino acid with or without substitution, an acyl group of a peptide residue, cycloalkane-carbonyl, heterocycloalkane-carbonyl, alkoxycarbonyl, aryloxycarbonyl, heteroalkoxycarbonyl, and heteroaryloxycarbonyl;

or (b) the protecting group is $R^4W(R^5R^6C)_m-$, where m is an integer selected from 0 to 6; W is oxygen (—O—), sulfur (—S—), nitrogen (—NH—), or absent; $R^5$ and $R^6$ are independently a hydrogen or a lower alkyl group; and $R^4$ is

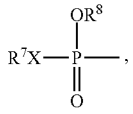 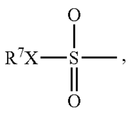 or 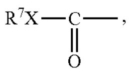

where X is oxygen (—O—), sulfur (—S—), nitrogen (—NH—), or a methylene ($-CH_2-$) group; $R^7$ and $R^8$ are independently a hydrogen, a substituted or unsubstituted alkyl or cycloalkyl, an aryl or heteroaryl group without or with substitution, a PEG moiety, or an ester-forming group; or, the combination of $R^7$ and X is an alkyl or aryl group with or without further substitution;

$Y^{\ominus}$ is a counterion;

provided that the compound of Formula III is not axitinib.

6. The compound of claim 5, wherein the PEG moiety is $R^{10}-(OCH_2CH_2)_n-$, where n is 1 to 10, and $R^{10}$ is a hydrogen or a lower alkyl.

7. The compound of claim 5, wherein the ester forming group is a lower alkyl or an aryl group.

8. A compound which is:

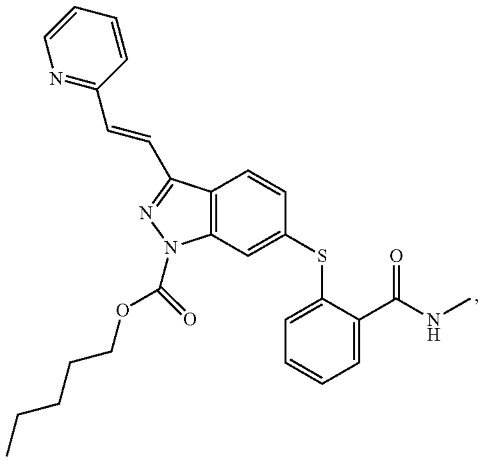

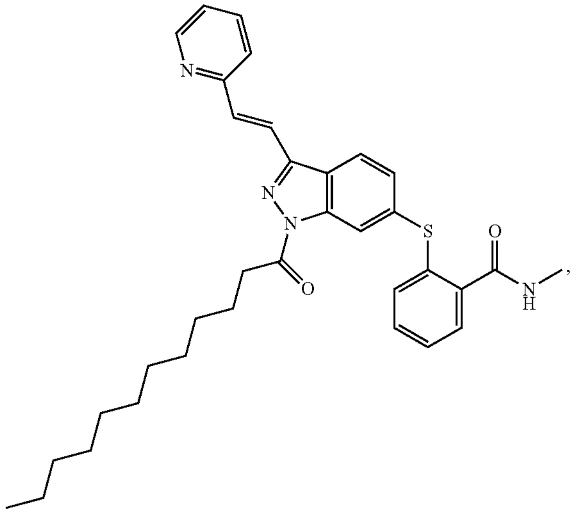

-continued
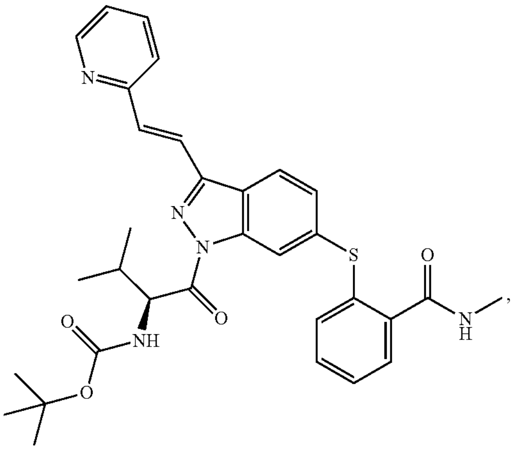
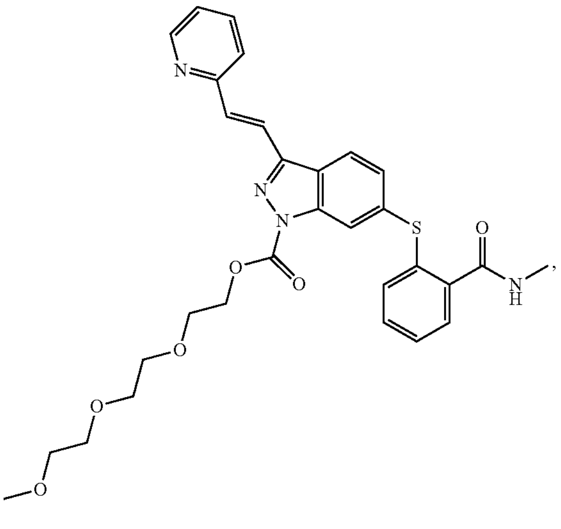
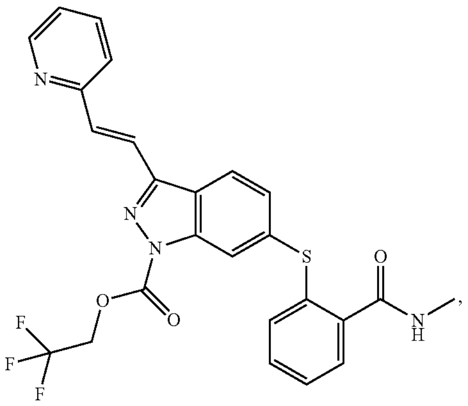
-continued
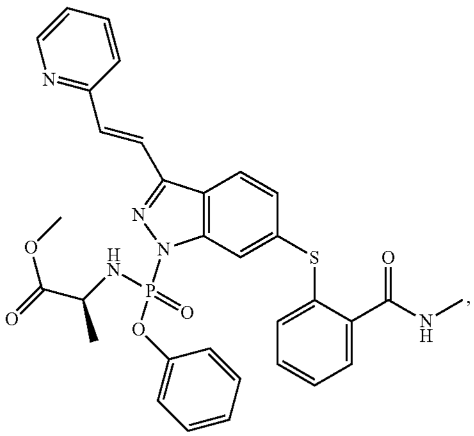
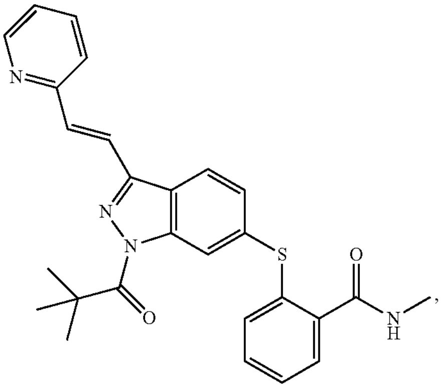
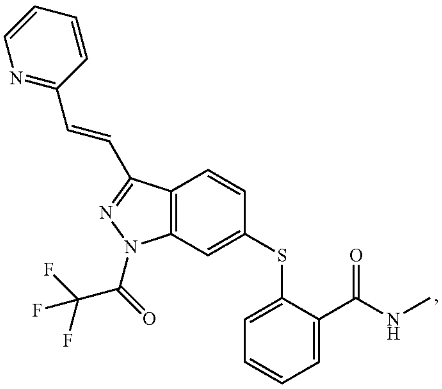
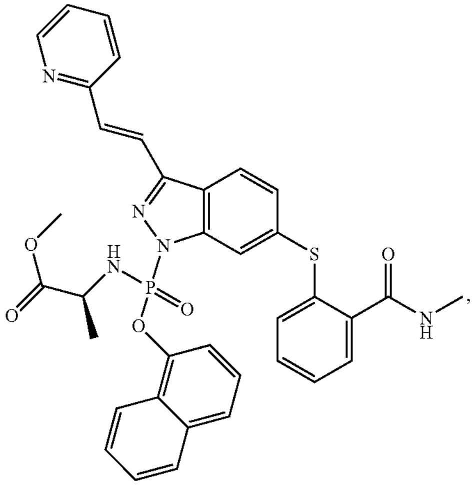

-continued
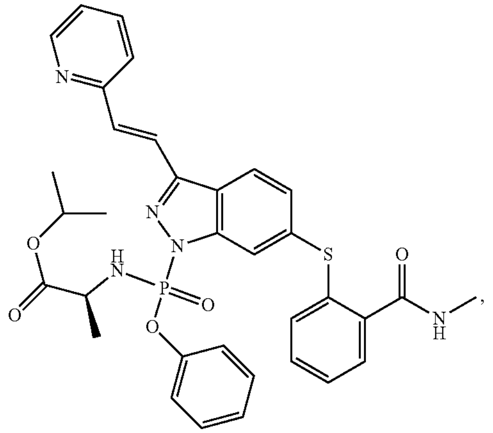
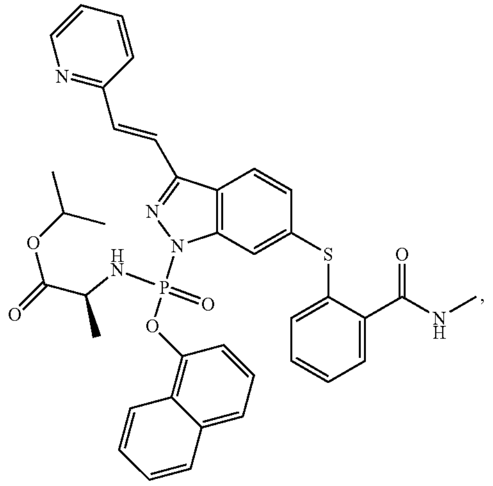
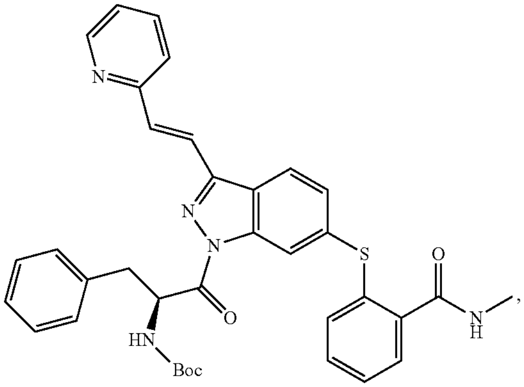
-continued
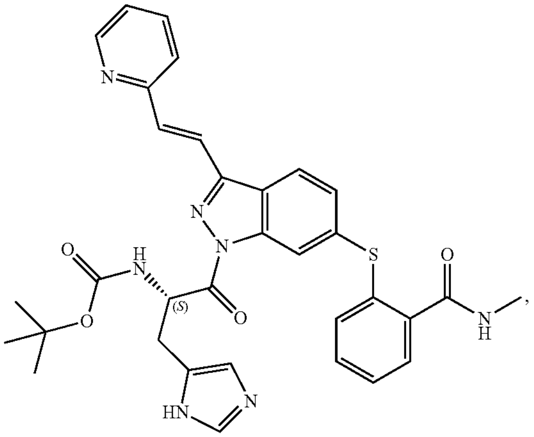
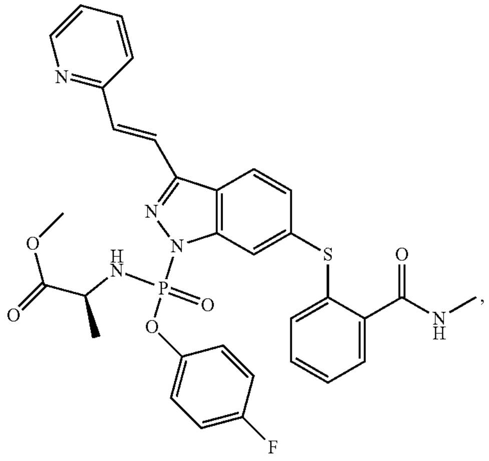
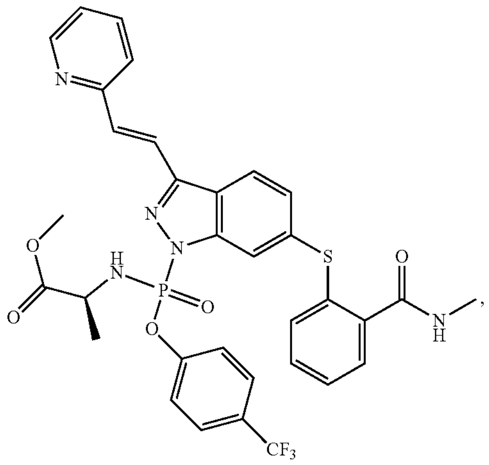

-continued
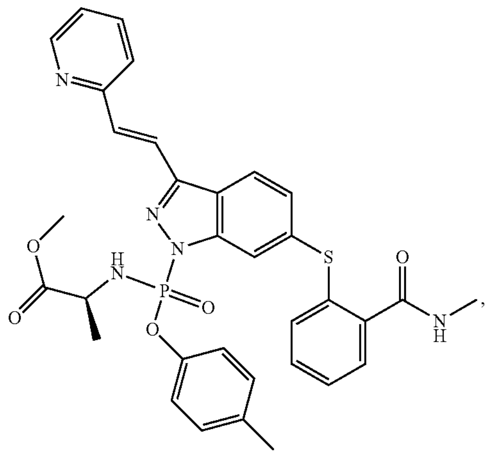
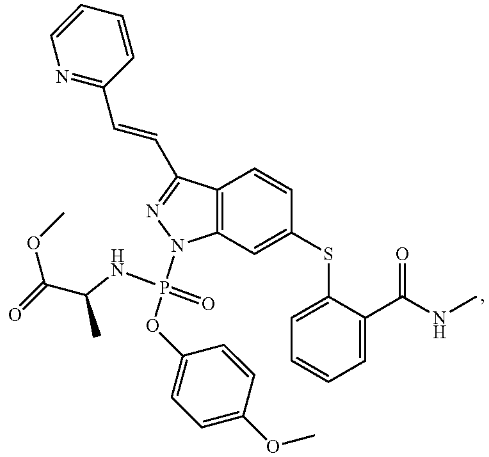
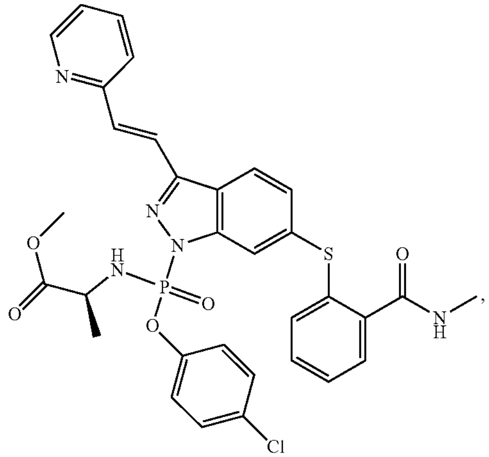
-continued
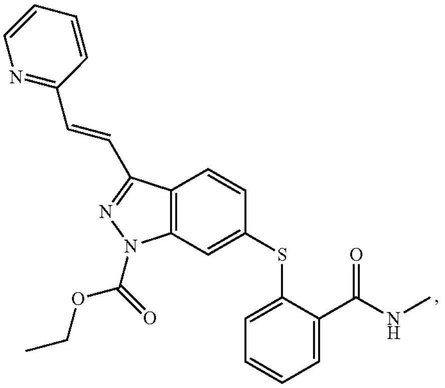 [SMILES: CCOC(=O)n1nc(/C=C/c2ccccn2)c2ccc(Sc3ccccc3C(=O)NC)cc21]
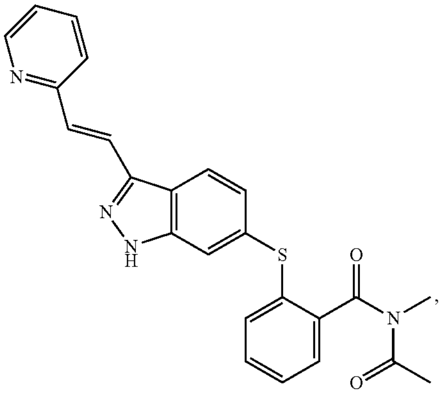
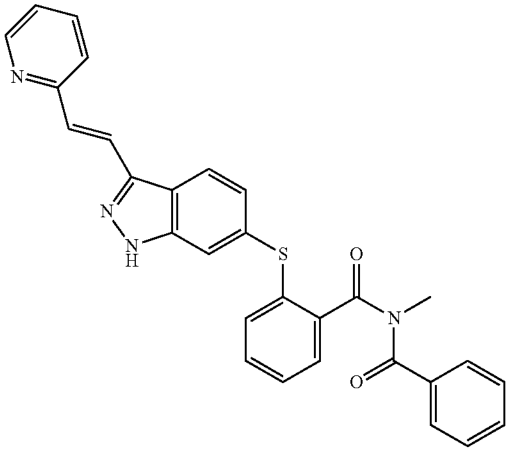
, -continued
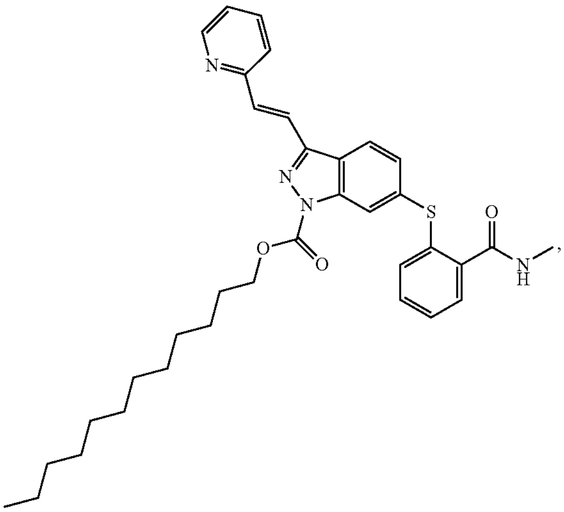
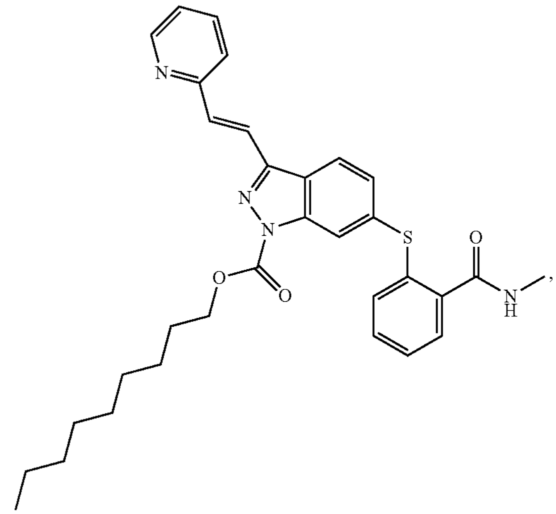
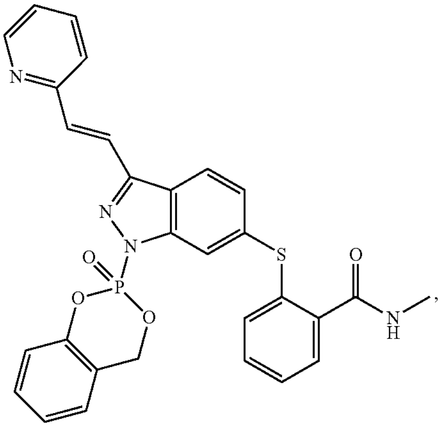
-continued
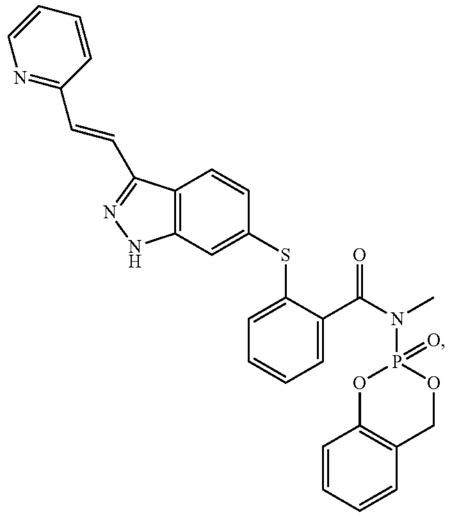
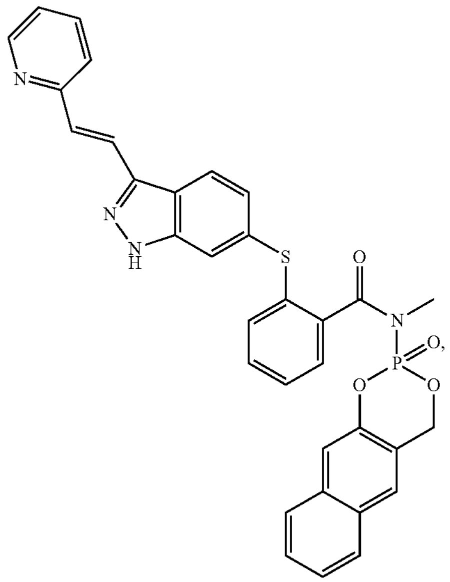
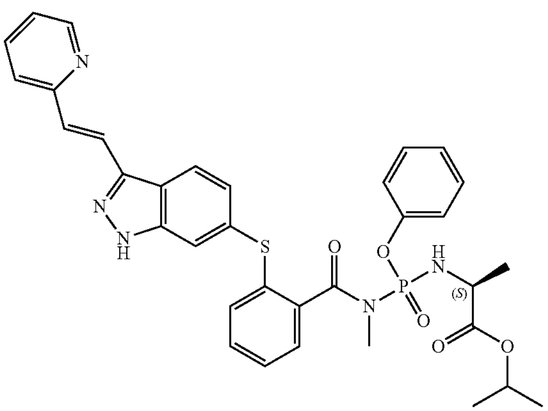
, -continued
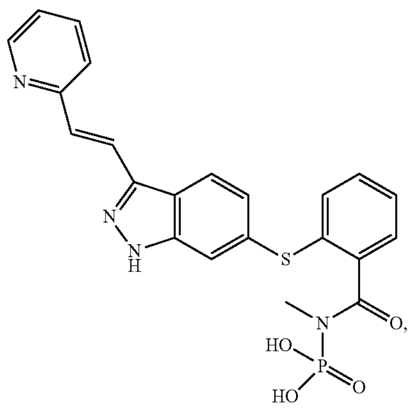
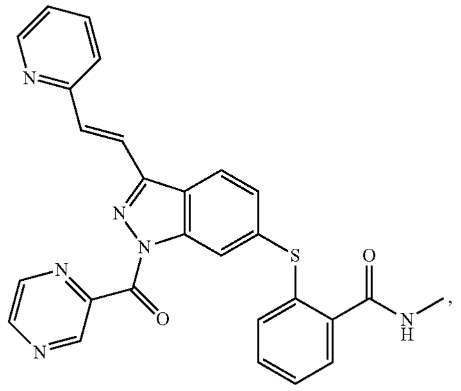
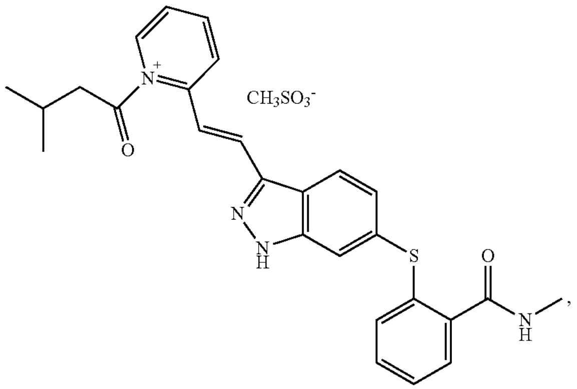
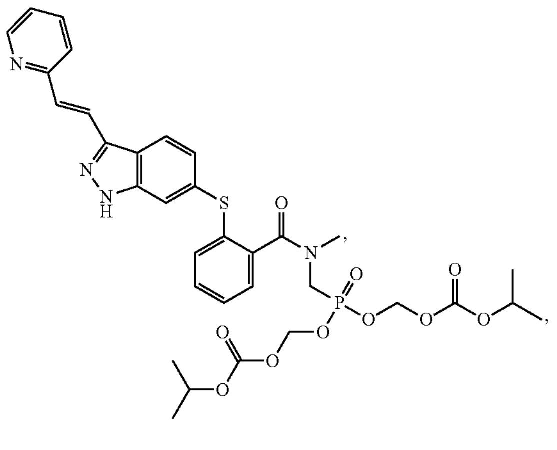
-continued
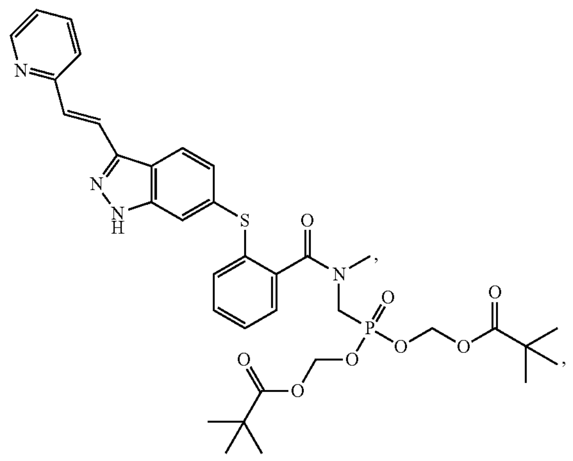
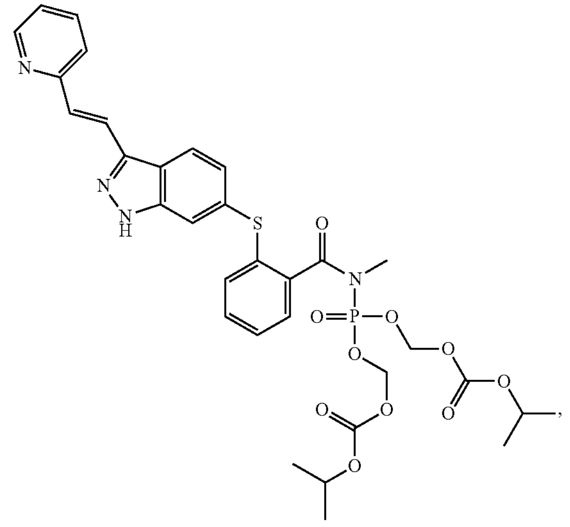
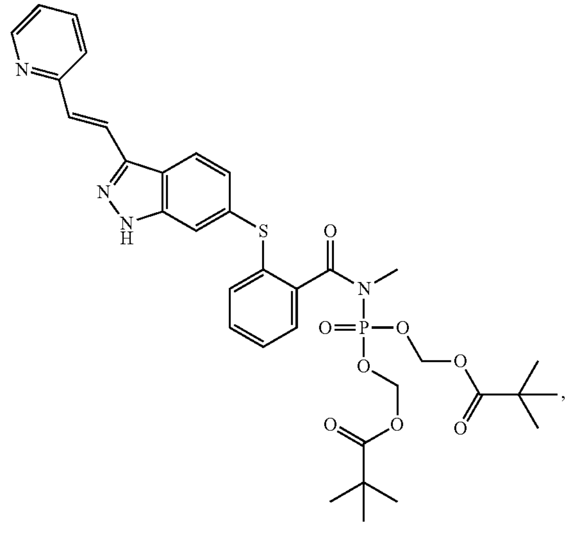

-continued
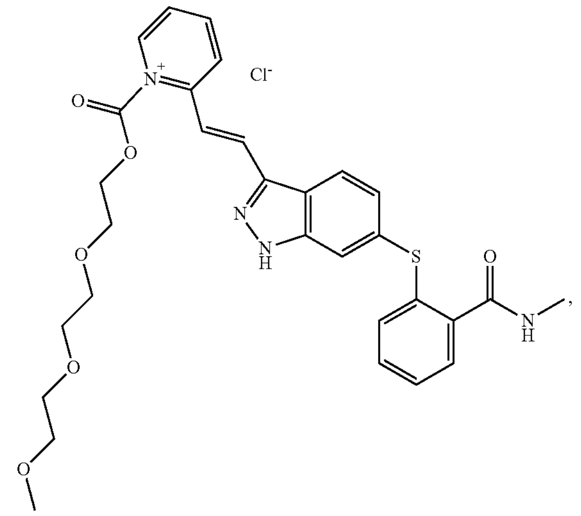
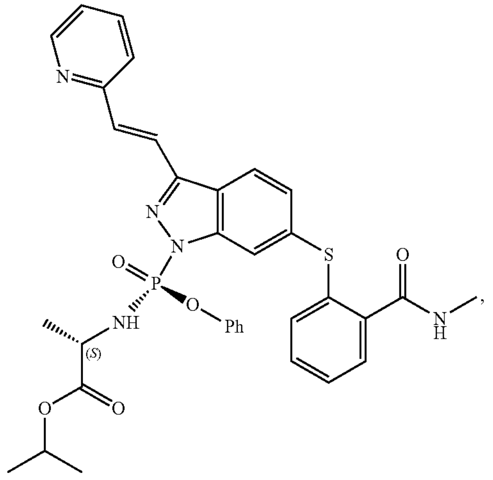
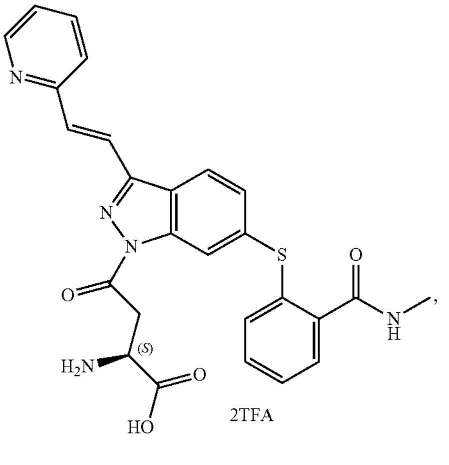
-continued
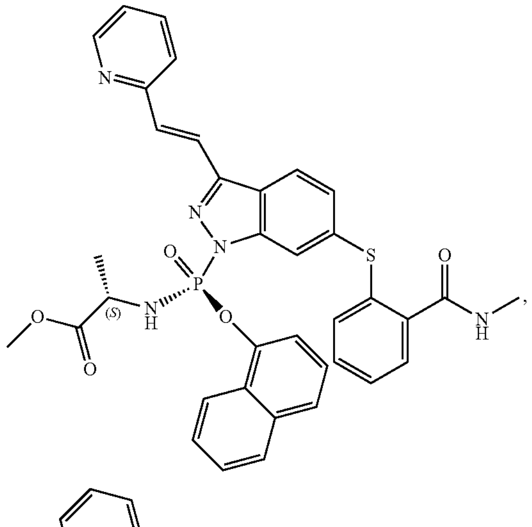
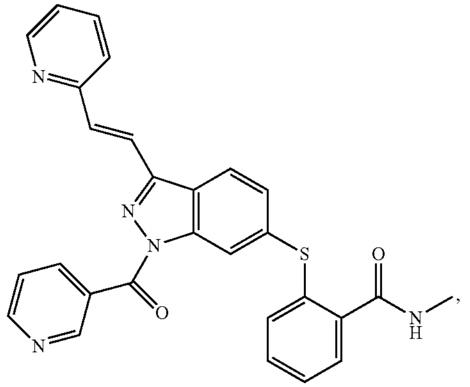
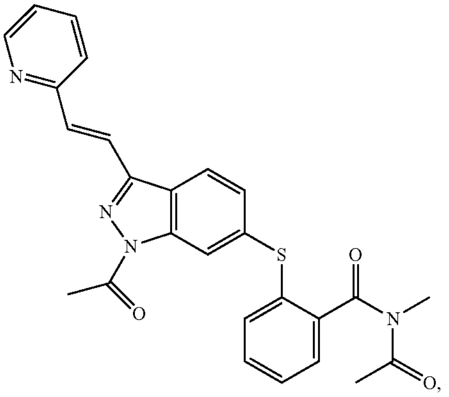
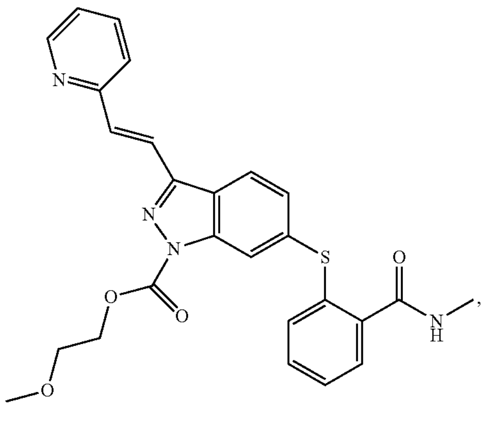

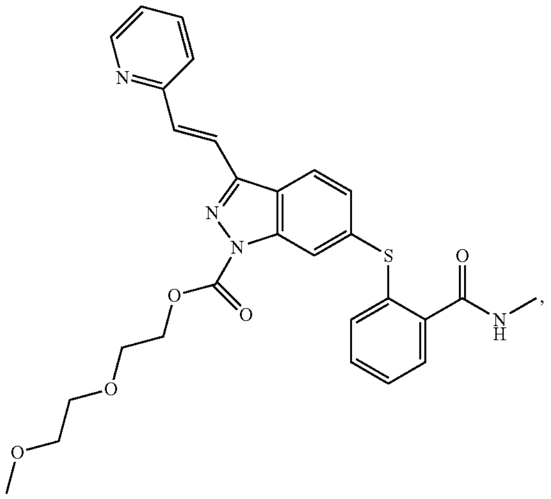
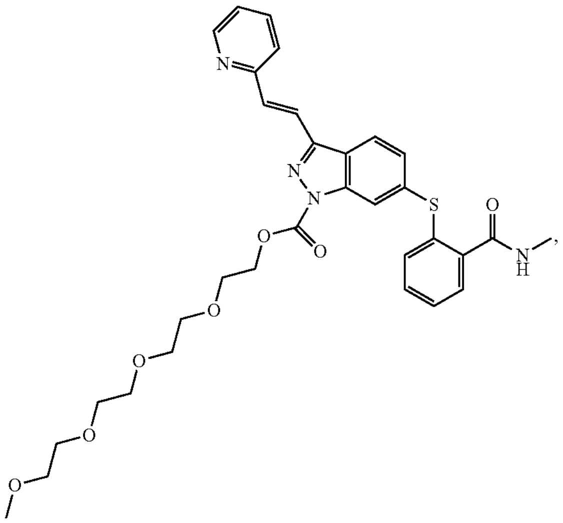
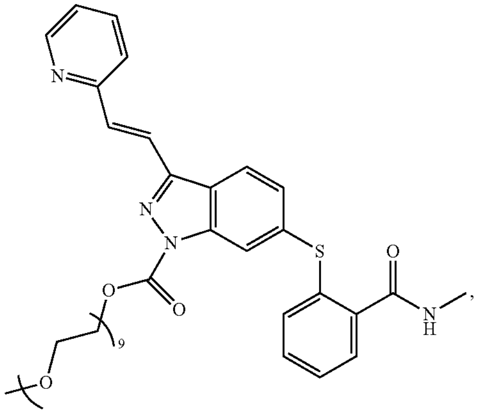
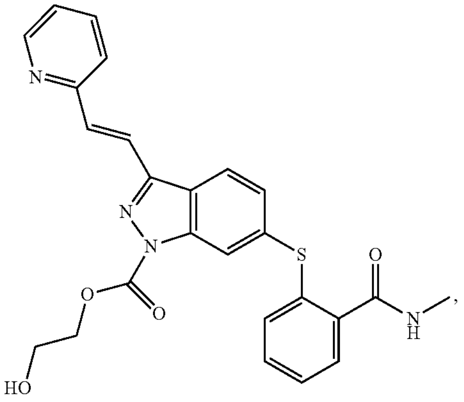
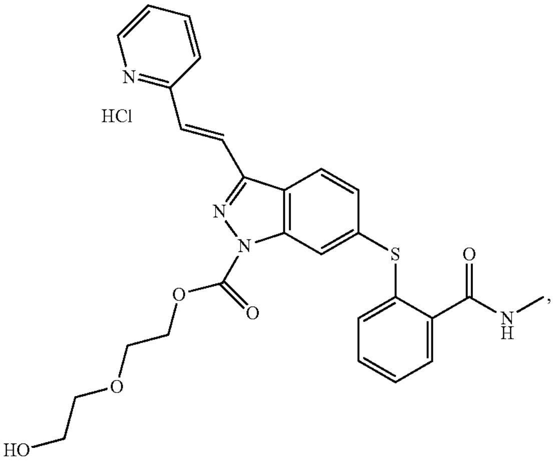
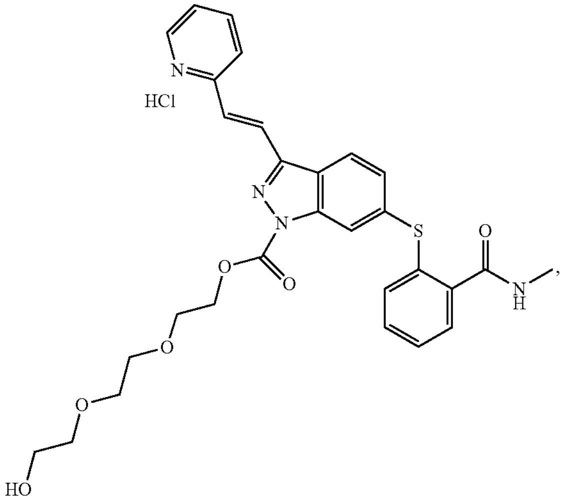

-continued
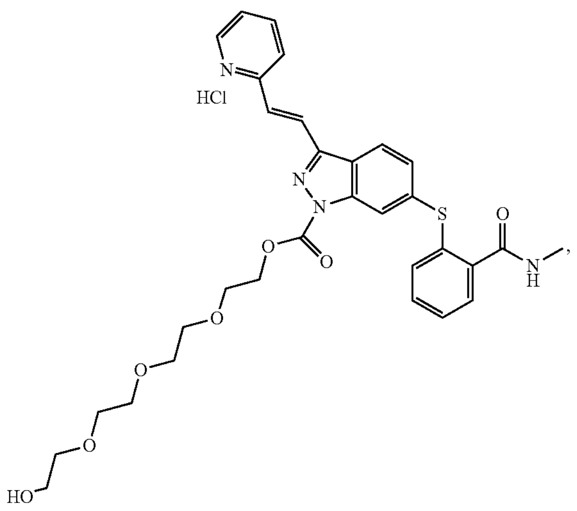
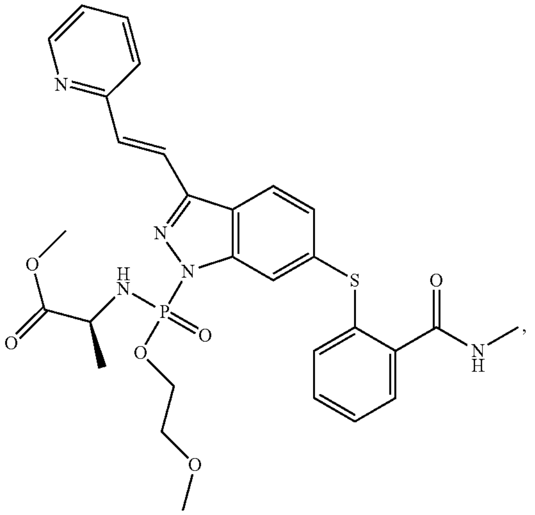
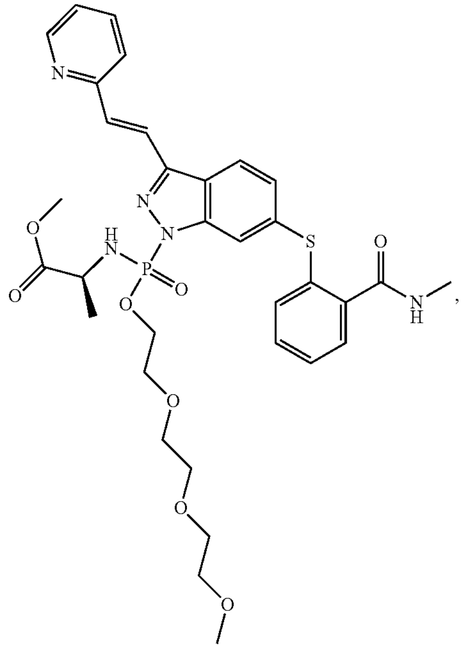
-continued
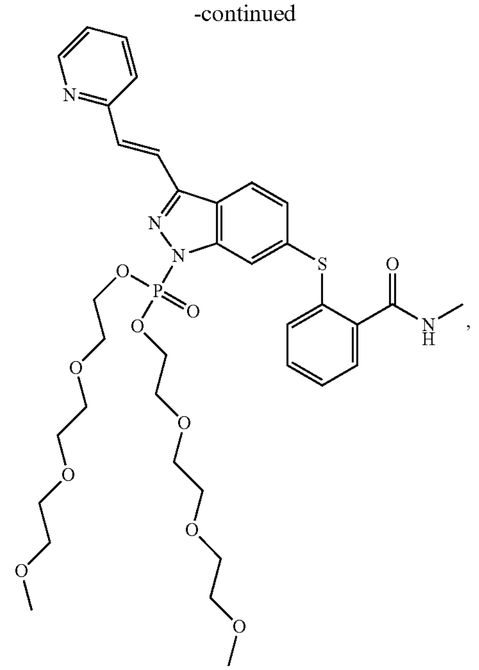
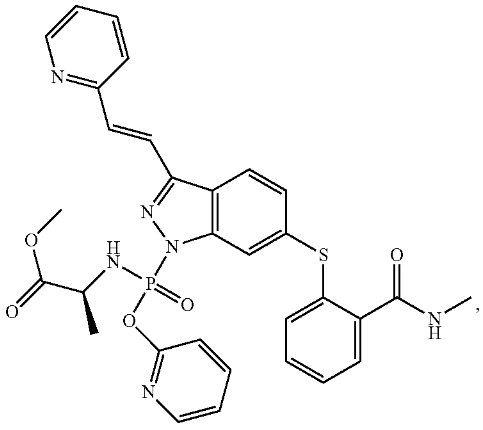
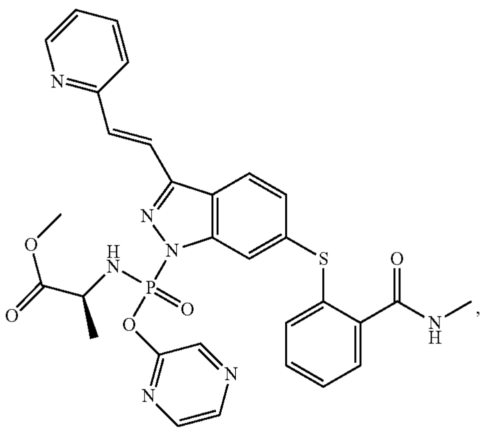

-continued
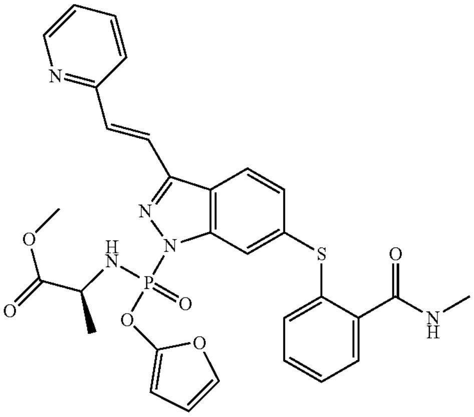
,
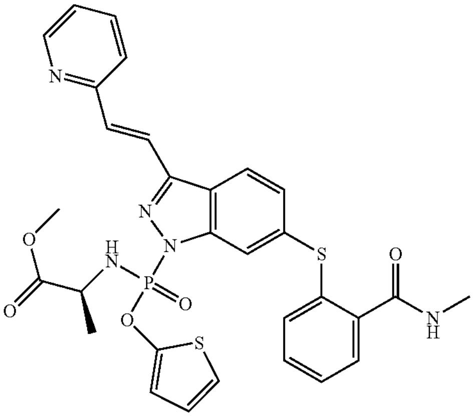
,
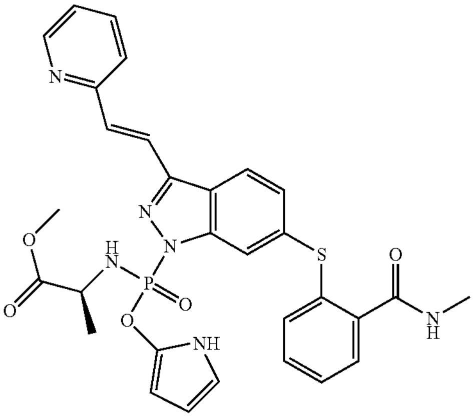
,
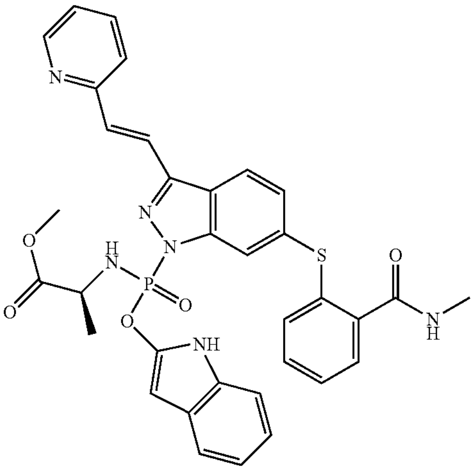
,
-continued
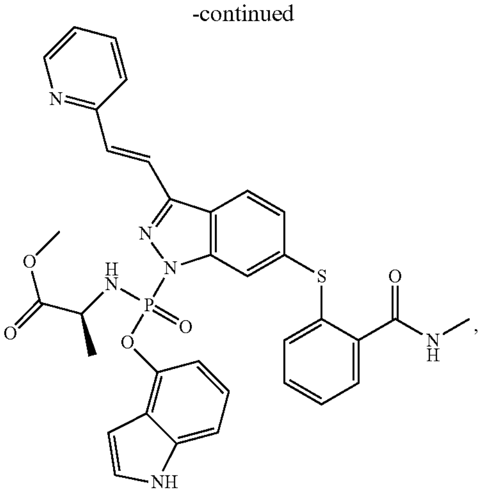
,
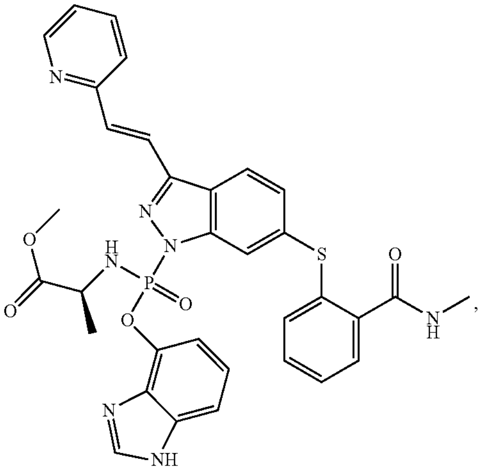
,
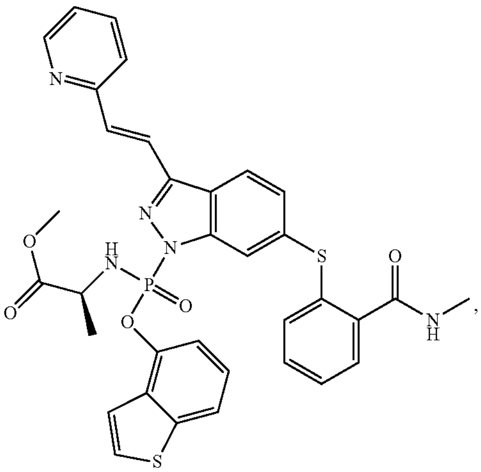
, -continued
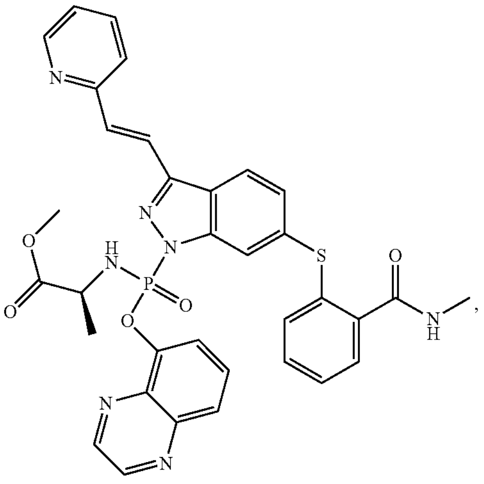
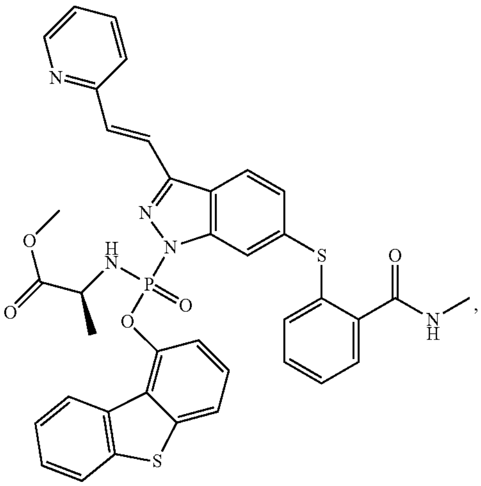
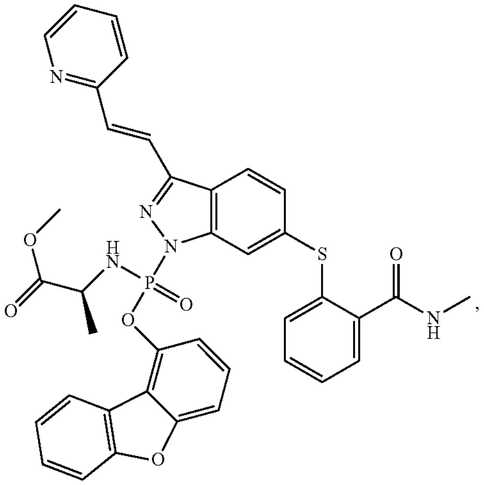
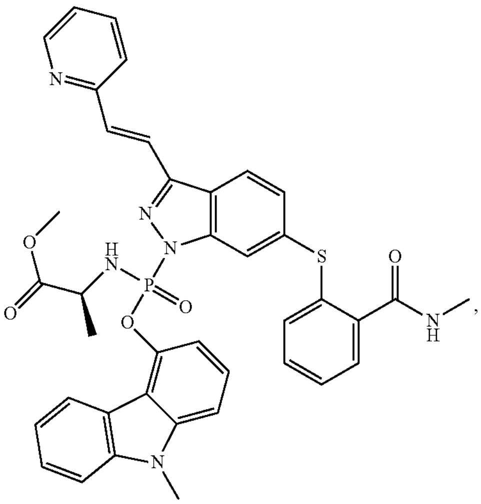
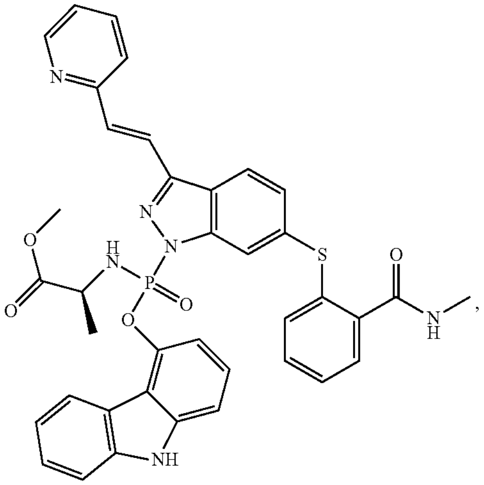
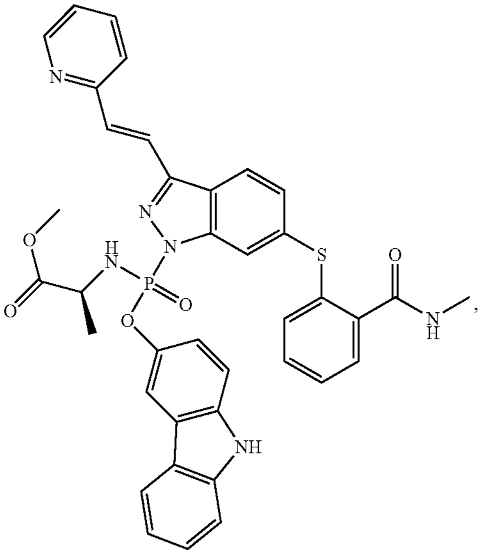

-continued
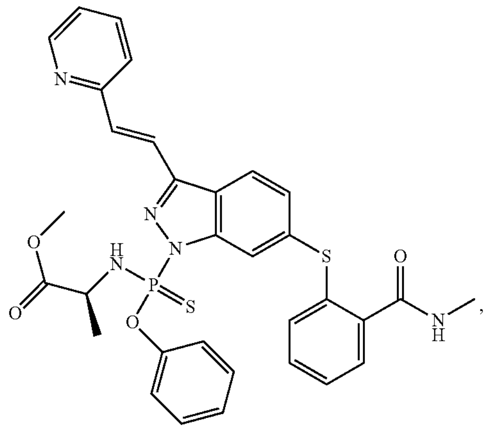
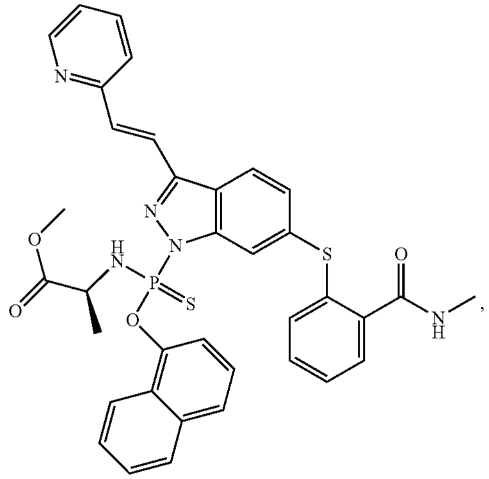
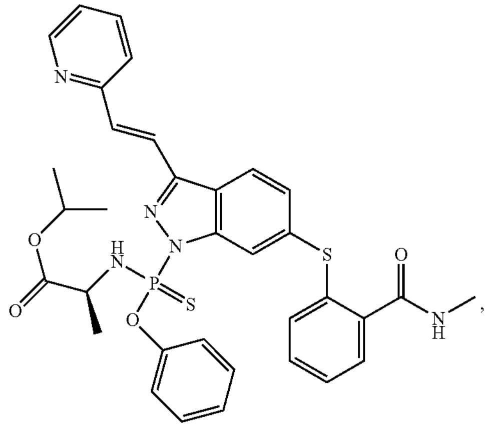
-continued
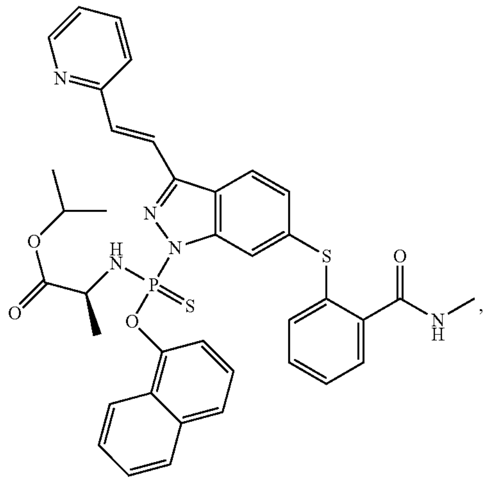
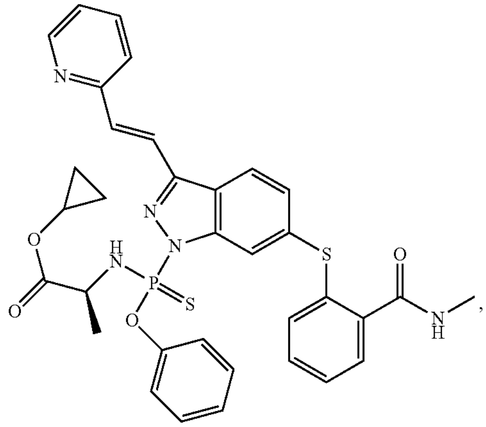
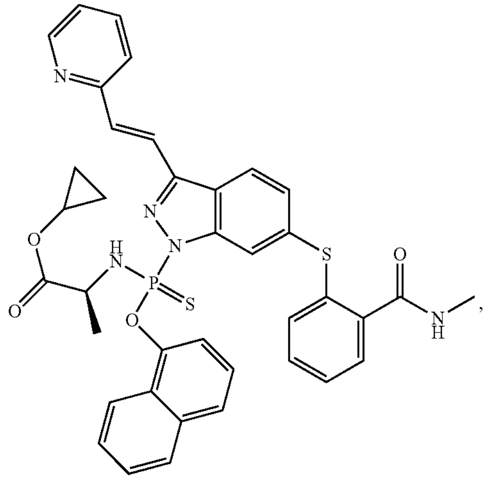

-continued
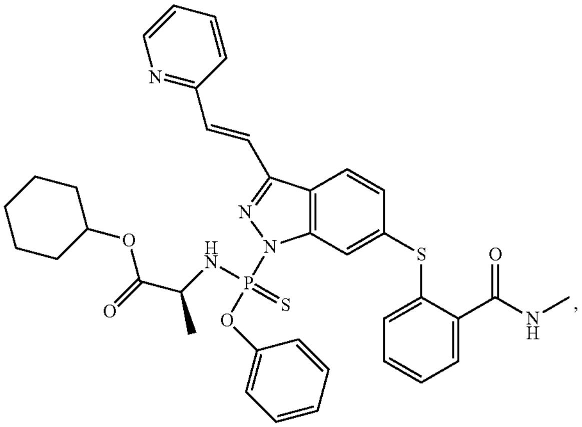
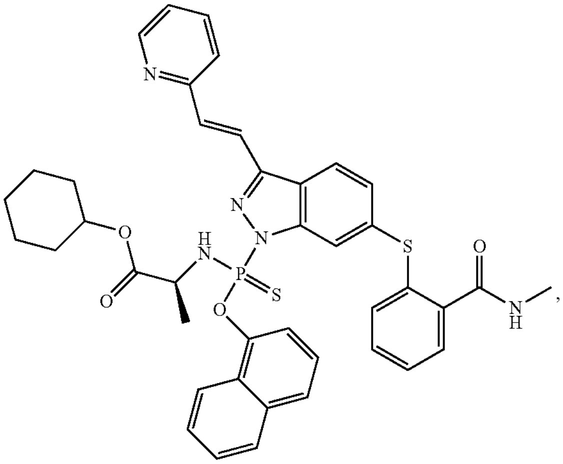
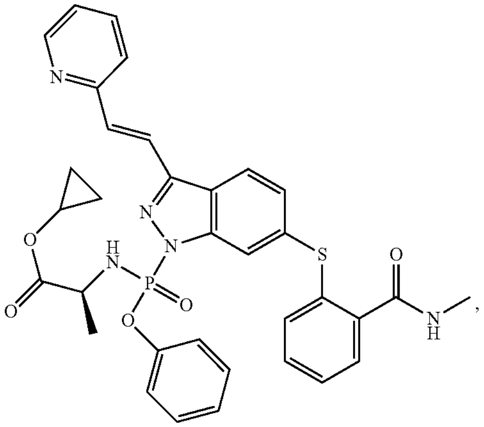
-continued
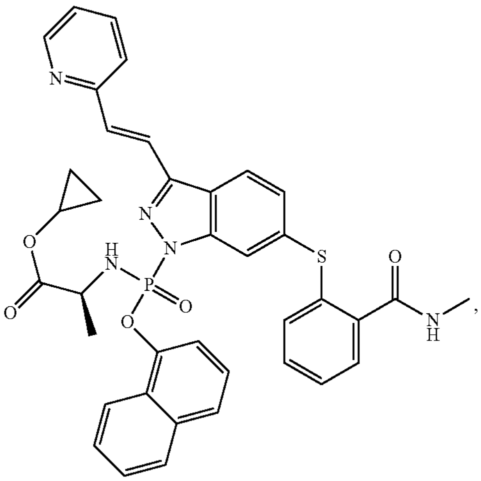
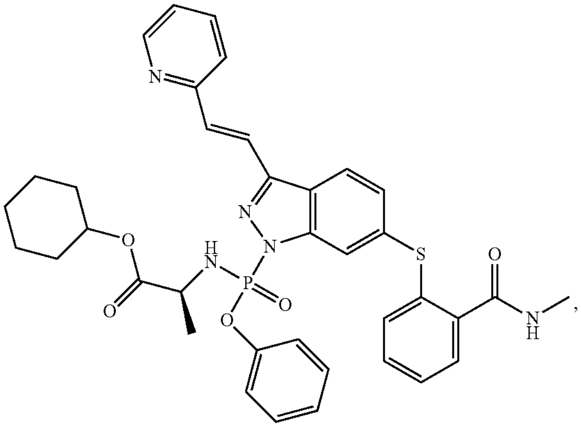
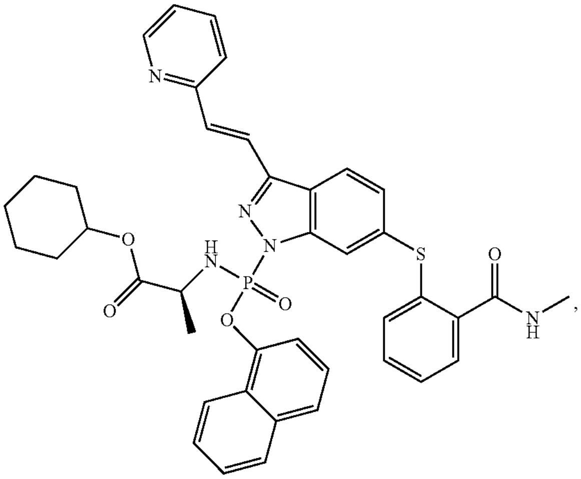

-continued
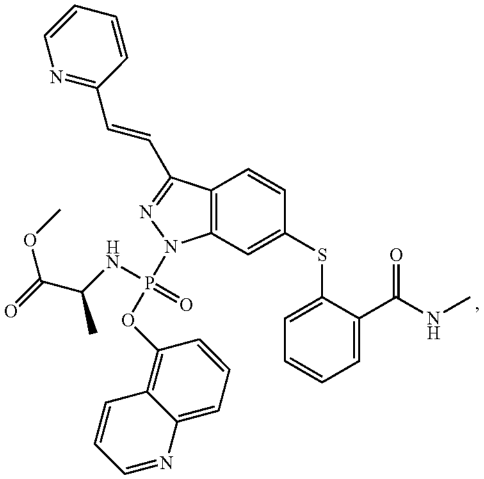
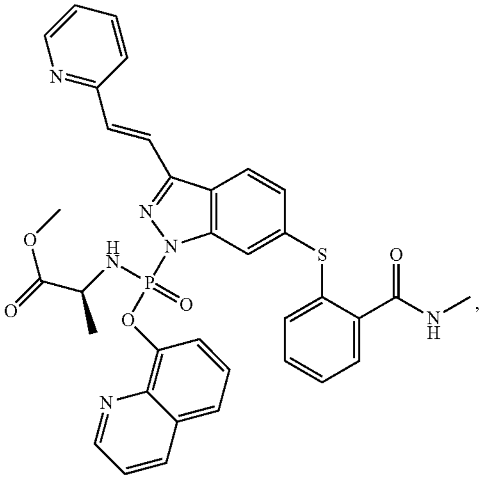
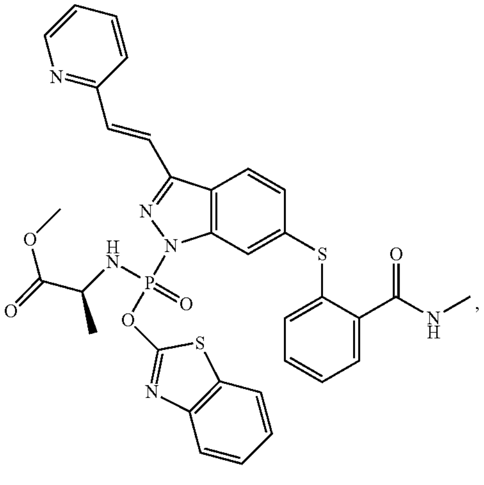
-continued
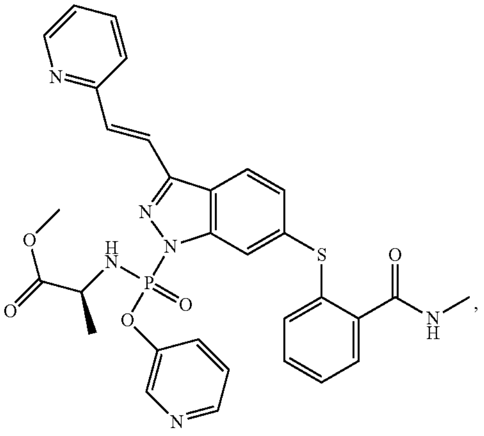
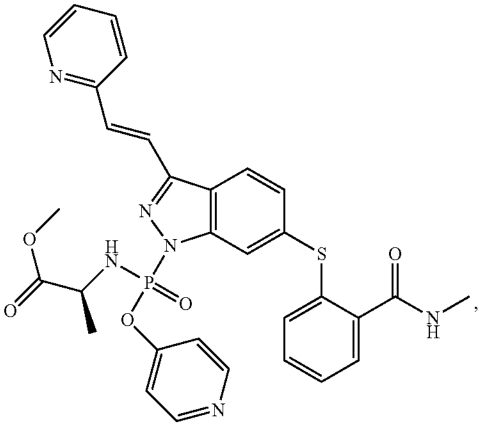
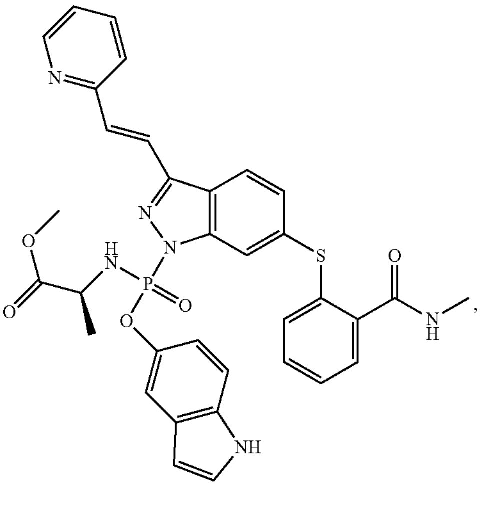

-continued
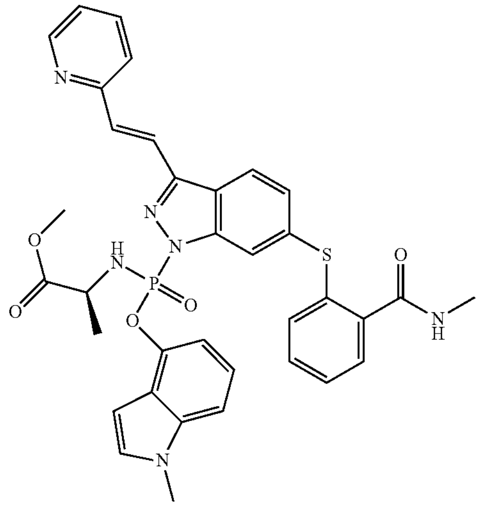
,
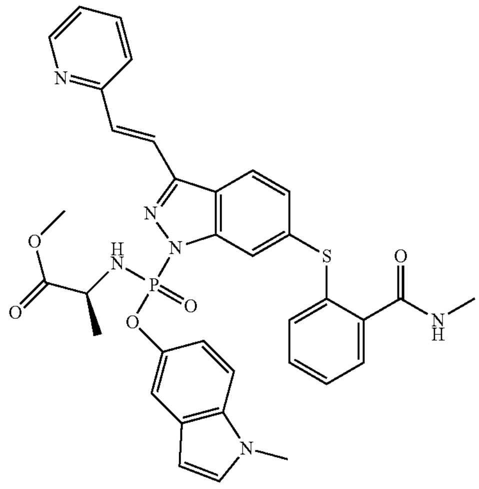
,
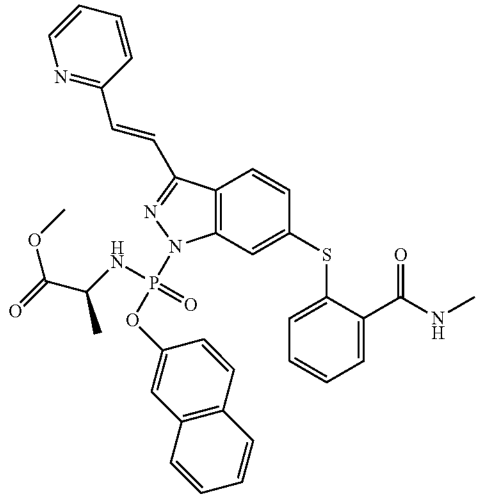
,
-continued
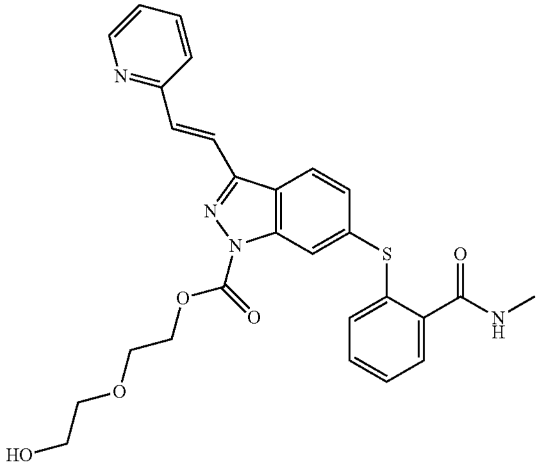
,
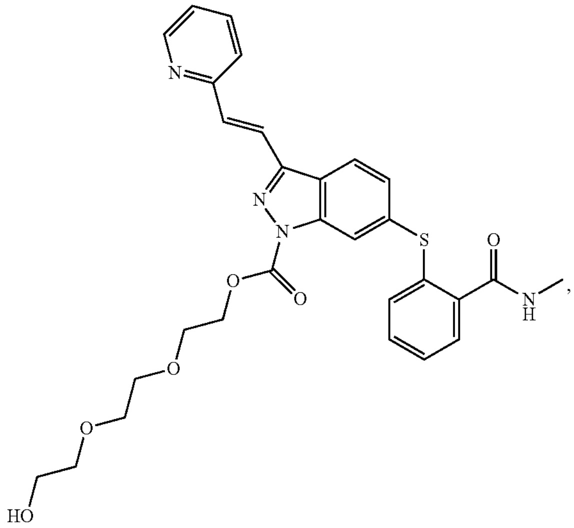
,
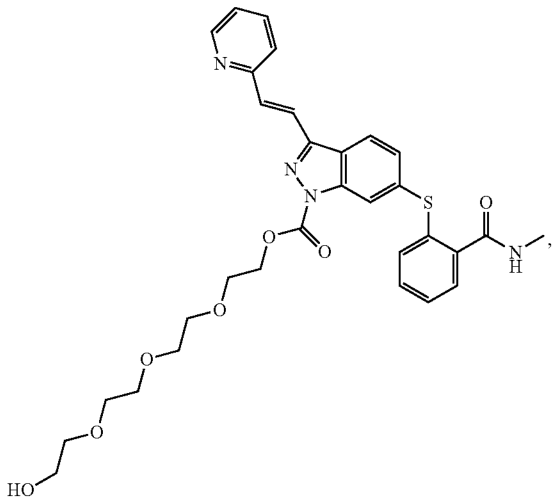
, -continued

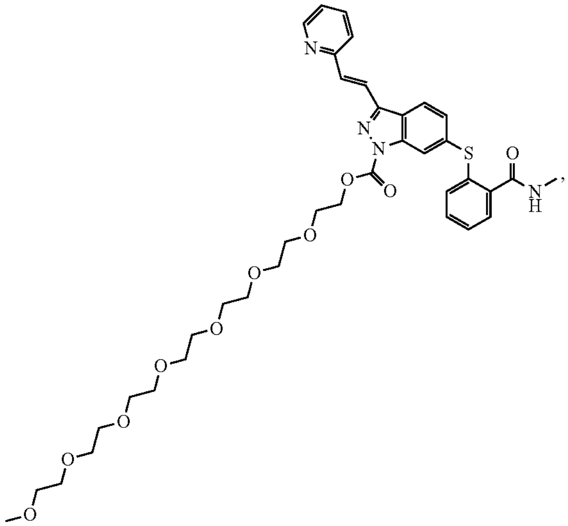

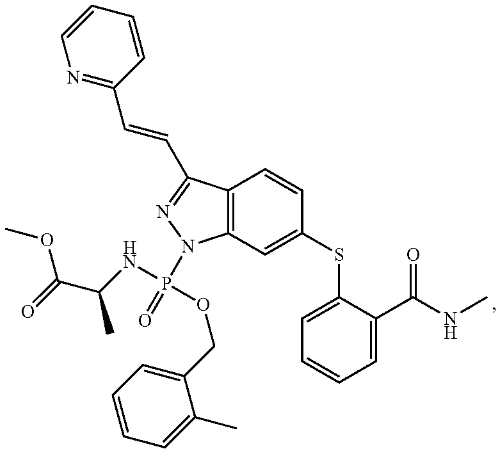

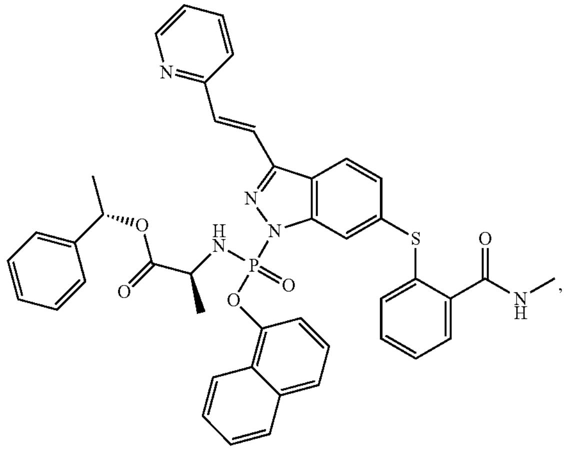

-continued

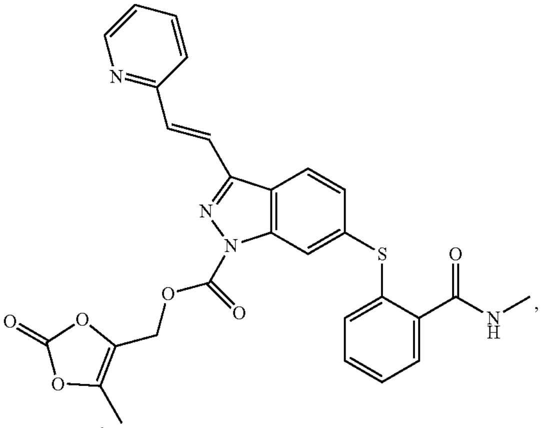

, or

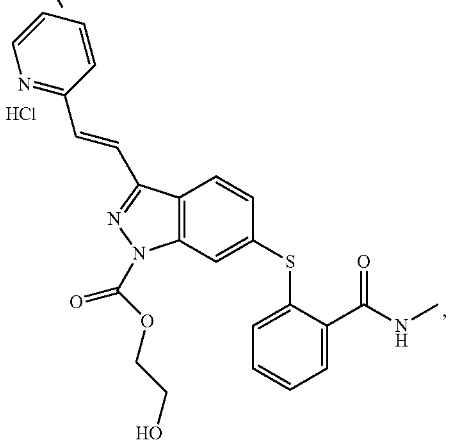

or a pharmaceutically-acceptable salt or ester thereof.

9. The compound of claim 1, wherein the compound is a prodrug of axitinib.

10. A pharmaceutical composition comprising the compound of claim 1 and a pharmaceutically acceptable carrier.

11. A method for the inhibition or modulation of the activity of a tyrosine kinase in a subject, comprising administering to the subject an effective amount of the compound of claim 1, such that the tyrosine kinase is inhibited or modulated in the subject.

12. The method of claim 11, wherein the subject suffers from a tumor or a cancer.

13. The method of claim 12, wherein the tumor or the cancer is a solid tumor.

14. The method of claim 12, wherein the tumor or the cancer is breast cancer, renal cell carcinoma, or thyroid cancer.

15. The method of claim 11, wherein the subject is a mammal.

16. The method of claim 15, wherein the mammal is a human.

17. A pharmaceutical composition comprising the compound of claim 8 and a pharmaceutically acceptable carrier.

18. A method for the inhibition or modulation of the activity of a tyrosine kinase in a subject, comprising administering to the subject an effective amount of the compound of claim 8, such that the tyrosine kinase is inhibited or modulated in the subject.

19. The method of claim 18, wherein the subject suffers from a tumor or a cancer.

20. The method of claim 18, wherein the subject is a human.

* * * * *